United States Patent
Galley et al.

(10) Patent No.: US 8,118,770 B2
(45) Date of Patent: Feb. 21, 2012

(54) RECONCILING MULTIPLE MEDICAL DEVICE BOLUS RECORDS FOR IMPROVED ACCURACY

(75) Inventors: Paul J. Galley, Cumberland, IN (US); Maury Zivitz, Indianapolis, IN (US); Stefan Weinert, Pendleton, IN (US); Robert Hellwig, Bern (CH)

(73) Assignees: Roche Diagnostics Operations, Inc., Indianapolis, IN (US); Roche Diagnostics International Ltd., Steinhausen (CH)

( * ) Notice: Subject to any disclaimer, the term of this patent is extended or adjusted under 35 U.S.C. 154(b) by 0 days.

(21) Appl. No.: 12/646,336

(22) Filed: Dec. 23, 2009

(65) Prior Publication Data

US 2010/0168660 A1    Jul. 1, 2010

Related U.S. Application Data

(63) Continuation of application No. PCT/US2008/066331, filed on Jun. 9, 2008.

(60) Provisional application No. 60/937,779, filed on Jun. 29, 2007, provisional application No. 60/937,933, filed on Jun. 29, 2007.

(51) Int. Cl.
*A61M 31/00* (2006.01)

(52) U.S. Cl. .......................................... 604/66; 604/500

(58) Field of Classification Search ..................... 604/56, 604/66, 67; 600/365
See application file for complete search history.

(56) References Cited

U.S. PATENT DOCUMENTS 4,146,029 A    3/1979   Ellinwood, Jr.
(Continued)

FOREIGN PATENT DOCUMENTS

EP    0079405 A1    5/1983
(Continued)

OTHER PUBLICATIONS

The Bluetooth Forum: "Bluetooth security", Internet citation [online], Feb. 22, 2001. XP002171382. http://www.bluetooth.com/developer/specifiction/specification.asp.
Gehrmann, Christian, "Bluetooth Security White Paper, Bluetooth SIG", Bluetooth Doc, Apr. 19, 2002, pp. 1-46. XP003010085.
Levy, M., et al., "Fifo Memories Supply the Glue for High-Speed Systems", EDN Eleectrical Design News, Reed Business Information, Highlands Ranch, Co, US, vol. 42, No. 6, Mar. 14, 1997, pp. 65, 66, 68 and 70. XP 000695233.

(Continued)

*Primary Examiner* — Nicholas Lucchesi
*Assistant Examiner* — Aarti B Berdichevsky
(74) *Attorney, Agent, or Firm* — Eric R. Waldkoetter; Roche Diagnostics Operation, Inc.

(57) ABSTRACT

An electronic device may be configured to prompt a user via an on-board display to measure user glucose via an on-board glucose meter, to compute a first drug bolus value based on the measured user glucose, to display the first drug bolus value on the display and prompt the user via the display to enter carbohydrate information into the device, to compute a second drug bolus value based on the entered carbohydrate information, to display the second drug bolus value on the display and prompt the user via the display to enter user health information into the device, to compute a third drug bolus value based on the entered health information and a total drug bolus value as a sum of the first, second and third drug bolus values, and to display the third and total drug bolus values on the display.

8 Claims, 26 Drawing Sheets

U.S. PATENT DOCUMENTS

| | | | |
|---|---|---|---|
| 5,291,609 | A | 3/1994 | Herz |
| 5,364,346 | A | 11/1994 | Schrezenmeir |
| 5,748,103 | A | 5/1998 | Flach et al. |
| 5,997,475 | A | 12/1999 | Bortz |
| 6,289,421 | B1 | 9/2001 | Ali et al. |
| 6,668,196 | B1 | 12/2003 | Villegas et al. |
| 6,909,439 | B1 | 6/2005 | Amro et al. |
| 7,291,107 | B2 * | 11/2007 | Hellwig et al. ............... 600/365 |
| 7,553,281 | B2 * | 6/2009 | Hellwig et al. ............... 600/365 |
| 7,651,845 | B2 * | 1/2010 | Doyle et al. ................... 435/14 |
| 2001/0044731 | A1 | 11/2001 | Coffman et al. |
| 2003/0212379 | A1* | 11/2003 | Bylund et al. ................ 604/504 |
| 2004/0078416 | A1 | 4/2004 | Kawasaki et al. |
| 2004/0248840 | A1 | 12/2004 | Hansen et al. |
| 2005/0091577 | A1 | 4/2005 | Torres et al. |
| 2005/0162395 | A1 | 7/2005 | Unruh |
| 2006/0047192 | A1 | 3/2006 | Hellwig et al. |
| 2006/0173406 | A1 | 8/2006 | Hayes et al. |
| 2006/0217061 | A1 | 9/2006 | Steele et al. |
| 2007/0109325 | A1 | 5/2007 | Eveleigh |
| 2007/0142767 | A1 | 6/2007 | Frikart et al. |
| 2009/0247931 | A1* | 10/2009 | Damgaard-Sorensen ...... 604/19 |

FOREIGN PATENT DOCUMENTS

| | | |
|---|---|---|
| EP | 0290683 A2 | 11/1988 |
| EP | 1759726 A2 | 3/2007 |
| EP | 1788501 A1 | 5/2007 |
| EP | 1795116 A1 | 6/2007 |
| WO | 00/48112 A2 | 8/2000 |
| WO | 2004/099898 A2 | 11/2004 |
| WO | 2006/032653 A2 | 3/2006 |
| WO | 2006/046015 A1 | 5/2006 |
| WO | 2006/108304 A1 | 10/2006 |

OTHER PUBLICATIONS

Hastings, C., et al., "Future Trends in Fifo Architectures", Wescon Technical Papers, Western Periodicals Co., North Hollywood, CA, USA, vol. 36, Nov. 17, 1992, pp. 174-178. XP 000350089.

Rasid, M. F. A., et al., "Bluetooth Telemedicine Processor for Multichannel Biomedical Signal Transmission via Mobile Cellular Netowrks", IEEE Transactions on Information Technology in Biomedicine, IEEE Service Center, Los Alamitos, CA, USA, vol. 9, No. 1, Mar. 1, 2005, pp. 35-43. XP 011127538.

International Search Report and Written Opinion mailed Jul. 24, 2008 from PCT/US2008/066247.

International Search Report and Written Opinion mailed Oct. 30, 2008 from PCT/US2008/066288.

International Search Report and Written Opinion mailed Dec. 22, 2008 from PCT/US2008/066267.

International Search Report and Written Opinion mailed Jan. 9, 2009 from PCT/US2008/066248.

International Search Report and Written Opinion mailed Dec. 22, 2008 from PCT/US2008/066299.

International Search Report and Written Opinion mailed Jan. 14, 2009 from PCT/US2008/066331.

International Search Report and Written Opinion mailed Jan. 14, 2009 from PCT/US2008/066262.

* cited by examiner

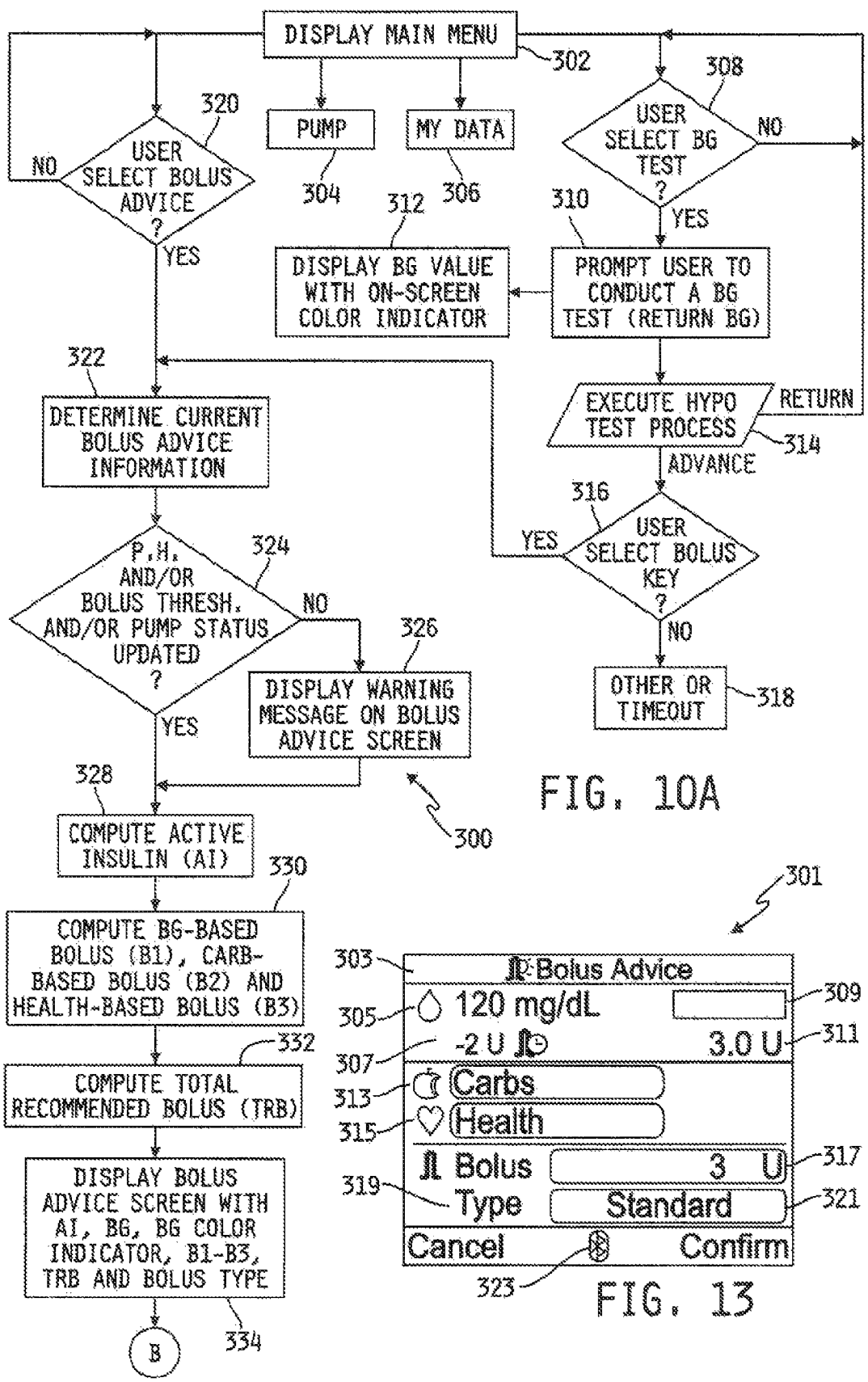

RECONCILING MULTIPLE MEDICAL DEVICE BOLUS RECORDS FOR IMPROVED ACCURACY

REFERENCE

This application is a continuation of PCT/US2008/066331 filed Jun. 9, 2008 which is based on and claims priority to U.S. Provisional Patent Application Ser. No. 60/937,779 and U.S. Provisional Patent Application Ser. No. 60/937,933, both filed Jun. 29, 2007, all applications in this paragraph are hereby incorporated by reference.

FIELD

This disclosure relates generally to electronic devices that may include one or more on-board medical devices, and more specifically to such electronic devices configured to wirelessly communicate with at least one off-board medical device.

BACKGROUND

Remote electronic devices for wirelessly communicating with at least one, medical device are known. It is desirable to include on the remote electronic device an on-board medical device, and/or to conduct wireless communications between the remote electronic device and an off-board medical device for the purpose of commanding operation of the off-board medical device with the remote electronic device.

SUMMARY

The present invention may comprise one or more of the features recited in the attached claims, and/or one or more of the following features and combinations thereof. A method for determining a drug bolus for a user via an electronic device including an on-board glucose meter and a display may comprise displaying a bolus recommendation screen on the display unit, including in the bolus recommendation screen a glucose value field for displaying glucose values of the user that are measured by the on-board glucose meter and automatically entered into the glucose value field, including in the bolus recommendation screen a carbohydrate field for displaying carbohydrate information entered into the electronic device, the carbohydrate information corresponding to carbohydrate contents of meals or snacks taken or planned to be taken by the user, including in the bolus recommendation screen a health field for displaying health information entered into the electronic device, the health information corresponding to a health condition or activity of the user, and including in the bolus recommendation screen a total bolus field for displaying based on the values in the glucose value field, the carbohydrate field and the health field.

The method may further comprise prompting the user to measure glucose concentration of body fluid of the user via the on-board glucose meter if at least a time period has elapsed since last measuring the glucose concentration of the body fluid of the user, and displaying subsequently measured glucose concentration of the user in the glucose value field. The method may further comprise displaying no glucose concentration value in the glucose value field if the user does not measure glucose concentration via the on-board glucose meter in response to the prompt to measure glucose concentration of body fluid of the user via the on-board glucose meter.

The method may further comprise displaying in the glucose value field the most recent glucose concentration of the user that was measured by the on-board glucose meter if the at least a time period has not elapsed since last measuring the glucose concentration of the body fluid of the user.

The electronic device may comprise a plurality of user buttons. The method may further comprise entering the carbohydrate information via into the electronic device via one or more of the plurality of user buttons. Alternatively or additionally, the method may further comprise entering the health information into the electronic device via one or more of the plurality of user buttons. The health field may include a plurality of health descriptions. The user may enter the health information into the electronic device by selecting one of the plurality of health descriptions via the one or more of the plurality of user buttons. The plurality of health descriptions may include a no selection and at least one of exercise, stress and illness.

The method may further comprise including in the bolus recommendation screen a confirmation indicator that the user can select via at least one of the plurality of user buttons to confirm delivery of the total recommended bolus value displayed in the total bolus field. Each of the glucose value field, the carbohydrate field and the health field may be repeatedly accessible until the confirmation indicator is selected.

The electronic device may comprise a wireless communication circuit. The method may further comprise transmitting a command via the wireless communication circuit to command a liquid infusion pump to deliver a bolus in the amount of the total recommended bolus value displayed in the total bolus field.

The method may further comprise including in the bolus recommendation screen a bolus type field for displaying a bolus type entered into the electronic device, the bolus type corresponding to a type of bolus delivery. The electronic device may comprise a plurality of user buttons. The method may further comprise entering the bolus type into the electronic device via one or more of the plurality of user buttons. The bolus type field may include a plurality of bolus type choices. The user may enter the bolus type into the electronic device by selecting one of the plurality bolus type choices via the one or more of the plurality of user buttons. The plurality of bolus type choices may include a standard bolus, a multi-wave bolus, an extended bolus, a manually programmed pump bolus and a bolus manually delivered via a pen or syringe.

A medical system may comprise a liquid infusion pump including a first processor and a first wireless communication circuit for receiving remotely generated commands, the first processor including a memory having instructions stored therein that are executable by the first processor to control the liquid infusion pump to deliver liquid to a body of a user, and a remote electronic device including an on-board blood glucose meter, a second processor and a second wireless communication device for transmitting wireless commands, the second processor executing a bolus recommendation process that recommends a bolus amount based on one or more of blood glucose measurements made by the on-board glucose meter, carbohydrate values entered by a user and corresponding to carbohydrate values of meals or snacks, and health information entered by the user and corresponding to health activities or conditions of the user, the second processor including a memory having instructions stored therein that are executable by the second processor to send via the second wireless communication circuit a wireless command to deliver a bolus in the amount of the recommended bolus amount when the user confirms selection of the recommended bolus amount. The liquid infusion pump may be responsive to the wireless command to deliver insulin in the amount of the user confirmed recommended bolus amount.

A method of remotely commanding via a remote electronic device delivery of an amount of liquid by a liquid infusion pump may comprise determining with the remote electronic device an amount of liquid to be immediately delivered by the pump, sending a wireless command by the remote electronic device to deliver the amount of liquid to be immediately delivered, displaying on a display device of the remote electronic device the amount of liquid to be immediately delivered by the pump, delivering with the pump the amount of liquid to be immediately delivered after receiving the wireless command from the remote electronic device, periodically sending wireless commands by the pump to the remote electronic device of delivery information when the pump is delivering the amount of liquid to be immediately delivered, the delivery information corresponding to incremental quantities of the amount of liquid that has been delivered by the liquid infusion pump, and controlling the display device of the remote electronic device to incrementally count down from the amount of liquid to be immediately delivered based on the delivery information periodically sent by the pump.

A method of determining active insulin in a user taking insulin via an ambulatory infusion pump may comprise receiving delivery information from the pump corresponding to insulin delivered to the user via the pump, computing from the delivery information active insulin in the user by adding together amounts of insulin delivered by the pump over a time period, and displaying the active insulin via a display device.

A method for determining a drug bolus for a user via an electronic device including an on-board glucose meter and a display may comprise determining a first bolus amount based on blood glucose measurements made by the on-board glucose meter, selecting food items for a meal or snack from a food database on-board the electronic device, automatically computing carbohydrate values of each selected food item, automatically determining a total carbohydrate value corresponding to a sum of carbohydrate values of each selected food item, determining a second bolus amount based on the total carbohydrate value, determining a third bolus amount based on health information entered by the user and corresponding to health activities or conditions of the user, and determining a total recommended bolus amount based on the first, second and third bolus amounts.

The method may further comprise delivering a drug bolus to the user in the amount of the total recommended bolus amount.

BRIEF DESCRIPTION OF THE DRAWINGS

FIGS. 10A-10C show a flowchart of one illustrative embodiment of a bolus advice process carried by the remote electronic device.

FIG. 13 shows a graphic representation of one illustrative embodiment of a bolus advice display screen produced by the process of FIGS. 10A-19C.

DETAILED DESCRIPTION

For the purposes of promoting an understanding of the principles of the invention, reference will now be made to a number of illustrative embodiments shown in the attached drawings and specific language will be used to describe the same.

The following co-pending patent applications are incorporated herein by reference: PCT Patent Application No. PCT/US2008/066288, entitled APPARATUS AND METHOD FOR REMOTELY CONTROLLING AN AMBULATORY MEDICAL DEVICE; PCT Patent Application No. PCT/US2008/066262, entitled COMBINATION COMMUNICATION DEVICE AND MEDICAL DEVICE FOR COMMUNICATING WIRELESSLY WITH A REMOTE MEDICAL DEVICE; PCT Patent Application No. PCT/US2008/066267, entitled LIQUID INFUSION PUMP; PCT Patent Application No. PCT/US2008/066299, entitled USER INTERFACE FEATURES FOR AN ELECTRONIC DEVICE; PCT Patent Application No. PCT/US2008/066247, entitled METHOD FOR PAIRING AND AUTHENTICATING ONE OR MORE MEDICAL DEVICES AND ONE OR MORE REMOTE ELECTRONIC DEVICES; PCT Patent Application No. PCT/US2008/066248, entitled DEVICE AND METHODS FOR OPTIMIZING COMMUNICATIONS BETWEEN A MEDICAL DEVICE AND A REMOTE ELECTRONIC DEVICE; and U.S. Provisional Patent Application Ser. No. 61/130,855, entitled DEVICE AND METHODS FOR OPTIMIZING COMMUNICATIONS BETWEEN AN ELECTRONIC DEVICE AND A MEDICAL DEVICE.

Figure 1:
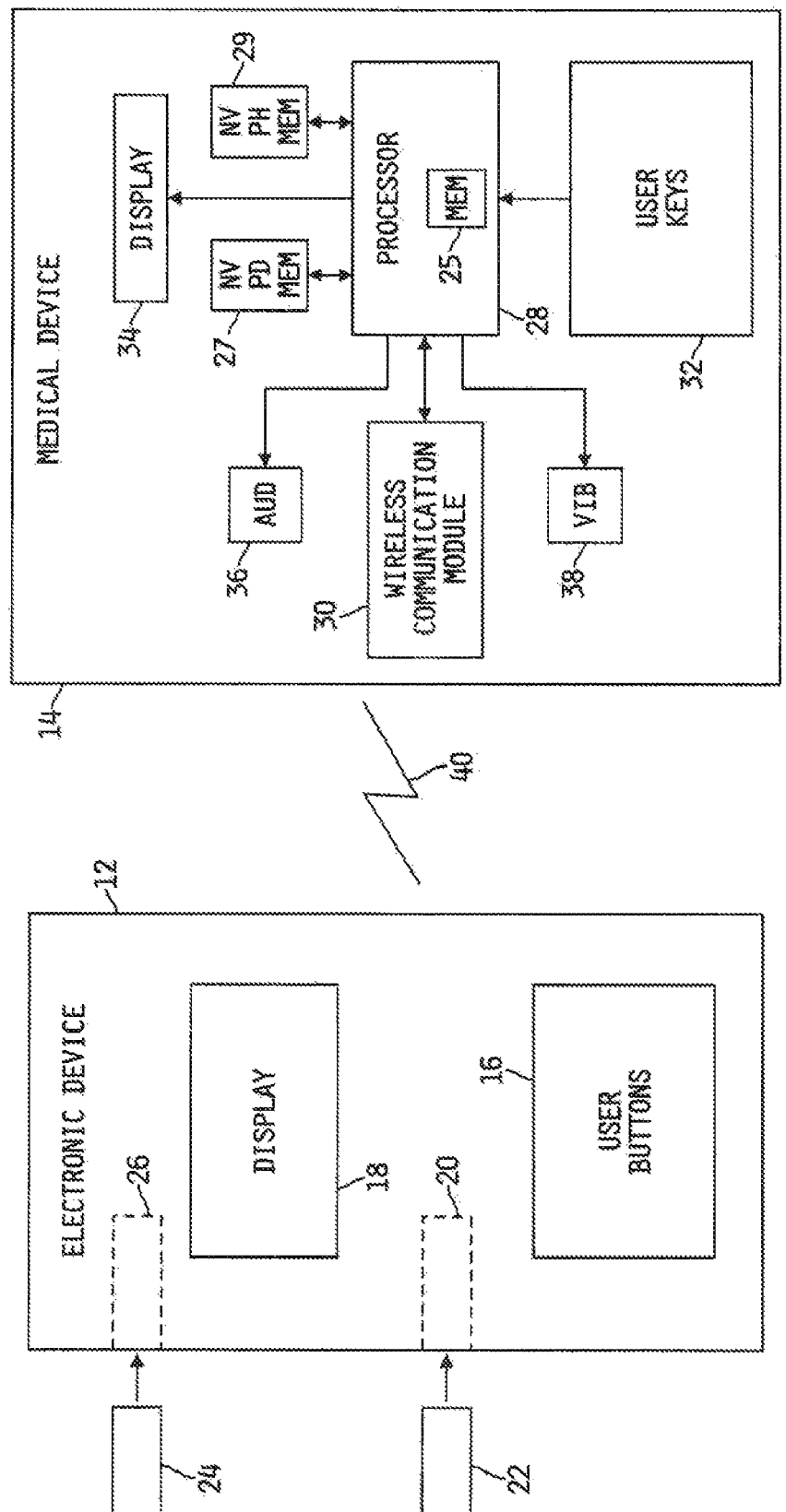
FIG. 1 shows a block diagram of one illustrative embodiment of a wireless communication system including a medical device and a remote electronic device that are both configured to wirelessly communicate with each other.

Referring now to FIG. 1, a block diagram is shown of one illustrative embodiment of a wireless communication system 10 including a remote electronic device 12 and medical device 14 that are both configured to wirelessly communicate with each other. The remote electronic device 12 has a housing through which a user button section 16 extends. In one embodiment, the user button section 16 defines a number of user buttons, keys or switches that may be manually manipulated by a user to provide input to the remote electronic device 12. A visual display unit 18 is carried by the housing of the electronic device 12, and in one embodiment the visual display unit 18 is provided in the form of a conventional liquid crystal display (LCD), although this disclosure contemplates using other conventional display units. Examples include, but are not limited to, plasma displays, light emitting diode (LED) based displays, vacuum fluorescent (VF) displays, and the like. In any case, the visual display unit 18 is controlled by the electronic device 12 to display information to a user of the device 12. In alternative embodiments, the user button section 16 may be or include one or more touch-sensitive buttons. In this embodiment, one or more touch-sensitive buttons may, but not, form part of the display unit 18.

The electronic device 12 further includes a carrier port 20 that extends into the housing from an opening defined therein. The carrier port 20 is sized to receive therein a sample carrier or strip 22 upon which a liquid sample containing an analyte has been or will be deposited. The electronic device 12 includes electrical circuitry that analyzes the liquid sample deposited on the sample carrier 22, when the sample carrier 22 is received within the carrier port 20, to determine a concentration of the analyte contained in the liquid sample. In one embodiment, the liquid sample is blood and the analyte is glucose. In this embodiment, the sample carrier 22 may is illustratively provided in the form of a glucose test strip, and the electrical circuitry of the electronic device 12 includes conventional circuitry that measures the concentration of glucose in a blood sample deposited on the test strip 22. In alternative embodiments, the liquid sample may be or include other bodily fluids, and the analyte may be any analyte that is contained in a bodily fluid.

In the embodiment illustrated in FIG. 1, the electronic device 12 further includes a conventional data key port 26 that extends into the housing from an opening defined therein. The data key port 26 defines an electrical interface or connector therein that is configured to electrically connect to a complementarily configured electrical interface or connector defined on a conventional data key 24. The data key 24 includes a conventional memory device (not shown) that is electrically connected to the electrical interface or connector defined on the data key 24. The memory device, e.g., ROM key, is electrically connected to the electrical circuitry of the electronic device 12 via the electrical interface defined on the data key 24 and the electrical interface defined in the data key port 26 when the data key 26 is received within the data key port 24. Generally, the memory device of the data key 24 has calibration data stored therein that is specific to a lot or batch of test strips 22, and the electrical circuitry of the electronic device 12 uses the calibration data stored in the memory device of the data key 24 to correct glucose concentration measurements when using a test strip 22 from a corresponding lot or batch of test strips as is known in the art. Typically, each lot or batch of test strips 22 purchased by a user will include a dedicated data key 24 that is to be used when measuring glucose concentration with that lot or batch of strips.

It will be understood that while the carrier port 20, sample carrier 22 and electrical circuitry of the electronic device 12 have been described in one embodiment as being configured to measure the glucose concentration of blood samples deposited on the sample carrier 22, this disclosure contemplates other embodiments in which the carrier port 20, sample carrier 22 and/or electrical circuitry of the electronic device 12 is/are configured to measure other analytes in other liquid samples.

The medical device 14 includes a conventional processor 28 that is electrically connected to a wireless communication circuit 30. The processor 28 includes a conventional memory unit 25 which has stored therein a number of processes in the form of instructions that are executable by the processor 28 to control operation of the medical device 14 and to wirelessly communicate with the electronic device 12. In the illustrated embodiment, the medical device 14 further includes conventional non-volatile memory units 27 and 29. In one embodiment, the non-volatile memory unit 27 is provided in the form of a conventional ferroelectric random access memory (FRAM) and the non-volatile memory unit 29 is provided in the form of a conventional electrically erasable programmable read only memory (EEPROM), although either memory unit 27, 29 may alternatively be provided in the form of one or more other conventional non-volatile memory units. In any case, the memory units 27 and 29 are each external to the processor 28 and are each electrically connected to the processor 28. In one illustrative embodiment in which the medical device is a drug infusion pump, as will be described in greater detail hereinafter, the memory unit 27 is a pump delivery (PD) memory unit in which the processor 28 stores current pump delivery information, and the memory unit 29 is a pump history (PH) memory unit that has stored therein pump history information, e.g., in the form of event records each corresponding to an operational event of the pump 14. The medical device 14 further includes a wireless communication circuit 30 that is configured to communicate wirelessly with a similar wireless communication module of the remote electronic device 12 via a wireless communication link 40 in a conventional manner. In one embodiment, as will be illustrated by example throughout this disclosure, the wireless communication circuit 30 and the wireless communication module of the electronic device 12 are both conventional BlueTooth® modules configured to wirelessly communicate according to a conventional BlueTooth® communication protocol. It will be understood, however, that the wireless communication circuit or module 30 and the wireless communication module of the electronic device 12 may alternatively be configured to wirelessly communicate according to one or more other communication protocols.

The medical device 14 illustratively includes a housing through which a number of user keys 32 extend. The user keys 32 may be provided in the form of any number of user selectable buttons, keys or switches that are electrically connected to the processor 28. The medical device 14 further includes a visual display unit 34 that is carried by the housing and that is electrically connected to the processor 28. The visual display unit 34 may be, for example, a conventional liquid crystal display (LCD), plasma displays, light emitting diode (LED) based display, vacuum fluorescent (VF) display, or the like. The visual display unit 34 is controlled by the processor 28 to display information to a user of the medical device 14. In alternative embodiments, the user keys 32 may be or include one or more touch-sensitive buttons. In this embodiment, one or more touch-sensitive buttons may, but not, form part of the display unit 34.

The processor 28 of the medical device 14 is further electrically connected to a conventional audible indication device 36 and to a conventional vibratory device 38. The processor 28 is generally operable to control the audible indication device 36 and the vibratory device 38 to produce one or more audible sounds and/or vibrations respectively to notify the user of various operational aspects of the medical device 14 and to also notify the user of any alarm and/or warning conditions associated with the medical device 14. In alternative embodiments, the medical device 14 may not include a display device 34 and/or user keys 32. In some such embodiments, the medical device 14 may include one or more visual indicators for conveying information to a user. Examples of such visual indicators may include, but should not be limited to, one or more lamps, one or more light emitting diodes (LEDs), or the like.

In one illustrative embodiment, the medical device 14 is an ambulatory medical device. Examples of ambulatory medical devices include, but are not limited to, an implantable liquid delivery pump or a non-implantable liquid delivery pump, such as a drug infusion pump, an implantable or non-implantable body condition sensor or sensor system, or the like. In embodiments in which the electronic device 14 is a medication delivery pump, the medication delivered by such a pump may be or include, but should not be limited to, insulin or other conventional blood glucose modifying drug. In alternate embodiments, the liquid delivered by any such a pump may be or include, but should not be limited to, one or a combination of drugs, saline, one or a combination of perfusion fluids, or the like. Throughout this disclosure, the medical device 14 and operations associated with the medical device 14 will be described in the context of an insulin infusion pump, although it will be understood that the medical device 14 may alternatively be or include other medical devices and the following description therefore should not be considered to be limited to an liquid delivery pump generally or to an insulin infusion pump specifically.

Figure 2:
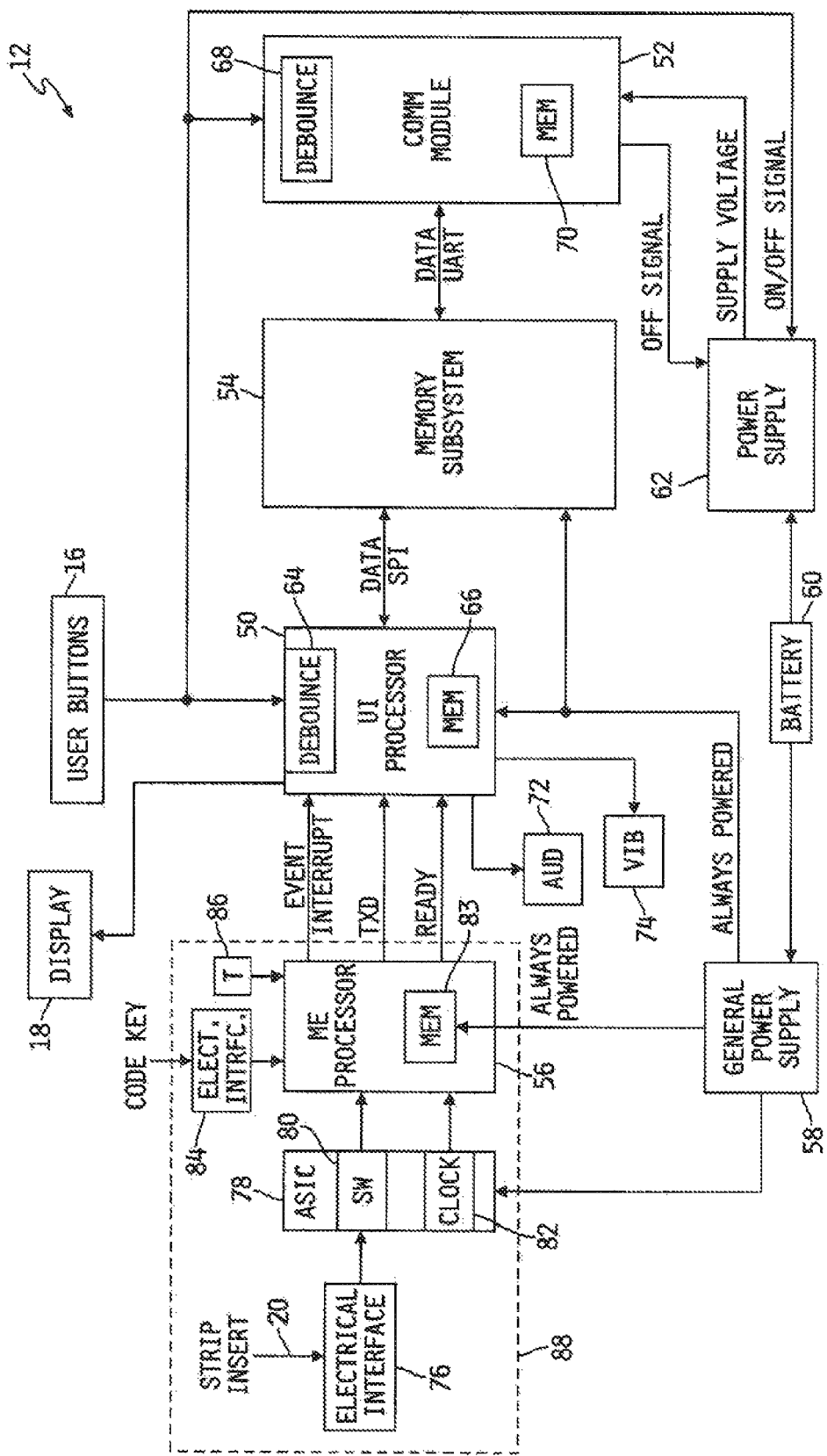
FIG. 2 shows a block diagram schematic of one illustrative embodiment of an electronic circuit that is carried by, and that controls, the remote electronic device of FIG. 1.

Referring now to FIG. 2, a block diagram schematic is shown of one illustrative embodiment of an electronic circuit that is carried by, and that controls, the remote electronic device 12 of FIG. 1. In the illustrated embodiment, the electronic circuit includes four modules with separate and distinct functional responsibilities. For example, the electronic circuit includes a User Interface (UI) processor 50 that is the main controller of the electronic device 12. In addition to processing all aspects of the user interfaces 16, 18, it is the origination and destination of all data communicated from and to the insulin infusion pump 14. As will be described in greater detail herein, the UI processor 50 has no control over operation of the wireless communication circuit of the remote electronic device 12. The UI processor 50 operates according to a UI clock signal that is generated internally to the UI processor 50. The UI processor 50 includes a memory unit 66 having instructions stored therein that are executable by the UI processor 50 to control operations associated with the remote electronic device 12. In one illustrative embodiment, the UI processor 50 is a UPD70F3719GC 32-bit microcontroller that is commercially available from NEC Electronics America of Santa Clara, Calif., although this disclosure contemplates other implementations of the UI processor 50.

The electronic circuit of FIG. 2 further includes a wireless communication circuit 52 that is exclusively responsible for the control of all wireless communications with one or more external electronic devices but that does not control any other operations associated with the electronic device 12. The wireless communication circuit 52 operates from a clock signal that is generated internally to the wireless communication circuit 52 and that is not synchronized to the UI clock signal from which the UI processor 60 operates. Operation of the wireless communication circuit 52 is therefore asynchronous with respect to the operation of the UI processor 60. In one illustrative embodiment, the wireless communication circuit 52 is provided in the form of a conventional BlueTooth® telemetry module that includes a conventional processor and a memory unit 70, and that further includes conventional wireless communication hardware such as a suitable antenna. The memory unit 70 illustratively has stored therein instructions that are executable by the processor of the wireless communication circuit 52 to exclusively control of all wireless communications with external devices, such as the insulin infusion pump 14. In one illustrative embodiment, the wireless communication circuit 52 is a BC419143B BlueCore™ 4-Flash Plug-n-Go™ single chip BlueTooth® radio and baseband integrated circuit for BlueTooth® 2.4 GHz systems that is commercially available from CSR of Richardson, Tex., although this disclosure contemplates other implementations of the wireless communication circuit 52. Alternatively, as described hereinabove, this disclosure contemplates embodiments in which the wireless communication module 52 is configured for wirelessly communication according to wireless communication protocols other than BlueTooth®.

As illustrated in FIG. 2, the UI processor 50 and the wireless communication module 52 each include debounce circuitry 64 and 68 respectively that is electrically connected to the user buttons 16. The debounce circuitry 64, 68 is conventional in that it reduces the sensitivity of the processors 50 and 52 to spurious switching events associated with the user buttons 16, thereby increasing the likelihood that only actual button presses are detected by the processors 50 and 52.

The electronic circuit illustrated in FIG. 2 further includes a memory subsystem 54 that is electrically connected to the UI processor 50 and also to the wireless communication circuit 52. The memory subsystem 54 is generally operable to store, at least temporarily, data moving between the UI processor 50 and the wireless communication circuit 52. Data communication between the memory subsystem 54 and the UI processor 50 is illustratively carried out via a serial peripheral interface, SPI, in which case the transfer of data between the memory subsystem 54 and the UI processor 50 is synchronous with a data transfer clock, SCLK, of the UI processor 50. Illustratively, data communication between the memory subsystem 54 and the wireless communication circuit 52 is carried out via a universal asynchronous receiver/transmitter (UART) interface, in which case the transfer of data between the memory subsystem 54 and the wireless communication circuit 52 is asynchronous. In some alternative embodiments, the data transfer interfaces may be interchanged such that data transfer between the memory subsystem 54 and the UI processor 50 is asynchronous and data transfer between the memory subsystem 54 and the wireless communication circuit 52 is synchronous.

The memory subsystem 54 temporarily stores data moving between the UI processor 60 and the wireless communication circuit 52. In some embodiments, the memory subsystem 54 does not control other circuitry, and in some such embodiments the memory subsystem 54 may be provided in the form of a conventional memory device. In other embodiments in which the memory subsystem 54 does or does not control other circuitry, the memory subsystem 54 may be provided in the form of a conventional processor that is configured to operate as a Dual-Port RAM (DPR) processor. In such embodiments, the DPR processor 54 operates from a clock signal that is separate from the UI clock signal from which the UI processor 60 operates. In one illustrative embodiment, such a DPR processor 54 is a MC9S08GT16A 8-bit microcontroller unit that is commercially available from Freescale Semiconductor, Inc. of Austin, Tex., although this disclosure contemplates other implementations of the memory subsystem 54 that is provided in the form of a conventional processor configured as a DPR processor 54.

The electronic circuit illustrated in FIG. 2 further includes a Measurement Engine (ME) processor 56 that controls analyte concentration measurements of liquid samples contained on test elements 22, e.g., blood glucose measurements, and that reports the analyte concentration measurement results to the UI processor 50. The ME processor 56 includes a memory unit 83 having instructions stored therein that are executable by the ME processor 56 to control analyte measurement operations. The ME processor 56 operates from an internally generated clock signal that is separate from the clock signal from which the UI processor 50 operates. The ME processor 56 is electrically connected to the UI processor 50 via an Event Interrupt line, TXD (data transmission) line and a Ready line. The Event Interrupt line is illustratively used by the ME processor 56 to notify the UI processor of analyte measurement events, such as a strip insert event in which a user initiates an analyte measurement. The TXD line is used by the ME processor 56 to transmit analyte measurement data to the UI processor 50 for display on the display unit 18, for storage thereof in a history database and/or for use in conducting other operations. The Ready line is used by the ME processor 56 to notify the UI processor 50 of the operational state, e.g., measuring or not measuring analyte concentration, of the ME processor. In one illustrative embodiment, the ME processor 56 is a MSP430T2AIPEG mixed-signal microcontroller unit that is commercially available from Texas Instruments, Inc. of Dallas, Tex., although this disclosure contemplates other implementations of the ME processor 56.

As illustrated in FIG. 2, the ME processor 56, along with other electrical components, form an analyte measuring facility 88, e.g., a glucose meter. In addition to the ME processor 56, the analyte measuring facility 88 further includes an application specific integrated circuit (ASIC) 78 that is electrically connected to the ME processor 56 and also to an electrical interface 76 within the carrier port 20. In one illustrative embodiment, when a sample carrier 22, e.g., a glucose test strip, is inserted into the carrier port 20, electrical contacts on the sample carrier 22 contact the electrical interface 76 to thereby electrically connect the sample carrier 22 to the ASIC 78. A switch 80 contained in the ASIC is triggered by insertion of the carrier 22 into the carrier port 20, and an output of the switch 80 thus notifies the ME processor 56 of insertion of a carrier 22 into the carrier port 20. The ASIC 78 further illustratively includes a clock circuit 82 that is programmable for a number of different functions. For example, the clock circuit 82 may be programmed to generate a signal to automatically turn on, e.g., power up, the device 12 at one or more programmable times. As another example, the clock circuit 82 may be programmed to generate a signal corresponding to one or more reminders. Other examples will occur to those skilled in the art, and such other examples are contemplated by this disclosure. In any case, the signal generated by the clock circuit 82 is provided to the ME processor 56, and the ME processor 56 is responsive to the receipt of this signal to power up from a sleep state if the ME processor 56 is in such a sleep state, and to produce an event interrupt signal on the Event Interrupt line. The event interrupt signal is received by the UI processor 50, which then powers up from a sleep state if the UI processor 50 is in such a sleep state, and/or generates an audible or visible reminder corresponding to any reminder time programmed in the clock circuit 82.

As illustrated in FIG. 2, the analyte measuring facility 88 further includes another electrical interface 84 that is positioned within the code key port 26. Illustratively, when a code key 24 is received within the code key port 26, electrical contacts on the code key 24 electrically connect with the electrical interface 84 so that the ME processor 56 may read the calibration information stored in the memory device of the code key 24. The analyte measuring facility 88 further includes a temperature sensor 86 that is electrically connected to the ME processor 56. In one illustrative embodiment, the temperature sensor 86 is provided in the form of a conventional thermistor, although this disclosure contemplates other embodiments in which the temperature sensor 88 may be or include one or more other conventional temperature sensors. In any case, the ME processor 56 is operable to receive a temperature signal from the temperature sensor 86 that corresponds to an operating temperature of the analyte measuring facility. In one illustrative embodiment, the memory 83 has instructions stored therein that are executable by the ME processor 56 to disable, i.e., not conduct, analysis of an analyte containing sample if the temperature signal produced by the temperature sensor 86 indicates that the temperature of the analyte measuring facility 88 is less than a threshold temperature. In such cases, the ME processor 56 is further operable, pursuant to the instructions stored in the memory 83, to inform the UI processor 50 that the analyte measuring facility is so disabled, and the UI processor 50 is operable, pursuant to instructions stored in the memory unit 66, to control the display device 18 to display a message indicating that the temperature is too low to conduct analyte concentration measurements.

The electronic circuit illustrated in FIG. 2 further includes a general power supply 58 that provides a supply voltage to the ASIC 78, the ME processor 56, the UI processor 50 and the memory subsystem 54 on a continuous basis. The supply voltage is derived by the general power supply circuit 58 from one or a series or parallel combination of rechargeable or non-rechargeable batteries (BATTERY) 60.

A dedicated power supply 62 provides a supply voltage, which is also derived from the one or series or parallel combination of rechargeable or non-rechargeable batteries (BATTERY) 60, to the wireless communication module 52. The power supply 62 receives one control input from the user buttons 16, and in the illustrated embodiment the power supply 62 may be powered on and off via one or a combination of the user buttons 16 via the one control input. The power supply 62 also receives another control input from the wireless communication circuit 52, and in the illustrated embodiment the power supply 62 may be turned off by the wireless communication circuit 52 via the other control input.

In addition to the display 18, the UI processor 50 is electrically connected to a conventional audible indication device 72 and also to a conventional vibratory device 74. The UI processor 50 is generally operable to control the audible indication device 72 and the vibratory device 74 to produce one or more audible sounds and/or vibrations respectively to provide for the capability of the device 12 to produce corresponding audible and/or tactile notifications, i.e., alarms or the like. In one embodiment, the audible indication device 72 is a tone generator that produces a beep or other tone when activated, although the audible indication device 72 may alternatively or additionally be or include one or more other conventional audible indication devices.

Figure 3:
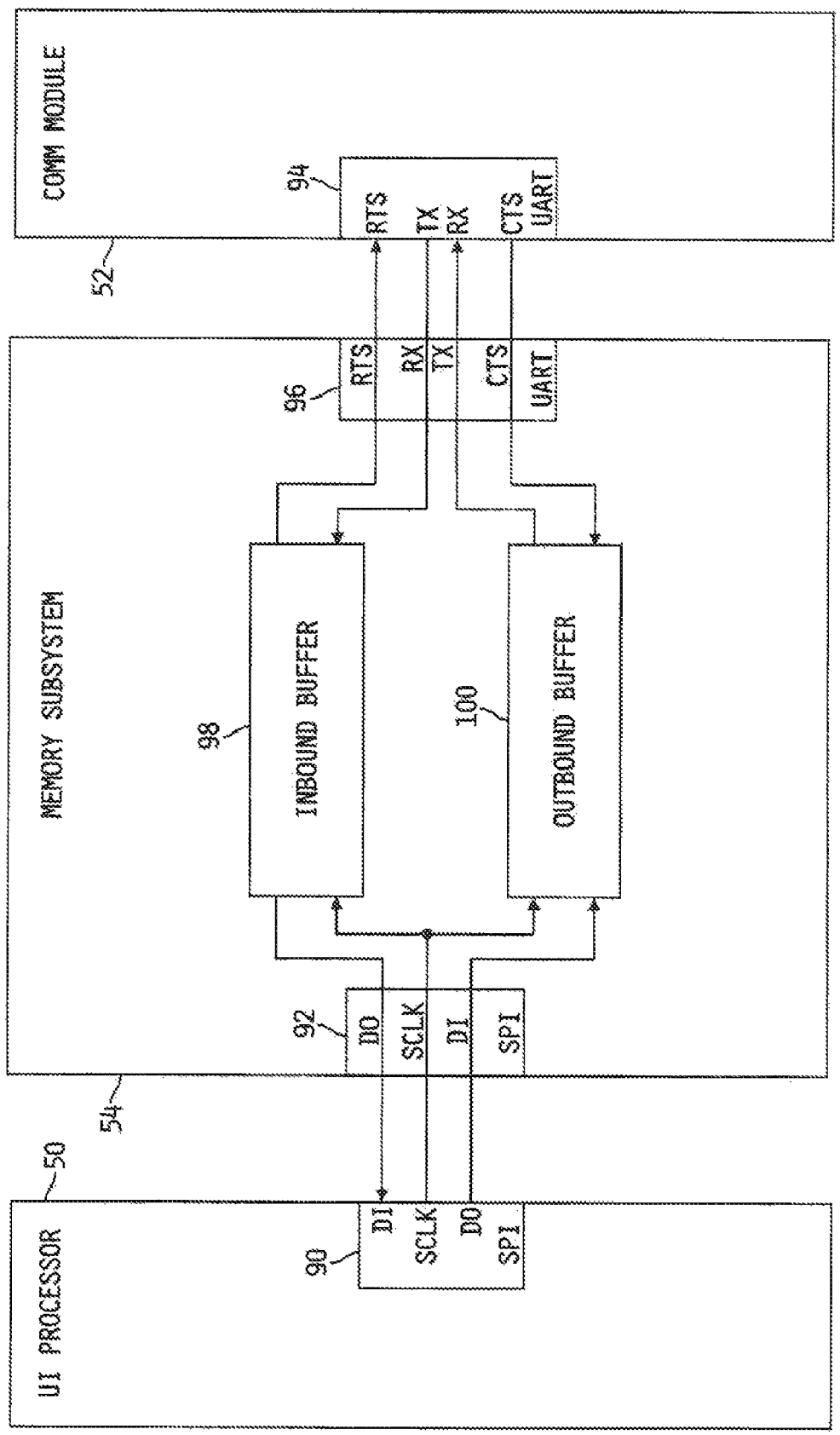
FIG. 3 shows a block diagram schematic of some of the details of one illustrative embodiment of the memory subsystem of the remote electronic device of FIG. 2.

Generally, the memory subsystem 54 acts as an independent repository of data packets moving between the UI processor 50 and the wireless communication circuit 52. Referring to FIG. 3, a block diagram of some of the details of the memory subsystem 54 is shown along with electrical connections to the UI processor 50 and to the wireless communication circuit 52. In the illustrated embodiment, the memory subsystem 54 is provided in the form of a DPR processor as described above, and FIG. 3 will be described in this context, although it will be understood that the memory subsystem 54 may alternatively be provided in other forms as described above.

In the embodiment illustrated in FIG. 3, one of the dual ports of the DPR processor 54 is a serial peripheral interface (SPI) port 92 that is electrically connected to a serial peripheral interface port 90 of the UI processor 50 via a conventional serial communications interface. The serial communications interface operates from a serial clock signal, SCLK, (e.g., 125 kHz) that is derived from the UI clock signal. Transfer of inbound and outbound data between the SPI port 90 of the UI processor 50 and the SPI port 92 of the DPR processor 54 is controlled by the UI processor 50 using the serial clock signal, SCLK, so that data transfer between the two processors 50, 54 is synchronized.

The other of the dual ports of the DPR processor 54 is a universal asynchronous receiver/transmitter (UART) port 96 that is electrically connected to a UART port 94 of the wireless communication circuit 52 via a conventional asynchronous interface. Transfer of inbound and outbound data packets between the UART port 94 of the wireless communication circuit 52 and the UART port 96 of the DPR processor 54 (e.g., at 150 kbps) is controlled by the wireless communication circuit 52, and takes place asynchronously with respect to the transfer of inbound and outbound data between the SPI port of the UI processor 50 and the DRP processor 54.

The DPR processor 54 has an inbound data buffer 98 and an outbound data buffer 100 that are each accessible by the SPI and UART ports 92 and 96 respectively of the DPR processor 54. The UART port 96 of the DPR processor 54 includes conventional clear to send (CTS) and ready to send (RTS) lines. The CTS line is monitored by the DPR processor 54 and the RTS line is monitored by the wireless communication circuit 52. The DPR processor 54 deactivates the UART RTS line whenever the inbound data buffer 100 is full, and otherwise activates the UART RTS line. The wireless communication circuit 52 activates the UART CTS line whenever the UART port of the wireless communication circuit 52 is requesting data, and otherwise deactivates the UART CTS line.

When data is to be sent by the UI processor 50 to an external device or system, e.g., the insulin infusion pump 14, the UI processor 50 first requests the state of the outbound data buffer 100 of the DPR processor 54. If the DPR processor 54 answers that its outbound data buffer 100 is "not full," the UI processor 50 transfers the data, or as much of the data as possible, to the outbound data buffer 100 of the DPR processor 54 via the data out (DO) line of the SPI port 90 at a rate determined by SCLK. If the DPR processor 54 instead answers that the outbound data buffer 100 is "full," the UI processor 50 waits for a time interval and then repeats the process of requesting the state of the outbound data buffer 100, etc.

Periodically with respect to the clock signal of the wireless communication circuit 52 and asynchronously with respect to the SCLK signal, the wireless communication circuit 52 requests data from the DPR processor 54 by activating the UART CTS line of the DPR processor 54. As long as the outbound data buffer 100 of the DPR processor 54 is empty, the wireless communication circuit 52 continues to periodically activate the UART CTS line. If the UART CTS line is active and the outbound data buffer 100 of the DPR processor 54 is not empty, the wireless communication circuit 52 retrieves the data from the outbound data buffer 100 of the DPR processor 54 via the RX line of the UART port 96. The DPR processor 54 illustratively transfers the data stored in its outbound data buffer 100 to its UART port 96 in a first received to last received order until the outbound data buffer 100 has been emptied or until the wireless communication circuit 52 deactivates the UART CTS line. The wireless communication circuit 52 then incorporates the data retrieved from the outbound data buffer 100 of the DPR processor 52, via the data UART, into to the wireless communication protocol structure, and wirelessly transmits the incorporated data via conventional wireless signal transmission circuitry contained within the wireless communication module 52. The wireless communication circuit 52 does not process, interpret or alter the contents of the data retrieved from the outbound data buffer 100 of the DPR processor 54, nor does it make any decisions or execute any steps based on the contents of the data. Rather, the wireless communication circuit 52 treats all such data the same, regardless of its contents, by incorporating the data into a predefined wireless communication protocol structure, e.g., BlueTooth® protocol structure, and then wirelessly transmitting the incorporated data using the predefined wireless communication protocol. Information transferred by the UI processor 50 to the memory subsystem 54, and then from the memory subsystem 54 to the wireless communication circuit 52 for wireless transmission to another electronic device is thus referred to as outbound information or data.

Inbound wireless signal transmissions from external devices or systems, e.g., the insulin infusion pump 14, are received by the wireless communication circuit 52 via conventional wireless signal receiving circuitry of the wireless communication circuit 52. The wireless communication circuit 52 first isolates the inbound data from the wireless communication protocol structure, and then checks the status of the UART RTS line of the DPR processor 54. If the RTS line is activated, indicating that the inbound data buffer 98 of the DPR processor 54 is not full, the wireless communication circuit 52 sends the isolated data, or as much if the data as possible, to the UART port 96 of the DPR processor 54. The DPR processor 54 then places the data received at the UART port 96 into the inbound data buffer 98 of the DPR processor 54. If the UART RTS line is deactivated, indicating that the inbound data buffer 98 of the DPR processor 54 is full, the wireless communication circuit 52 waits for a time interval before rechecking the state of the UART RTS line.

Periodically, and asynchronously with respect to the operation of the wireless communication circuit 52, the UI processor 50 requests the state of the inbound data buffer 98 of the DPR processor 54 via the data in (DI) line of the SPI port 90. As long as the DPR processor 54 answers that the inbound data buffer 98 is empty, the UI processor 50 continues to periodically request the state of the inbound data buffer 98. If the DPR processor 54 answers that the inbound data buffer 98 of the DPR processor 54 contains data, the UI processor 50 retrieves the data from the inbound data buffer 98 of the DPR processor 52 via the data in (DI) line of the SPI port 90 using the SCLK signal, and then processes the data according to its contents. "Checking" the inbound and/or outbound data buffer 98, 100 of the DPR processor 54 by the wireless communication circuit 52 and/or UI processor 50, as this term may be used hereinafter, will generally refer to the process just described in the preceding several paragraphs. While FIGS. 2 and 3 illustrate an embodiment in which the interface between the UI processor 50 and the memory subsystem 54 is a synchronous interface and the interface between the wireless communication circuit 52 and the memory subsystem 54 is an asynchronous interface, this disclosure contemplates alternative embodiments in which the interface between the UI processor 50 and the memory subsystem 54 is an asynchronous interface and the interface between the wireless communication circuit 52 and the memory subsystem 54 is an synchronous interface or in which both interfaces are asynchronous or synchronous interfaces. In any case, it should be apparent that the UI processor 50 at all times operates independently and asynchronously with respect to the operation of the wireless communication circuit 52, and the wireless communication circuit 52 operates independently and asynchronously with respect to the operation of the UI processor 50 and also with respect to the operation of the DPR processor 54.

The UI processor 50 controls the display 18 of the electronic device 12 to indicate the connection status of the wireless communication module 52 relative to the wireless telemetry system of the insulin infusion pump 14. Upon power up of the electronic device 12, following activation of the power supply 62 via the user buttons 16 after being deactivated and under certain other operating conditions that will be described in greater detail hereinafter, the UI processor 50 attempts to establish a wireless connection with the insulin infusion pump 14. While a wireless connection is not established between the electronic device 12 and the insulin infusion pump 14, the UI processor 50 controls the display 18 to display a flashing (or fixed) icon to indicate that no wireless connection exists between the electronic device 12 and the insulin infusion pump 14. The UI processor 50 independently controls the display 18 in this manner without any information provided by the wireless, communication module 52. The UI processor 50 then initiates establishment of a wireless connection between the remote electronic device 12 and the insulin infusion pump 14 by placing a message into the data buffer 100 of the outbound port of the memory subsystem 54, as described above. In this case, the message includes a wireless connection request, e.g., in the form of a command to transmit an acknowledgement response back to the electronic device 12. The wireless communication circuit 52 then transmits this message as described above. If the insulin infusion pump 14 is within range, the insulin infusion pump 14 receives the message and responds to the wireless connection request by wirelessly transmitting a message that includes an acknowledgement response. If the transmitted message is received by the electronic device 12, the wireless communication circuit 52 is operable as described above to isolate the message from the wireless communication protocol structure and to place the message in the data buffer 98 of the inbound port of the memory subsystem 54. The UI processor 50 then retrieves the message from the inbound port of the memory subsystem 54, processes the message to determine whether it contains an acknowledgement response. If the message contains an acknowledgement response, the UI processor 50 interprets this as indicating that a wireless connection is now established between the electronic device 12 and the insulin infusion pump 14, and controls the display device 18 to display a fixed (or flashing) icon to indicate that a wireless connection is established between the electronic device 12 and the insulin infusion pump 14. The electronic device 12 periodically transmits a wireless connection status message to the infusion pump 14 in the above fashion at regular intervals. As long as the insulin infusion pump 14 responds as just described, the UI processor 50 controls the display 18 to display the fixed (or flashing) icon to indicate that a wireless connection exists between the electronic device 12 and the insulin infusion pump 14. If the UI processor 50 does not receive such a response within a predefined time period following storage of the acknowledgement response in the memory subsystem 52, the UI processor 50 controls the display 18 to display a flashing (or fixed) icon indicating that the wireless connection between the electronic device 12 and the insulin infusion pump 14 does not exist or no longer exists.

In the illustrated embodiment the power supply 62 is generally powered on as long as the wireless communication circuit 52 is communicating with either or both of the UI processor 50 or the insulin infusion pump 14, unless otherwise powered off manually by a user via the user buttons 16 or automatically by the wireless communication circuit 52. For example, the power supply 62 may be completely powered down, i.e., turned off, from any state via a simultaneous or sequential user press of a number of the user buttons 16. The power supply 62 remains in the completely powered down state until the user again presses the simultaneous or sequential number of the user buttons 16 or a different simultaneous or sequential user press of a number of the user buttons, or if the user powers down the electronic device 12 and then powers back up the electronic device 12.

While the power supply 62 is on and supplying the supply voltage to the wireless communication circuit 52, the wireless communication circuit 52 is responsive to a number of different events to transition itself into, and out of, any of a plurality of different low power states, and to also turn off the power supply 62 after being in a lowest power sleep state for a predefined time period of inactivity. For example, when in a fully powered "awake" state, the wireless communication circuit 52 is operable to periodically, e.g., every 100-200 milliseconds, check the outbound data buffer 100 of the memory subsystem 54 as described above. As another example, each time the wireless communication circuit 52 finds data to be sent in the outbound data buffer 100 of the memory subsystem 54, the wireless communication circuit 52 incorporates the data into the predetermined wireless communication protocol structure, and wirelessly transmits corresponding signals to the insulin infusion pump 14 as described above. The wireless communication circuit 52 transitions to a first low power state if it fails to find data in the outbound data buffer 100 of the memory subsystem 54 when a predefined time period elapses since last finding data in the outbound data buffer 100. Thereafter, the wireless communication circuit 52 transitions to successively lower power states as successively longer time periods elapse since last finding data in the outbound data buffer 100. The number of different power states generally range between full (100%) power and a lowest power "deep sleep" state, and may include any number of reduced power states between these two extremes. When in the lowest power "deep sleep" state, the wireless communication circuit 52 periodically, e.g., every 400 milliseconds, wakes up to a "UART only" state, in which the wireless communication circuit 52 has sufficient power to check the status of the outbound data buffer 100 of the memory subsystem 54 via the data UART line. If the outbound data buffer 100 of the memory subsystem 54 has data stored therein, the wireless communication circuit 52 wakes up to a full power state to service the data. If the outbound data buffer 100 of the memory subsystem 54 has no data stored therein, the wireless communication circuit 52 transitions back to the lowest power "deep sleep" state. After being in the lowest power sleep state for a predefined period of time of inactivity, the wireless communication circuit 52 sends a control signal to the power supply 62 that causes the power supply 62 to turn off. As a further example, the wireless communication circuit 52 directly monitors activity of the user buttons 16 via the debounce circuitry 68, and when the wireless communication circuit 52 detects user press of the ON button, the wireless communication processor transitions itself from any of the lower power states to the full power state. Thus, in the lowest power "deep sleep" state, the wireless communication circuit 52 must be capable of monitoring at least the ON button of the user buttons 16. Similarly, when the wireless communication circuit 52 detects user press of the OFF button, the wireless communication circuit 52 transitions itself from any of the power states to the lowest power "deep sleep" state.

When a wireless connection is established between the electronic device 12 and the insulin infusion pump 14, and the UI processor 50 determines that the wireless connection should be terminated, the UI processor 50 stores a message in the outbound data buffer 100 of the memory subsystem 54 that contains a connection termination request. When the wireless communication circuit 52 thereafter finds the message in the outbound data buffer 100 of the memory subsystem 54, the wireless communication circuit 52 incorporates the message into the predetermined wireless communication protocol and then transmits the message via its wireless communication circuitry to the insulin infusion pump 14. The insulin infusion pump 14 then wirelessly sends a signal containing a predefined connection termination response back to the remote electronic device 12. Subsequently the processor 28 instructs the wireless communication circuit 30 to orderly terminate communications or connections with the wireless communications circuit 52' that may be specific to the predetermined wireless communications protocol. When the wireless connection is terminated in this manner, the wireless communication circuit 52 is operable to periodically, but asynchronously with respect to operation of the UI processor 50, check the outbound data buffer 100 of the memory subsystem 54. If no data resides in the outbound data buffer 100, the wireless communication circuit 52 successively enters lower power sleep states or modes as described above. If, however, the wireless communication circuit 52 finds data in the outbound data buffer 100 of the memory subsystem 54, the wireless communication circuit 52 attempts to establish (or re-establish) a wireless connection with the wireless communication circuit 30 of the insulin infusion pump 14 as described above.

If, after a predefined or programmed number of attempts and/or elapsed time, no wireless connection can be established between the wireless communication circuit 52 and the wireless communication circuit 30, the wireless communication circuit 52 illustratively clears the outbound data buffer 100 of the memory subsystem 54. Alternatively, the UI processor 50 may clear the outbound data buffer 100 if it determines that data exists in the outbound data buffer 100 after some time period has elapsed since storing the wireless communication message in the outbound data buffer 100 or after some time period has elapsed after determining, based on failure to receive acknowledgements from the insulin infusion pump 14, that a wireless connection between the remote electronic device 12 and the insulin infusion pump 14 no longer exists. In any case, with the outbound data buffer 100 of the memory subsystem 54 empty, the wireless communication circuit 52 successively enters lower power sleep states or modes as described above.

In the event of a lost wireless connection between the remote electronic device 12 and the insulin infusion pump 14, the wireless communication circuit 52 is operable in one embodiment to turn off its wireless transmission circuitry and to transition to a low power state if it fails to find data in the outbound data buffer 100 of the memory subsystem 54 since last finding data in the outbound data buffer 100. Because the wireless connection is lost, the UI processor 50 will no longer receive acknowledgements from the insulin infusion pump 14 and will therefore cease to store messages in the outbound data buffer 100 of the memory subsystem 54. However, a message, or at least part of a message, may reside within the outbound data buffer 100 when the wireless connection is lost. In this case, after a predefined or programmed number of attempts and/or after a predefined or programmed elapsed time, no wireless connection can be established with the insulin infusion pump 14, the wireless communication circuit 52 illustratively clears the outbound data buffer 100 of the memory subsystem 54. Alternatively, the UI processor 50 may clear the outbound data buffer 100 if it determines that data exists in the outbound data buffer 100 after some time period has elapsed since last storing a message in the outbound data buffer 100 or after some time period has elapsed after determining, based on failure to receive acknowledgements from the insulin infusion pump 14, that a wireless connection between the devices 12 and 14 no longer exists. In any case, with the outbound data buffer 100 of the memory subsystem 54 empty, the wireless communication circuit 52 successively enters lower power sleep states or modes as described above.

In one illustrative embodiment, the UI processor 50 and the processor 28 of the insulin infusion pump 14 may use scheduled messages and internal timers to control determinations by each of whether a wireless connection between the remote electronic device 50 and the insulin infusion pump 14 exists. For example, during information exchange between the electronic device 12 and the insulin infusion pump 14, the UI processor 50 is operable to periodically, e.g., every 100 milliseconds, transfer a message to the outbound data buffer 100 of the memory subsystem 54 and to reset an internal timer circuit. The wireless communication circuit 52 asynchronously retrieves the message from the outbound data buffer 100 of the memory subsystem 54 and transmits the message to the insulin infusion pump 14 as described above. The insulin infusion pump 14 is responsive to receipt of the message to immediately transmit a message back to the electronic device 12 that contains an acknowledgement. The message transmitted by the insulin infusion pump 14 is received and unpacked from the wireless communication protocol by the wireless communication circuit 52, and then stored by the wireless communication circuit 52 in the inbound data buffer 98 of the memory subsystem 54. The UI processor 50 then retrieves the message from the inbound data buffer 98 of the memory subsystem 54 and processes the message to determine whether it contains an acknowledgement. As long as an acknowledgement is received by the UI processor 50 in this manner before the next scheduled transfer of a message to the outbound data buffer 100 of the memory subsystem 54, the UI processor 50 resets its internal timer circuit when transferring the next message to the memory subsystem 54. However, if an acknowledgement is not received by the UI processor 50 before the next scheduled transfer of a message to the outbound data buffer 100 of the memory subsystem 54, the UI processor 50 transfers the message to the outbound data buffer 100 of the memory subsystem 54 without resetting its internal timer circuit. If no acknowledgement is received by the UI processor 50 within a predefined or programmed time period, e.g., 1-2 minutes, the internal timer circuit of the UI processor 50 times out and the UI processor 50 stops transferring messages to the outbound data buffer 100 of the memory subsystem 54. The insulin infusion pump 14, in this embodiment, ceases to send acknowledgements back to the remote electronic device 12 after a predefined or programmed time period, e.g., 2 minutes, has passed without receiving a message transmitted by the electronic device 12.

Illustratively, the UI processor 50 is operable to cease storing messages in the outbound data buffer 100 of the memory subsystem 54 upon detection of insertion of a sample carrier 22 into the carrier port 20 as described above. After a predefined time period in which the wireless communication circuit 52 thereafter fails to find such messages in the outbound data buffer 100 of the memory subsystem 54, the wireless communication circuit 52 begins transitioning to lower power states as described above. When the UI processor 50 then resumes storing messages in the outbound data buffer 100 of the memory subsystem 54 after the analyte measurement is complete, the wireless communication circuit 52 wakes up to full power to service it. This may take at least a wake up time period, e.g., as much as 400 milliseconds, if the wireless communication circuit 52 has just entered the lowest power "deep sleep" state when the first message is stored in the outbound data buffer 100 of the memory subsystem 54 after the analyte measurement is complete.

Unless the remote electronic devices 12 and the insulin infusion pump 14 are communicating information, the wireless communication circuit 52 is generally in one of the lower power sleep states or modes. When insertion of a sample carrier 22 into the carrier port 20 is detected, the electronic device 12 performs an analyte determination test as described above. The electronic device 12 generally does not wirelessly communicate with the insulin infusion pump 14 during the analyte determination test, and the wireless communication circuit 52 is thus typically in one of the lower power sleep states when insertion of the sample carrier 22 into the carrier port 20 is detected. Because the UI processor 50 stops storing messages in the outbound data buffer 100 of the memory subsystem 54 when insertion of the sample carrier 22 into the carrier port 20 is detected, the wireless communication circuit 52 therefore typically enters successively lower power sleep states after insertion of the sample carrier 22 into the carrier port 20 is detected.

While the electronic device 12 is illustrated and described above with respect to FIGS. 1-3 as including an analyte measuring facility 88, such an analyte measuring facility may be omitted in alternative embodiments. In any case, the electronic device 12 and the insulin infusion pump 14 may illustratively be paired according to a pairing process that establishes secure communications between the electronic device 12 and the insulin infusion pump 14. Illustratively, this process may be carried out to initially establish secure wireless communications between the electronic device 12 and a particular insulin infusion pump 14, and then again if the electronic device 12 is to be paired with a different insulin infusion pump 14 or vice versa. In one illustrative embodiment, the electronic device 12 may only be paired with a single insulin infusion pump 14 at a time, although this disclosure contemplates other embodiments in which the electronic device 12 may be paired with any number of medical devices 14 generally and/or other electronic devices, and/or in which the medical device 14 may be paired with any number of electronic devices 12 or other medical devices. In any case, further details relating to one illustrative pairing and authentication process are provided in co-pending PCT Patent Application No. PCT/US2008/066247, entitled METHOD FOR PAIRING AND AUTHENTICATING ONE OR MORE MEDICAL DEVICES AND ONE OR MORE REMOTE ELECTRONIC DEVICES, the disclosure of which has been incorporated herein by reference.

Figure 4:
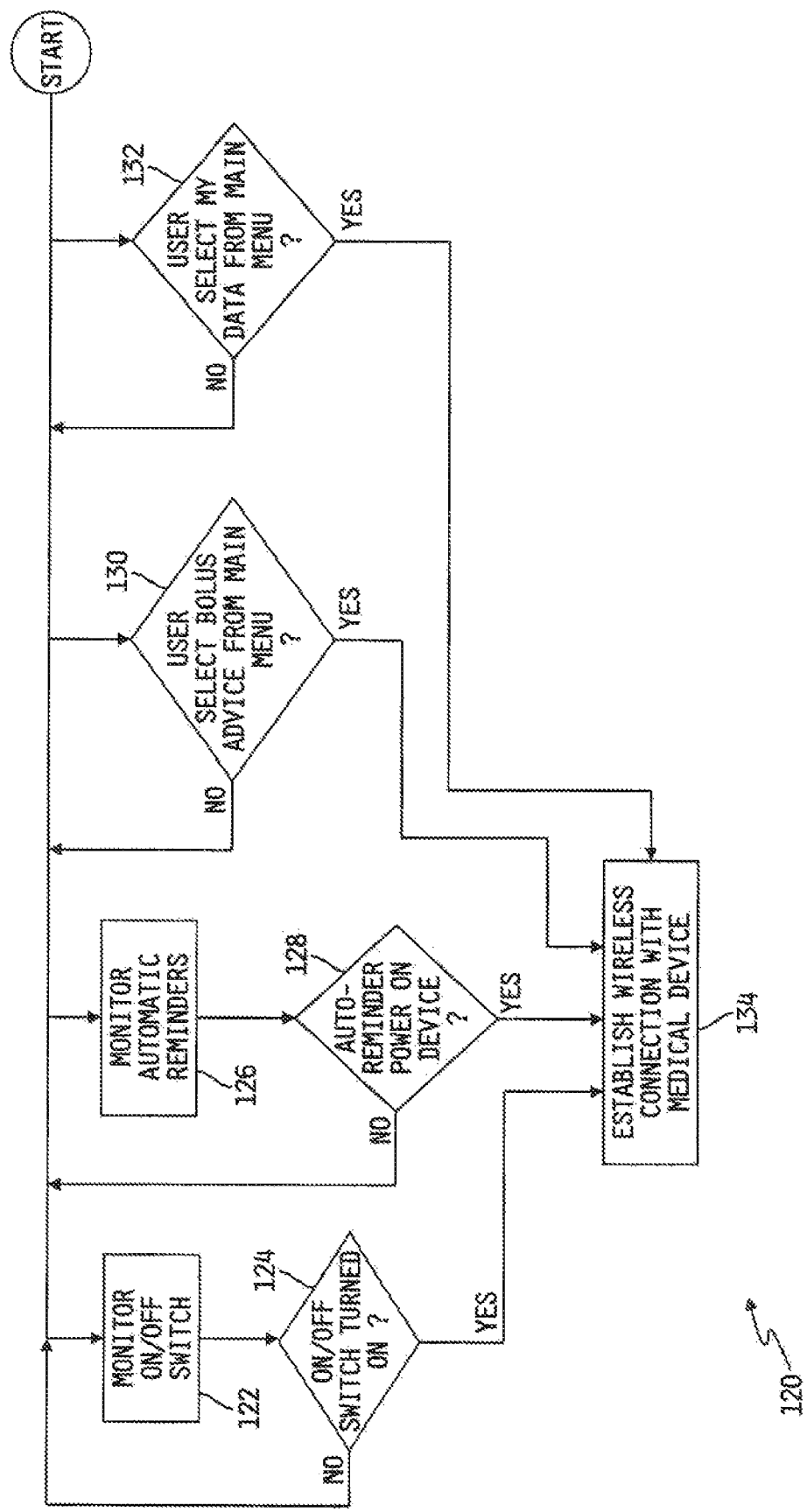
FIG. 4 shows a flowchart of one illustrative embodiment of a process carried out in the remote electronic device for establishing wireless communications between the remote electronic device and the medical device.

Referring now to FIG. 4, a flow chart of one illustrative embodiment of a process 120 is shown that is carried out in the remote electronic device 12 for establishing wireless communications between the remote electronic device 12 and the medical device 14 under various operating conditions of the remote electronic device 12 in which the remote electronic device 12 and the medical device 14 may not already be connected via a wireless communication link 40. Illustratively, the process 120 is stored in the memory device 66 of the UI processor 50 in the form of instructions that are executable by the UI processor 50 to automatically establish wireless communications between the remote electronic device 12 and the medical device 14 under certain operating conditions. At the beginning of the process 120, the UI processor 50 is operable to simultaneously to execute steps at 122, 126, 130 and 132. At step 122, the UI processor 50 is operable to monitor the on/off switch of the remote electronic device 12. Thereafter at step 124, the UI processor 50 is operable to determine whether the on/off switch of the remote electronic device 12 has been turned on. If not, the process 120 loops back to step 122. If, at step 124, the UI processor 50 determines that the on/off switch has been turned on, the UI processor 50 is operable at step 134 to establish wireless communications with the medical device 14 as described hereinabove with respect to FIGS. 1-3.

The UI processor 50 is operable at step 126 of the process 120 to monitor a number of automatic reminders programmed therein. Thereafter at step 128, the UI processor 50 is operable to determine whether any of the programmed automatic reminders has triggered the power up of the remote electronic device 12 from a powered down state. Alternatively, the UI processor 50 may be operable at steps 126 and 128 to monitor the on/off state of the remote electronic device 12, and to determine whether and when the remote electronic device 12 powers up from a powered down state in response to the occurrence of an automatic reminder. In either case, the "NO" branch of step 128 loops back to step 126, and the "YES" branch of step 128 advances to step 134 where the UI processor 50 is operable to establish a wireless connection with the medical device 14 as described above.

The UI processor 50 is operable at step 130 to monitor the main menu to determine whether the user has selected the bolus advice feature from the main menu (or alternatively from a blood glucose determination menu). If not, the process 120 loops back to the beginning of step 130, and if the UI processor 50 determines at step 130 that a user has selected the bolus advice feature, the process 120 advances to step 134 where the UI processor 50 is operable to establish a wireless connection with the medical device 14 as described above.

The UI processor 50 is operable at 132 to monitor the main menu display on the display device 18 of the remote electronic device 12 to determine whether a user has selected the "my data" feature from the main menu. Illustratively, the "my data" feature corresponds to a data viewing, editing and reporting feature via which a user may view current, historical and trend data relating to operation of the on-board glucose meter and/or the medical device 14. In any case, the "NO" branch at step 132 loops back to the beginning of step 132, and the "YES" branch advances to step 134 where the UI processor 50 is operable to establish wireless connection with the medical device 14 as described above.

Figure 5:
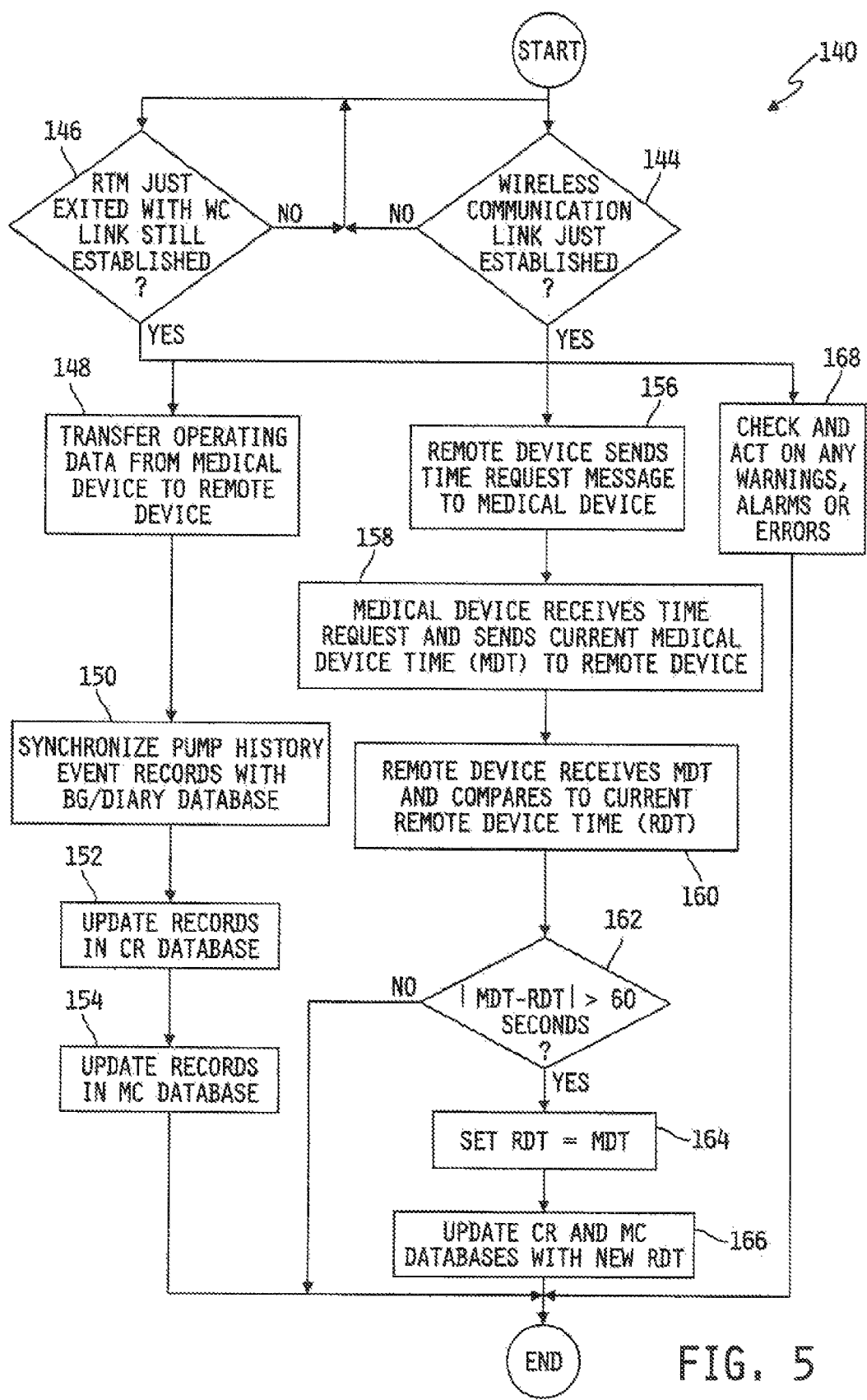
FIG. 5 shows a flowchart of one illustrative embodiment of a process carried out in the remote electronic device for processing information after a wireless connection is established between the remote electronic device and the medical device.

Referring now to FIG. 5, a flow chart is shown of one illustrative embodiment of a process 140 that is carried out in the remote electronic device 12 for processing information at certain times when a wireless connection is established between the remote electronic device 12 and the medical device 14. Illustratively, the process 140 is stored in the memory device 66 of the UI processor 50 in the form of instructions that are executable by the UI processor 50 to carry out the process 140. The process 140 begins at step 144 where the UI processor 50 is operable to determine whether a wireless communication link has just been established between the remote electronic device 12 and the medical device 14, such as via one or more of the operations illustrated and described with respect to FIG. 4. If not, the process 140 loops back to the beginning of step 144. Illustratively, the UI processor 50 is operable while executing step 144 to also execute step 146 where the UI processor 50 is operable to determine whether the remote electronic device 12 has just exited a remote terminal operating mode in which the remote electronic device 12 is configured to control operation of the medical device 14 in substantially real time over a wireless connection established between the two devices 12, 14. If, at step 146, the UI processor 50 determines that the remote electronic device 12 has not just exited the remote terminal operating mode with the wireless connection still established, the process 140 loops back to the beginning of steps 144 and 146. If, at step 146, the UI processor 50 determines that the remote electronic device has just exited the remote terminal operating mode with the wireless connection still established between the devices 12, 14 or if at step 144, the UI processor 50 determines that a wireless communication link has just been established between the remote electronic device 12 and the medical device 14, the UI processor 50 is operable to execute each of steps 148, 156 and 168.

Figure 6:
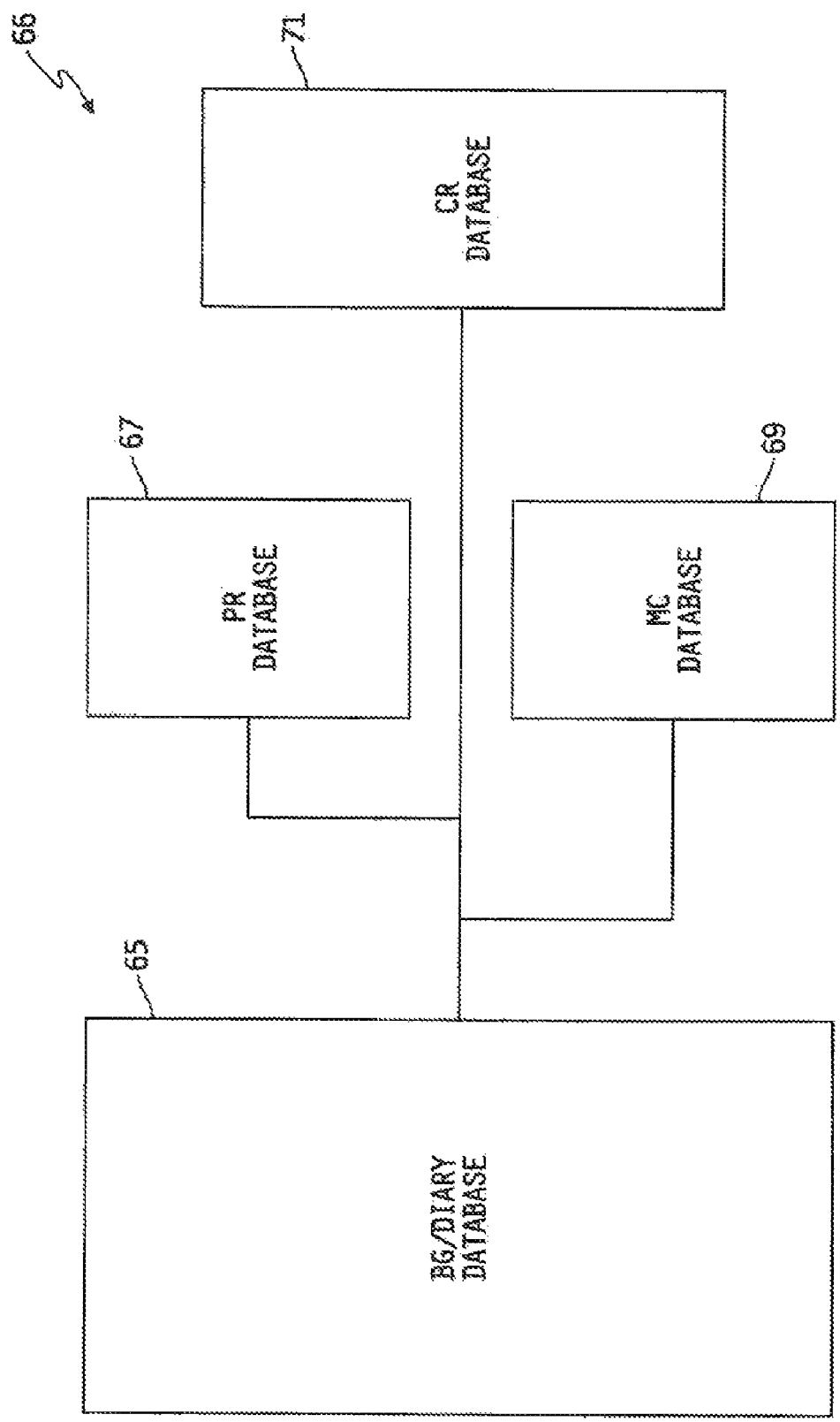
FIG. 6 shows a diagram of one illustrative embodiment of a number of databases defined in the memory device of the remote electronic device.

At step 148, the UI processor 50 is operable to transfer operating data, e.g., event history information, from the medical device 14 to the remote electronic device 12 via the wireless communication link. In one embodiment, the remote electronic device 12 includes four separate databases that hold history information for computing boluses and for reviewing and/or further analyzing. Referring to FIG. 6, a diagram is shown of one illustrative embodiment of four such databases that are included in the remote electronic device 12, and that are illustratively located in the memory device 66. The four databases include a BG/Diary database 65, a pump records (PR) database 67, a meal correction (MC) database 69 and a correction records (CR) database 71. The BG/Diary database 65 acts as the main database, and the PR database 67, MC database 69 and CR database 71 are support databases which hold data used to calculate active insulin and bolus advice. The BG/Diary database 65 holds the overall resulting bolus advice data long with interim and input data used in determining the bolus advice. As illustrated in FIG. 6, the BG/Diary database 65 is in data communication with each of the other three databases 67, 69 and 71.

In one illustrative embodiment, the BG/Diary database 65 can hold 1000 records and operates as a circular queue that will over-write the records, oldest first, after the first 1000 records have been accumulated. The BG/Diary database 65 contains the bolus advice calculations and input parameters used in the bolus calculations.

In one embodiment, the correction records (CR) database 71 can hold 150 records and also operates as a circular queue that will over-write the records, oldest first, after the first 150 records have been accumulated. In this embodiment, the CR database 71 is intended to hold 8 hours of prior bolus information. The correction records database 71 is monitored over time by the UI processor 50 to determine which of the records are active and which are inactive. The correction records database 71 is used to determine the amount of active insulin in the body, and uses only the active records to determine this parameter. Each record in the CR database 71 is associated with a specific record in the BG/Diary database, and this association is determined by the BG/Diary date and time stamp and a record counter value of the specific BG/Diary database record. In this example embodiment, the BG/Diary results are stored with a resolution of one minute, and multiple BG/Diary records can be created each minute. Accordingly, the record counter is useful in this embodiment to distinguish between multiple BG/Diary records that may have the same date and time stamp.

In the illustrated embodiment, the meal correction database 69 is a single record database that is updated each time a BG/Diary record with a carbohydrate amount that exceeds a programmable snack size or meal excursion limit is added to the BG/Diary database 65. This update occurs whether the current meal correction record is active or not. Like the correction records database 71, the meal correction database is monitored over time to determine whether the sole record in the meal correction database 69 is or is not currently active. The meal correction record is used when determining the upper BG level that is, in turn, used during the calculation of a correction bolus. The sole record in the meal correction database 69 is also associated with a specific record in the BG/Diary database 65, and this association is determined by the BG/Diary date and time stamp and a record counter value for the specific BG/Diary record.

In the example embodiment, the pump records database 67, like the BG/Diary database 65, can hold 1000 records and also operates as a circular queue that will over-write the records, oldest first, after the first 1000 records have been accumulated. The pump records are received by the pump records database 68 when the operating data from the pump, e.g., the pump history records, are transferred to the remote electronic device 12 according to step 148 of the process 140 of FIG. 5. The pump history records are synchronized with specific records in the BG/Diary database 65 with the intent of matching up actual pump delivery amounts from the pump history records with bolus amounts in the BG/Diary database 65. As will be described in greater detail hereinafter with respect to FIGS. 9A and 9B, pump history records that match corresponding BG/Diary records are used to confirm the bolus amounts in the BG/Diary database 65 as part of the synchronization process. When a pump record cannot be matched with a specific record in the BG/Diary database 65, a new record containing the pump information is added to the BG/Diary database 65. The PR database 67, in the illustrated embodiment, is used strictly as a scratch pad area for holding pump records that are transferred from the pump 14 to the remote electronic device pursuant to step 148 of the process 140 of FIG. 5.

Figure 7:
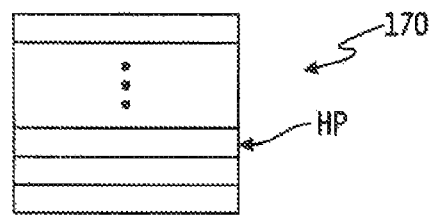
FIG. 7 shows a diagram of a data buffer in the medical device that is configured to store time stamped medical device events.
Figure 8:
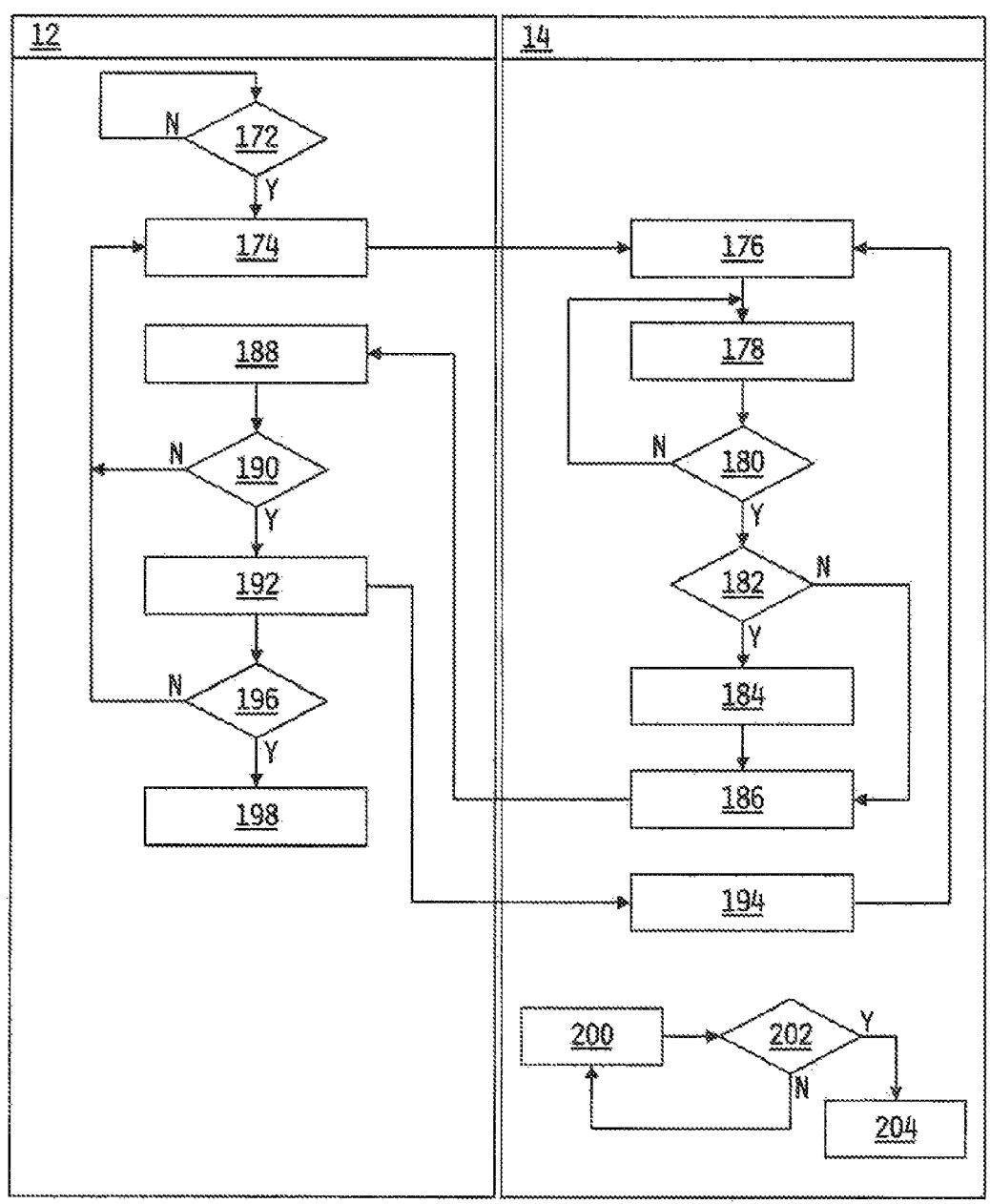
FIG. 8 shows a flowchart of one illustrative embodiment of a process for transferring portions of the time stamped medical device events from the medical device to the remote electronic device.

Referring now to FIGS. 7 and 8, one illustrative embodiment of the process carried out at step 148 of the process 140 illustrated in FIG. 5 is shown. Referring specifically to FIG. 7, a diagram is shown of a data buffer 170 that resides in the pump history (PH) memory device 29 of the medical device 14. The data buffer 170 is configured to store time stamped medical device event records, and in the embodiment illustrated in FIG. 7 the data buffer 170 is a first-in-first-out (FIFO) buffer that is sized to store a predefined number, e.g., 4500, medical device event records. Also in the illustrated embodiment, a history position pointer, HP, points to the last medical device event record that was transferred from the medical device 14 to the remote electronic device 12 during the most recent download of the medical device event records from the medical device 14 to the remote electronic device 12. However, when the medical device 14 is re-paired with a new remote electronic device 12 or re-paired with an existing remote electronic device 12, the history position pointer, HP, is illustratively set to point to the first record in the data buffer.

In any case, the medical device event records are illustratively stored in the data buffer 170 in the order of time of occurrence such that the oldest medical device event record is at the output of the data buffer 170 and the newest medical device event record is at the input of the data buffer 170.

Referring now to FIG. 8, a flow chart is shown of one illustrative embodiment of a process for carrying out step 148 of the process 140 of FIG. 5 to transfer portions of the time stamped medical device event records from the medical device 14 to the remote electronic device 12. The flow chart of FIG. 8 is partitioned into portions that are carried out by the remote electronic device 12 and other portions that are carried out by the medical device 14. Thus, the remote electronic device will carry out some of the steps of the illustrative process while the medical device 14 will carry out others. The data transfer process begins at step 172 where the UI processor 50 of the remote electronic device 12 is operable to determine whether a wireless connection between the remote electronic device 12 and the medical device 14 has just been established. If not, the process loops back to the beginning of step 172, otherwise the process advances to step 174 where the UI processor 50 of the remote electronic device 12 is operable to send a read pump history command to the medical device 14 via the wireless communication circuit 54. Thereafter at step 176, the processor 28 of the medical device 14 is operable to receive, via the wireless communication circuit 30, the read pump history command sent by the remote electronic device 12. Thereafter at step 178, the processor 28 of the medical device 14 is operable to scan the pump history records that have been saved in the memory device 29 since storage therein of the pump history record to which the history position pointer, HP, points. If, at step 180, the processor 28 determines that enough records have been found in the scan to form a block of records, or if a response time for responding to the read pump history command sent by the remote electronic device 12 is about to expire, the process advances from step 180 to step 182. Otherwise, step 180 loops back to step 178 to continue to scan and search for pump history records that have been stored in the data buffer 170 since the storage therein of the pump history record to which HP points.

At step 182, the processor 28 of the medical device 14 is operable to determine whether a history gap flag has been set. If so, the process advances to step 184 where the processor 28 includes a history gap indicator in the response to be sent to the remote electronic device 12. The processor 28 is further operable at step 184 to determine from the data buffer 170 whether additional pump history data is available after detecting the history gap from the history gap flag. Illustratively, the processor 28 further includes information in the response to be sent to the remote electronic device 12 that indicates whether any such additional pump history data is available after the detected history gap. From step 184, and from the "NO" branch of step 182, the process advances to step 186 where the processor 28 is operable to send, via the wireless communication circuit 30, a block or partial block of pump history event records to the remote electronic device 12. Thereafter at step 188, the UI processor 50 of the remote electronic device 12 is operable to receive, via the wireless communication circuit 54, the block or partial block of pump history event records from the medical device 14. Thereafter at step 190, the UI processor 50 is operable to determine whether the processing of the block or partial block of pump history event records, e.g., transferring of the pump history event records to the PR database 67, was successful. If not, the process loops back to step 174 where the pump history request, search and transfer process just described is repeated. If, at step 190, the UI processor 50 determines that the processing of the block or partial block of pump history event records at step 188 was successful, the process advances to step 192 where the UI processor 50 is operable to send the wireless communication circuit 54, a successful transfer message to the medical device 14. Thereafter at step 194, the processor 28 of the medical device 14 is operable to receive, via the wireless communication circuit 30, the successful transfer message, and to deactivate or render inactive the history gap flag and set the history position pointer, HP, to a new location in the data buffer 170 that corresponds to the oldest pump history event record that was sent to, and successfully processed by, the remote electronic device 12. From step 194, the process loops back to step 176 to again scan pump history event records that were saved in the pump history memory device 29 since storing the pump history event record to which the newly positioned history position pointer, HP, now points.

Step 192 of the illustrated process additionally advances to step 196 where the UI processor 50 is operable to determine whether all pump history event records since the previous execution of the illustrative process have been transferred from the medical device 14 to the remote electronic device 12. Illustratively, the processor 28 of the medical device 14 is operable to include a last record indicator in the block or partial block of pump history event records transferred from the medical device 14 to the remote electronic device 12 at step 184. If, at step 196, the UI processor 50 determines that the last record information was received and processed in the most recent block or partial block of the pump history event records sent from the medical device 14 to the remote electronic device 12, the process advances to step 198 where the process ends. Otherwise, the process loops from step 196 back to step 174 where the process continues as described until all pump history event records that were stored in the memory device 29 of the processor 28 since the previous execution of the illustrated process are transferred.

At step 200, the processor 28 of the medical device 14 is operable to monitor the data in the pump history event record to which the history position pointer, HP, points. Thereafter at step 202, the processor 28 is operable to determine whether the data in the pump history event record to which HP points has changed since the previous transfer of information from the medical device 14 to the remote electronic device 12. If so, this means that at least some of the pump history event records stored in the data buffer 170 have been overwritten since the last transfer of information from the medical device 14 to the remote electronic device 12, and that a gap in the time line of pump history event records therefore exists. In this case, the process advances from step 202 to step 204 where the processor 28 is operable to activate the history gap flag described above. Otherwise, step 202 loops back to step 200.

Figure 9A:
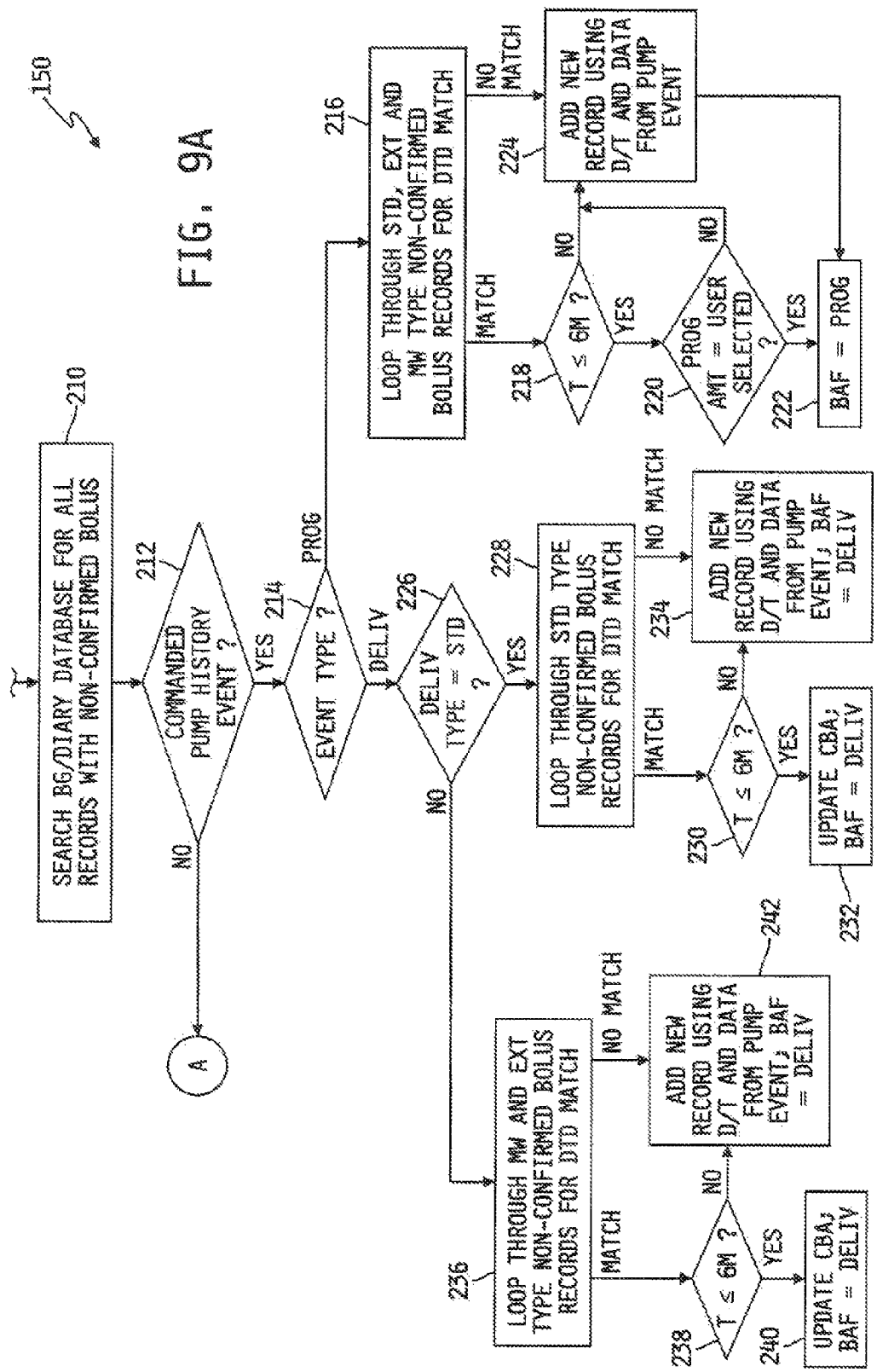
FIGS. 9A and 9B show a flowchart of one illustrative embodiment of a process carried out by the remote electronic device for processing history data transferred from the medical device to the remote electronic device.
Figure 9B:
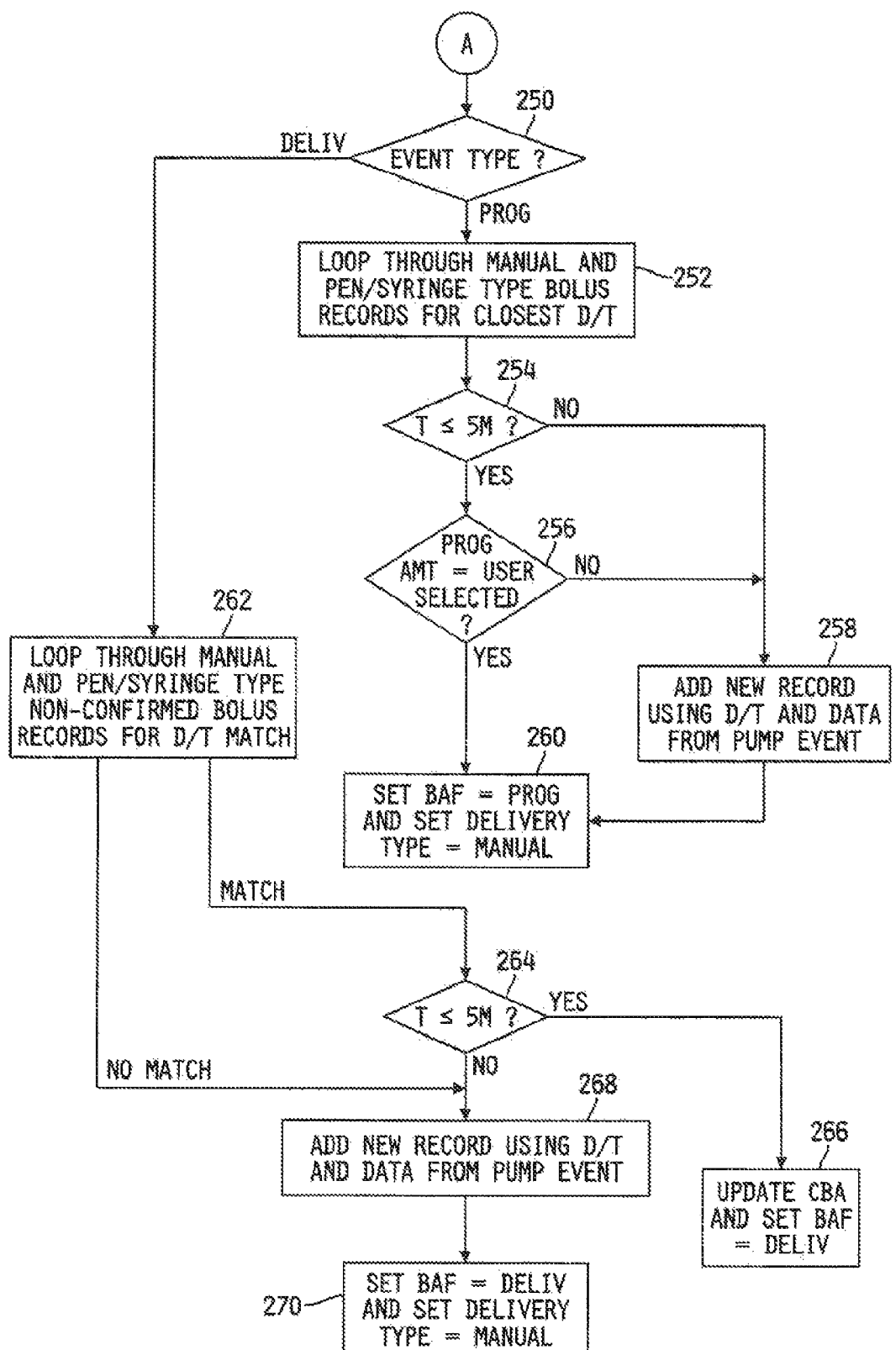

Referring again to FIG. 5, the process 140 advances from step 148 to step 150 where the UI processor 50 is operable to process the medical device operating data that was transferred from the medical device 14 to the remote electronic device 12 at step 148 to thereby synchronize the pump history event records with the BG/Diary database 65. Referring now to FIGS. 9A and 9B, a flowchart is shown of one illustrative process for carrying out step 150 of the process 140 of FIG. 5 to process the pump history records and synchronize the pump history records with the BG/Diary records in the BG/Diary database 65. Illustratively, the process of FIG. 9A is stored in the memory unit 66 in the form of instructions that are executable by the UI processor 50 to carry out the illustrated process.

The pump history records transferred from the pump 14 to the remote electronic device 12 may include commanded and non-commanded pump events. Commanded events are generally those in which the remote electronic device 12 commands the liquid infusion pump 14, via the wireless communication circuits 52 and 30 respectively, to deliver a desired bolus amount and type, except when the remote electronic device 12 and the pump 14 are operating in a remote terminal operating mode as briefly described above. In such cases, the commanded events are treated as being locally commanded, i.e., commanded by pressing appropriate ones of the keys 32 of the pump 14. Non-commanded events, in contrast, are those that were performed manually by the user and not commanded by the remote electronic device 12. Non-commanded events may include manually programming the liquid infusion pump 14 to deliver desired bolus amounts and types, and also manually delivering bolus amounts via a syringe or drug delivery pen. In the process illustrated in FIG. 9A, both commanded and non-commanded events are read from the pump history records transferred from the pump 14 to the remote electronic device 12 and synchronized with the BG/Diary database 65. Non-commanded events may or may not be synchronized or associated with an existing BG result. If non-commanded events are not synchronized, they are in effect orphaned but nevertheless considered part of the overall history of the user.

Illustratively, the UI processor 50 is operable pursuant to the process illustrated in FIGS. 9A and 9B to synchronize the pump event records with the BG/Diary database 65 immediately after the records are transferred from the pump 14 to the remote electronic device 12. Generally, this process entails attempting to match the bolus type, bolus amount, date and time stamp of each pump event record to an existing BG/Diary record that does not yet have an associated programmed or delivered bolus amount. If a pump event record cannot be matched with such an existing BG/Diary record, a new BG/Diary record is created and added to the BG/Diary database 65. Each such new addition of a BG/Diary record will require a corresponding update of the correction records database 71.

If a pump event record is matched with an existing BG/Diary record, the delivered bolus amount is checked for confirmation. If the delivered amount in the pump event record matches the bolus amount in the matched. BG/Diary record, the bolus amount is confirmed and the BG/Diary record is updated to reflect this result. If, on the other hand, the delivered amount in the pump event record is different from the bolus amount in the matched BG/Diary record, the actual delivered amount is confirmed and the BG/Diary record is updated to reflect this result. In this latter case, however, the correction records database 71 is updated to reflect the actual delivered bolus amount. Illustratively, the correction records database 71 is updated in this manner to ensure accuracy of the active insulin value that can be determined from the data.

Figure 11:
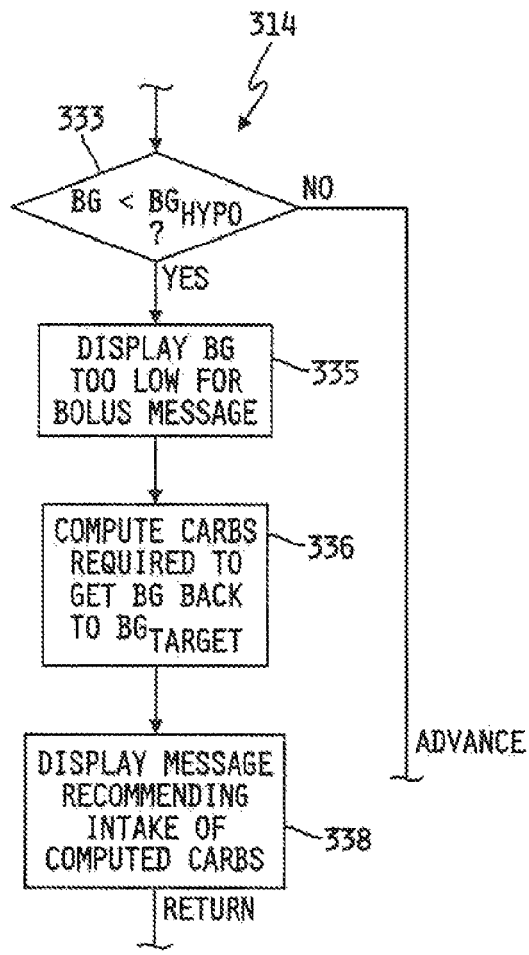
FIG. 11 shows a flowchart of a flowchart of one illustrative embodiment of a hypoglycemic test process.

The process illustrated in FIGS. 9A and 9B is executed once for each pump event record that is transferred from the pump 14 to the remote electronic device 12. The illustrated process begins at step 210 where the UI processor 50 is operable to search the BG/Diary database for all records with non-confirmed bolus amounts. Thereafter at step 212, the UI processor 50 is operable to determine whether the present pump event record corresponds to a commanded event. Generally, the pump event records will contain a field that defines whether the pump event was a commanded or non-commanded event. If the UI processor 50 determines at step 212 that the current pump event is not a commanded event, the process advances to step A (FIG. 11). If the UI processor 50 instead determines at step 212 that the current pump event record corresponds to a commanded pump event, the process advances to step 214 where the UI processor 50 is operable to determine the event type of the current pump record, i.e., whether the current pump record corresponds to a programmed bolus amount or a delivered bolus amount. Again, the pump event records illustratively contain a field that defines whether the pump event was a programmed or a delivered bolus amount.

If the UI processor 50 determines at step 214 that the current pump event corresponds to a programmed bolus amount, the illustrated process advances to step 216 where the UI processor 50 searches through the non-confirmed and non-programmed Standard, Extended and Multi-wave bolus type records in the BG/Diary database 65 for a record having a date/time stamp and bolus delivery type (DTD) that matches that of the current pump event record. If the UI microprocessor 50 finds such a match at step 216, the illustrated process advances to step 218 where the UI processor 50 determines whether the time stamp (T) of the matched BG/Diary record is within a predefined time value, e.g., 6 minutes, of that of the current pump event record. If so, the illustrated process advances to step 220 where the UI processor 50 is operable to determine whether the programmed bolus amount in the BG/Diary record is equal to a user selected amount. If so, the illustrated process therefore advances to step 222 where the UI processor 50 is operable to set a bolus advice flag in the current BG/Diary record to FROG. If at step 218 the UI processor 50 determines that the time stamps (T) of the matched BG/Diary record is not within the predefined time value of that of the current pump event record, the illustrated process advances to step 224. Likewise, if the UI processor 50 determines at step 220 that the programmed bolus amount in the BG/Diary record is not equal to a user selected amount, the illustrated process advances to step 224. Also, if the UI processor 50 does not find a match at step 216, the illustrated process advances to step 224. At step 224, the UI processor 50 is operable to create and add a new record to the BG/Diary database 65 using the date/time stamp and data from the current pump event record, and to set a bolus advice flag of this new record to PROG.

If at step 214, the UI processor 50 determines that the current pump event corresponds to a delivered bolus amount, the illustrated process advances to step 226 were the UI processor 50 is operable to determine whether the bolus delivery type was a standard bolus or either of an extended bolus and a multi-wave bolus. If the UI processor 50 determines at step 226 that the delivered bolus type is a standard bolus (STD), the illustrated process advances to step 228 where the UI processor 50 searches through the non-confirmed and programmed Standard bolus type records in the BG/Diary database 65 for a record having a date/time stamp and bolus delivery type (DTD) that matches that of the current pump event record. If the UI microprocessor 50 finds such a match at step 228, the illustrated process advances to step 230 where the UI processor 50 determines whether the time stamp (T) of the matched BG/Diary record is within a predefined time value, e.g., 6 minutes, of that of the current pump event record. If so, the illustrated process advances to step 232 where the UI processor 50 is operable to update the confirmed bolus amount with the delivered bolus amount from the pump event record and to then set the bolus advice flag to DELIV. If at step 230 the UI processor 50 instead determines that the time stamps (T) of the matched BG/Diary record is not within the predefined time value of that of the current pump event record, or the UI processor 50 does not find a match at step 228, the illustrated process advances to step 234 where the UI processor 50 is operable to create and add a new record to the BG/Diary database 65 using the date/time stamp and data from the current pump event record, and to set a bolus advice flag of this new record to DELIV.

If, at step 226, the UI processor 50 determines from the pump event record that the delivered bolus type is not a standard bolus (STD), the illustrated process advances to step 236 where the UI processor 50 searches through the non-confirmed and programmed Extended (EXT) and Multi-wave (MW) bolus type records in the BG/Diary database 65 for a record having a date/time stamp and bolus delivery type (DTD) that matches that of the current pump event record. If the UI microprocessor 50 finds such a match at step 236, the illustrated process advances to step 238 where the UI processor 50 determines whether the time stamp (T) of the matched BG/Diary record is within a predefined time value, e.g., 6 minutes, of that of the current pump event record. If so, the illustrated process advances to step 240 where the UI processor 50 is operable to update the confirmed bolus amount with the delivered bolus amount from the pump event record and to then set the bolus advice flag to DELIV. If at step 238 the UI processor 50 instead determines that the time stamp (T) of the matched BG/Diary record is not within the predefined time value of that of the current pump event record, or the UI processor 50 does not find a match at step 236, the illustrated process advances to step 242 where the UI processor 50 is operable to create and add a new record to the BG/Diary database 65 using the date/time stamp and data from the current pump event record, and to set a bolus advice flag of this new record to DELIV.

Referring now to FIG. 9B, the "A" branch of step 212 of the process illustrated in FIG. 9A advances to step 250 where the UI processor 50 is operable to determine the event type of the current pump record, i.e., whether the current pump record corresponds to a programmed bolus amount or a delivered bolus amount. If the UI processor 50 determines the event type to be a programmed bolus event, PROG, the process advances to step 252 where the UI processor 50 is operable to search through the non-confirmed and non-programmed manual and pen/syringe type bolus records in the BG/Diary database 65 for a record having a date/time stamp that is closest to that of the current pump event record. Thereafter at step 254 the UI microprocessor 50 is operable to determine whether the time stamp (T) of the BG/Diary record selected at step 252 is within a predefined time value, e.g., 5 minutes, of that of the current pump event record. If so, the illustrated process advances to step 256 where the UI processor 50 is operable to determine whether the programmed bolus amount in the BG/Diary record is equal to a user selected amount. If so, the illustrated process advances to step 260 where the UI processor 50 is operable to set the bolus advice flag in the current BG/Diary record to PROG and to set the delivery type of the BG/Diary record to MANUAL. From the "NO" branch of either of steps 254 and 256, the illustrated process advances to step 258 where the UI processor 50 is operable to create and add a new record to the BG/Diary database 65 using the date/time stamp and data from the current pump event record, to set a bolus advice flag of this new record to PROG and to set the delivery type of the record to MANUAL.

If, at step 250, the UI processor 50 determines from the current pump history record that the pump event type corresponds to a delivered bolus event, DELIV, the illustrated process advances to step 262 where the UI processor 50 is operable to search through the Manual and Pen/Syringe type, non-confirmed and programmed records in the BG/Diary database 65 for a record having a date/time stamp that matches that of the current pump event record. If the UI microprocessor 50 finds such a match at step 262, the illustrated process advances to step 264 where the UI processor 50 determines whether the time stamp (T) of the matched BG/Diary record is within a predefined time value, e.g., 5 minutes, of that of the current pump event record. If so, the illustrated process advances to step 266 where the UI processor 50 is operable to update the confirmed bolus amount with the delivered bolus amount from the pump event record and to then set the bolus advice flag to DELIV. If at step 262 the UI processor 50 does not find a match, and also from the "NO" branch of step 264, the illustrated process advances to step 268 where the UI processor 50 is operable to create and add a new record to the BG/Diary database 65 using the date/time stamp and data from the current pump event record. Thereafter at step 270, the UI processor 50 is operable to set the bolus advice flag of this new record to DELIV and to set the delivery type to MANUAL.

Referring again to FIG. 5, step 150 advances to step 152 where the UI processor 50 is operable to update records in the correction records database 71. As described above with respect to FIG. 6, the correction records database 71 I used by the UI processor 50 to hold data that is used to compute an active insulin value. Each record in the correction records database illustratively has a limited time for which that record can be used. During this limited time period, a record is considered to be active. Because the records in the correction records database have a limited active time period, they must be reviewed prior to their actual use in determining the active insulin value, and in such a review process records that are no longer active are deactivated by the UI processor 50.

Illustratively, the updating process of step 152 consists simply of searching through the active records of the database 71, finding records that have an end time that is less than or older than the current time of the remote electronic device and marking as deactivated any such found records. Generally, the start and end times of the records in the correction records database 71 are stored and maintained in the current time of the remote electronic device 12. Each time a date and/or time change of the current time of the remote electronic device 12 is changed, the UI processor 50 is operable to adjust the start and end times of the active records in the correction records database 71 so that they always remain synchronized with the current date and time of the remote electronic device 12.

Step 152 of FIG. 5 advances to step 154 where the UI processor 50 is operable to update the record in the meal correction database 69. As described above with respect to FIG. 6, the meal correction record in the meal correction database 69 is used by the UI processor 50 to hold data that is used to compute an upper blood glucose limit (UBGL) as will be described in greater detail hereinafter. Like the records in the correction records database 71, the single record in the meal correction database 69 has a limited time for which it can be used. During this limited time period, the record is considered to be active. Because this record has a limited active time period, it must be reviewed prior to its actual use in determining UBGL, and in such a review process if the UI processor 50 determines that it is no longer active, it is deactivated by the UI processor 50.

Illustratively, the update process of step 154 consists of comparing a meal end time of the meal correction record to the current date and time of the remote electronic device 12, and deactivating the meal correction record if it is less than or older than the date and time of the remote electronic device 12. Generally, the start and end times of the record in the meal correction database 69 is stored and maintained in the current time of the remote electronic device 12, and each time a date and/or time change of the current time of the remote electronic device 12 is changed, the UI processor 50 is operable to adjust the start and end times of the meal correction record so that they always remain synchronized with the current date and time of the remote electronic device 12.

The "YES" branch of steps 144 and 146 of the process 140 of FIG. 5 also advance to step 156 where the UI processor 50 is operable to send a time request message to the medical device 14 via the wireless communication link. Thereafter at step 158, the medical device receives the time request and sends a current medical device time (MDT) to the remote electronic device 12 via the wireless communication link. Thereafter at step 160, the remote electronic device 12 receives MDT and compares the medical device time to the current remote electronic device time (RDT). Following step 160, the UI processor 50 is operable at step 162 to determine whether a difference between MDT and RDT is greater than 60 seconds. If so, the UI processor 50 is operable to set the current remote electronic device time, RDT, equal to the medical device time, MDT that was wirelessly sent by the medical device 14 to the remote electronic device 12 at steps 158 and 160. Following step 164, the process 145 advances to step 166 where the UI processor 50 is operable to update the correction records database 71 and the meal correction database 69 with the new remote device time, RDT. More specifically, when the remote electronic device time, RDT, changes, the active records in the correction records database 71 and the meal correction database 69 are updated based on the new RDT.

The "YES" branch of steps 144 and 146 of the process 140 illustrated in FIG. 5 further advance to step 168 where the UI processor 50 is operable to check and act on any warnings, alarms or errors that are associated with the medical device 14 and the occurrence of which is communicated wirelessly to the remote electronic device 12 when the wireless communication link is established. Following steps 154, 166 and 168 and the "NO" branch of step 162, the process 140 ends.

Figure 10B:
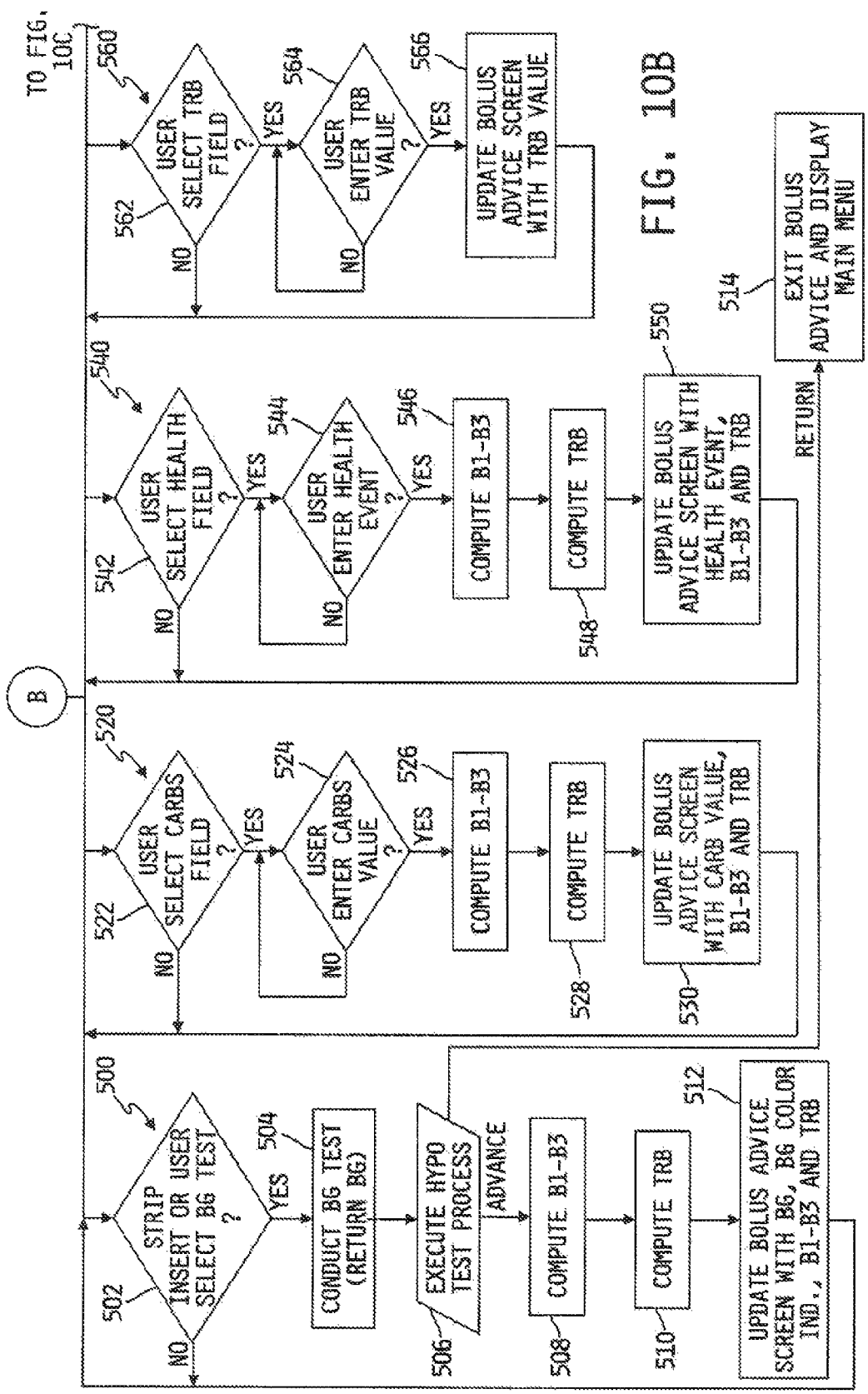
Figure 10C:
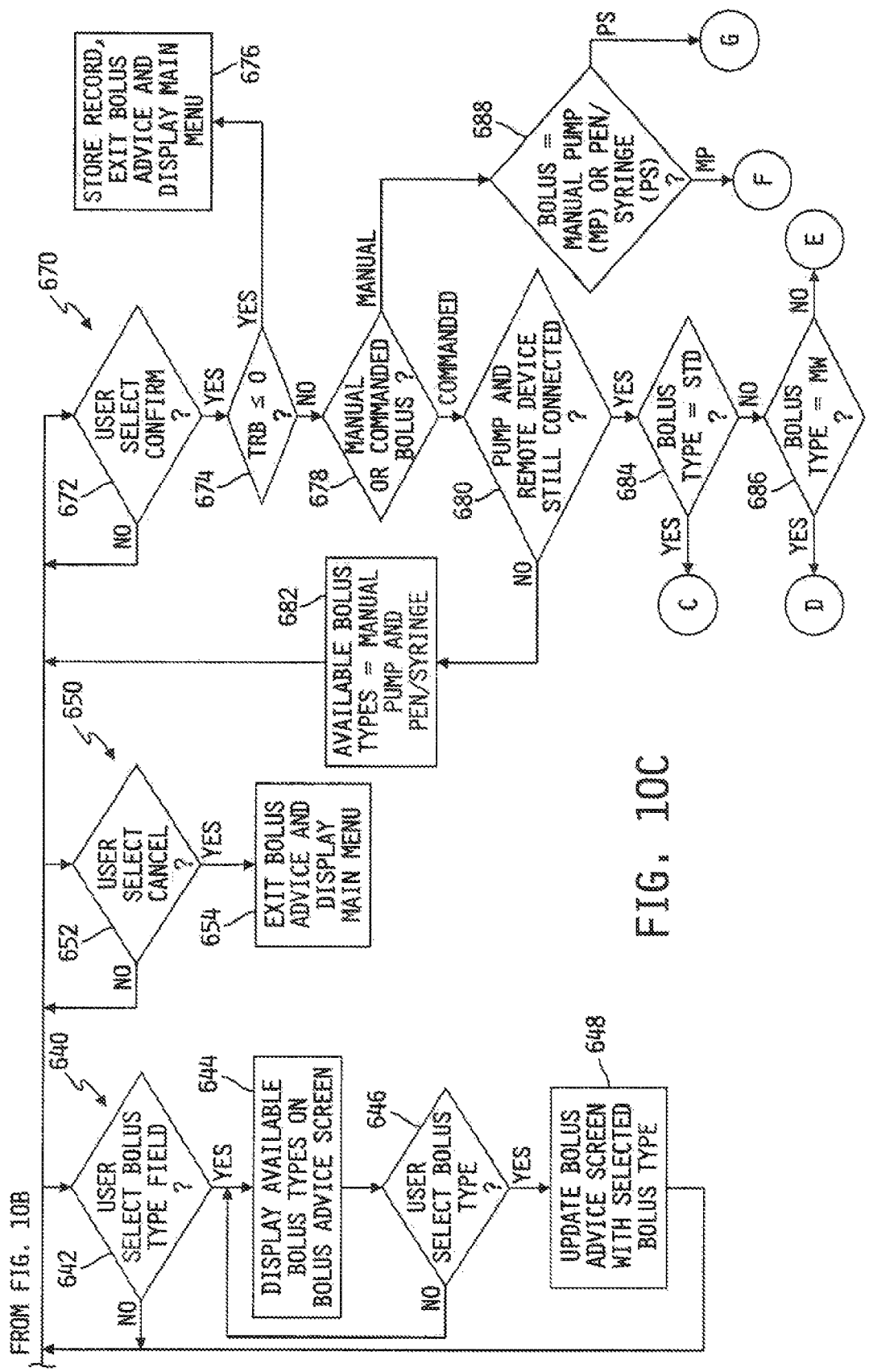

Referring now to FIGS. 10A-10C, a flow chart is shown of one illustrative embodiment of a bolus advice process 300 that is carried out by the remote electronic device 12. In the context of the flowchart of FIGS. 10A and 10B, the medical device 14 is illustratively implemented in the form of an insulin infusion pump, and will be described as such throughout the description of the process 300. It will be understood, however, that this disclosure contemplates alternate embodiments in which the medical device 14 is or includes one or more other conventional medical devices.

Illustratively, the process 300 is stored in the memory device 66 of the UI processor 50 in the form of instructions that are executable by the UI processor 50 to carry out the bolus advice process 300. The process 300 presumes that the remote electronic device 12 is powered up and that the UI processor 50 is currently controlling the display device 18 to display a main menu 302 that is generally displayed upon power up of the remote electronic device 12. Illustratively, the main menu 302 provides for a number of selectable user options that include, but that should not be limited to, a blood glucose (BG) test, a bolus advice process, a pump remote control process 304, a "my data" process 306 and a settings or device set up process. The pump remote control process 304, or remote terminal operational mode as referred to above, illustratively provide a menu-driven process by which the remote electronic device 12 may control operation of the insulin infusion pump 14 substantially in real time. One illustrative embodiment of such a process is described in co-pending PCT Patent Application No. PCT/US2008/066288, and the disclosure of which has been incorporated herein by reference.

The "my data" process 306 illustratively provides for the viewing and editing of diary records, e.g., specific BG test records and pump history records, and also for the analysis of the records over daily and/or weekly time periods. Illustratively, the UI processor 50 stores in the memory 66 up to 1,000 diary records, and up to 250 records may be reviewed using the remote electronic device. The diary records may also be downloaded to a PC or other computer, and using compatible software all records may be viewed and/or analyzed. Each diary record may contain date and time, BG test result, meal time events, carbohydrate value, health event, bolus type, bolus amount and duration. The UI processor can filter and/or sort data from these data records.

The "my data" process also provides for the analysis of the data records in the form of daily and weekly averages, and standard deviations, defined by time slot, and for trend analysis of any of the collected data. Standard day and standard week tables or graphs may be generated to view averages and/or trends. Various charting and table options are also available for presenting data in desired formats.

The BG test process that may be selected from the main menu 302 begins at step 308 where the UI processor 50 determines whether the user has selected the BG test process from the main menu 302. If not, the "NO" branch of step 308 loops back to the beginning of step 308. If, at step 308, the UI processor 50 determines that the user has selected the BG process from the main menu 302, the process 300 advances to step 310 where the UI processor 50 controls the display device 18 to prompt a user to conduct a BG test. In one embodiment, the UI processor 50 controls the display device 18 to visually guide a user through a blood glucose measurement sequence in which a user inserts a carrier 22 into the glucose measurement facility 20 of the remote electronic device 12 and deposits a sample of blood on the carrier 22, after which the blood glucose meter 88 analyzes the blood sample in a conventional manner to produce a blood glucose (BG) value that corresponds to a concentration of glucose in the deposited blood sample. The blood glucose value, BG, is provided by the blood glucose meter 88 that is on-board the remote electronic device 12 to the UI processor 50 as describe hereinabove. From step 310, the process 300 advances to step 312 where the UI processor 50 is operable to control the display device 18 to display the BG value along with an on-screen color indicator that is based on the BG value relative to one or more reference BG values. Further details relating to controls for the display device 18 to display measured or calculated values along with on-screen color indicators having a colors defined by the measured or calculated values are provided in co-pending PCT Patent Application No. PCT/US2008/066262, which is assigned to the assignee of this disclosure, and the disclosure of which has been incorporated herein by reference.

Also following step 310, the process 300 advances to step 314 where the UI processor 50 is operable to execute a hypoglycemic test process in relation to the blood glucose value, BG, measured at step 310. Referring now to FIG. 11, a flowchart is shown of one illustrative embodiment of the hypoglycemic test process 314. Illustratively, the process 314 is stored in the memory 66 of the UI processor 50 in the form of instructions that are executable by the UI processor 50 to conduct the hypoglycemic test. The process 314 begins at step 333 where the UI processor 50 is operable to determine whether the measured BG value, BG, is less than a hypoglycemic limit value, $BG_{HYPO}$. If so, the process 314 advances to step 335 where the UI processor 50 is operable to control the display device 18 to display a message indicating that the measured BG value is too low for a bolus to be delivered. Thereafter at step 336, the UI processor 50 is illustratively operable to compute a number of carbohydrates, e.g., fast-acting carbohydrates, which will be suggested to be taken by the user to get the user's blood glucose value back to a target blood glucose value, $BG_{TARGET}$. In one embodiment, for example, the UI processor 50 is operable at step 364 to compute the required carbohydrates according to the formula CARBS=($BG_{TARGET}$−BG)*IS*CR, wherein IS corresponds to a programmable insulin sensitivity value and CR corresponds to a programmable carbohydrate ratio. In any case, the process 314 advances from step 336 to step 338 where the UI processor 50 is operable to control the display device 18 to display a message recommending intake of the computed amount of carbohydrates. In one embodiment, the CARBS value has a lower limit, e.g., 12 grams, which is substituted for the computed CARBS value when the computed CARBS value is less than the lower limit. Following step 338, the process 314 returns the value RETURN to the process 300 of FIG. 10A, and following the "NO" branch of step 333 the process 314 returns the value ADVANCE to the process 300 of FIG. 10A. Thus, if the blood glucose measurement taken at step 310 is less $BG_{HYPO}$, the process 300 follows the RETURN path from step 314 and loops back to display 302 the main menu. If the blood glucose measurement taken at step 310 is not less than $BG_{HYPO}$, the process 300 follows the ADVANCE path to step 316. In alternate embodiments, the hypoglycemic limit value, $BG_{HYPO}$, may be replaced at step 333 by another suitable lower BG limit.

If the process 300 reaches step 316 as just described, the BG value display screen illustratively provides a bolus option that a user may select to enter the bolus advice process directly from the BG measurement process. The UI processor 50 is accordingly operable following the ADVANCE path from step 314 to step 316 to determine whether the user has selected the bolus option from the BG display. If not, the process 300 advances to step 318 because the user has pressed another key or has selected another option, or alternatively has done nothing and caused the BG value screen to time out. Generally, the UI processor 50 is operable to store the BG value in the memory unit 66 along with measurement time and date information. Illustratively, the user may also store additional information along with the time and date stamp BG value, examples of which may include, but should not be limited to, the timing of the BG measurement relative to meal, bedtime and/or awake time information, amount of carbohydrates taken at the time of the BG measurement, health information such as exercise level, illness or stress, and the like. In any case, if the UI processor 50 determines at step 316 that the user has selected the bolus key option from the BG value display screen, the process 300 advances to step 322.

Figure 12:
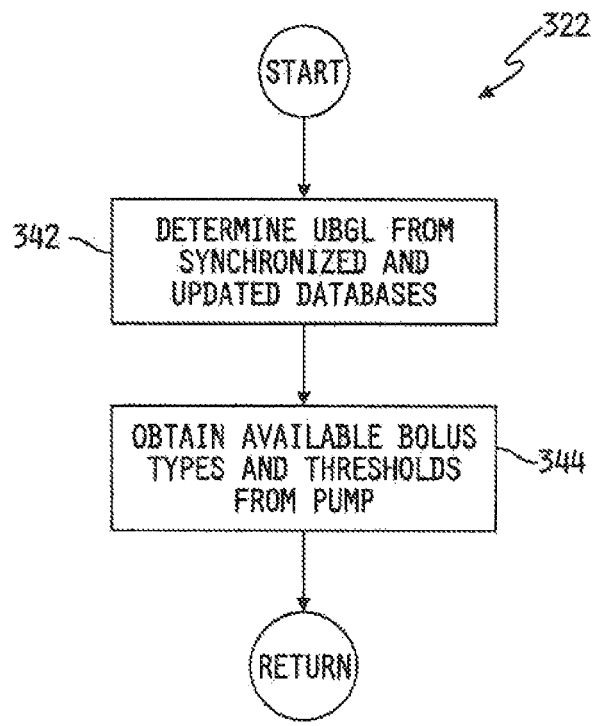
FIG. 12 shows a flowchart of one illustrative process for determining information used by a bolus advice process.

From the main menu 302, the user may alternatively select the bolus advice process, and the UI processor 50 is accordingly operable at step 320 to determine if the user has selected the bolus advice process. If not, the "NO" branch step 320 loops back at the beginning of step 320, and otherwise the process 300 advances to step 322 where the UI processor 50 is operable to determine current bolus advice information; i.e., information that is computed and/or transferred from the pump 14 to the remote electronic device and is thereafter used by the remote electronic device 12 during the bolus advice process. Referring now to FIG. 12, a flowchart is shown of one illustrative embodiment of a process for carrying out step 322. The process illustrated in FIG. 12 begins at step 342 where the UI processor 50 is operable to compute an upper BG limit (UBGL) value from information contained in the databases of FIG. 6.

Figure 14A:
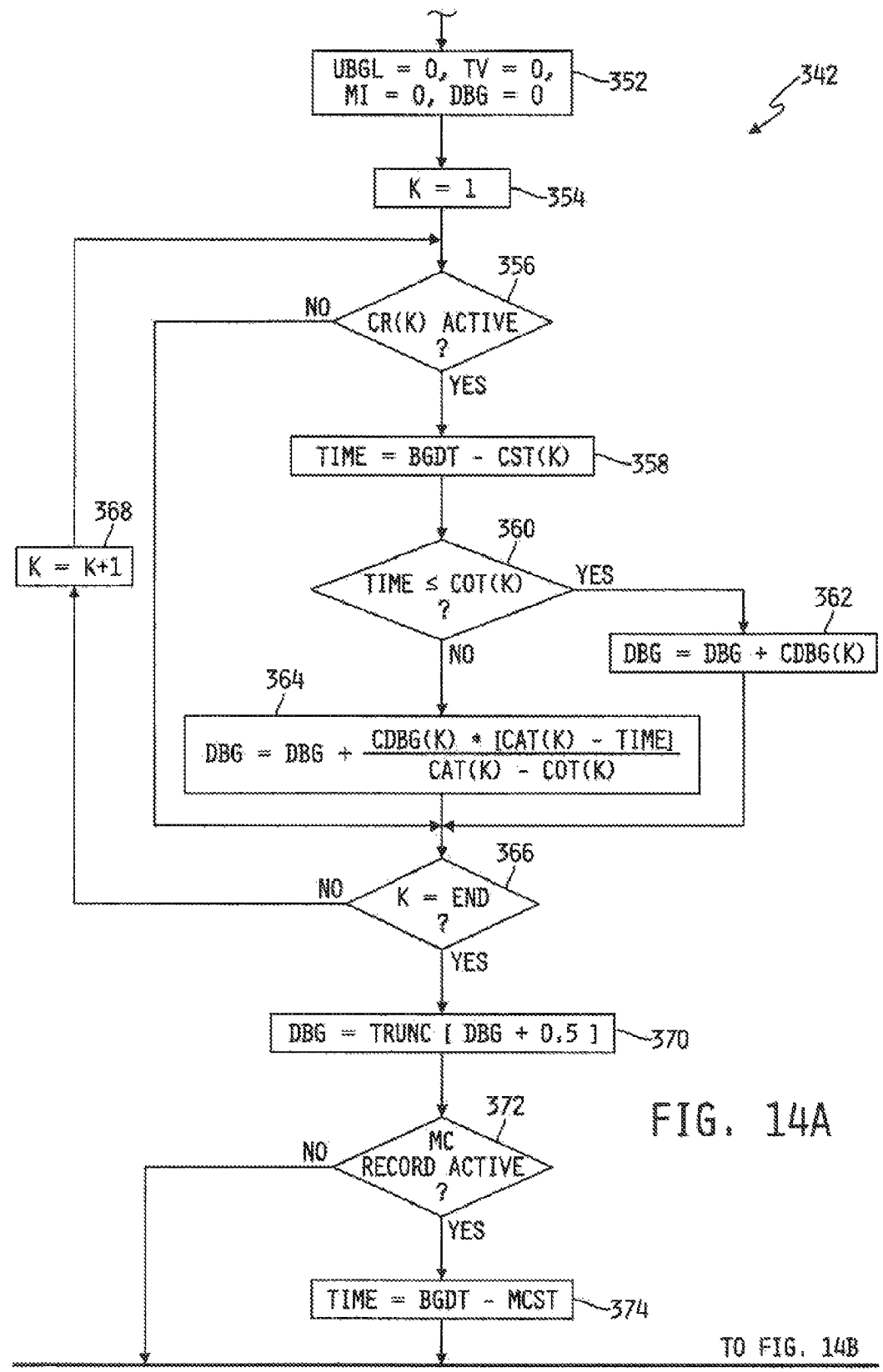
FIGS. 14A and 14B show a flowchart of one illustrative embodiment of a process for determining an upper blood glucose limit.
Figure 14B:
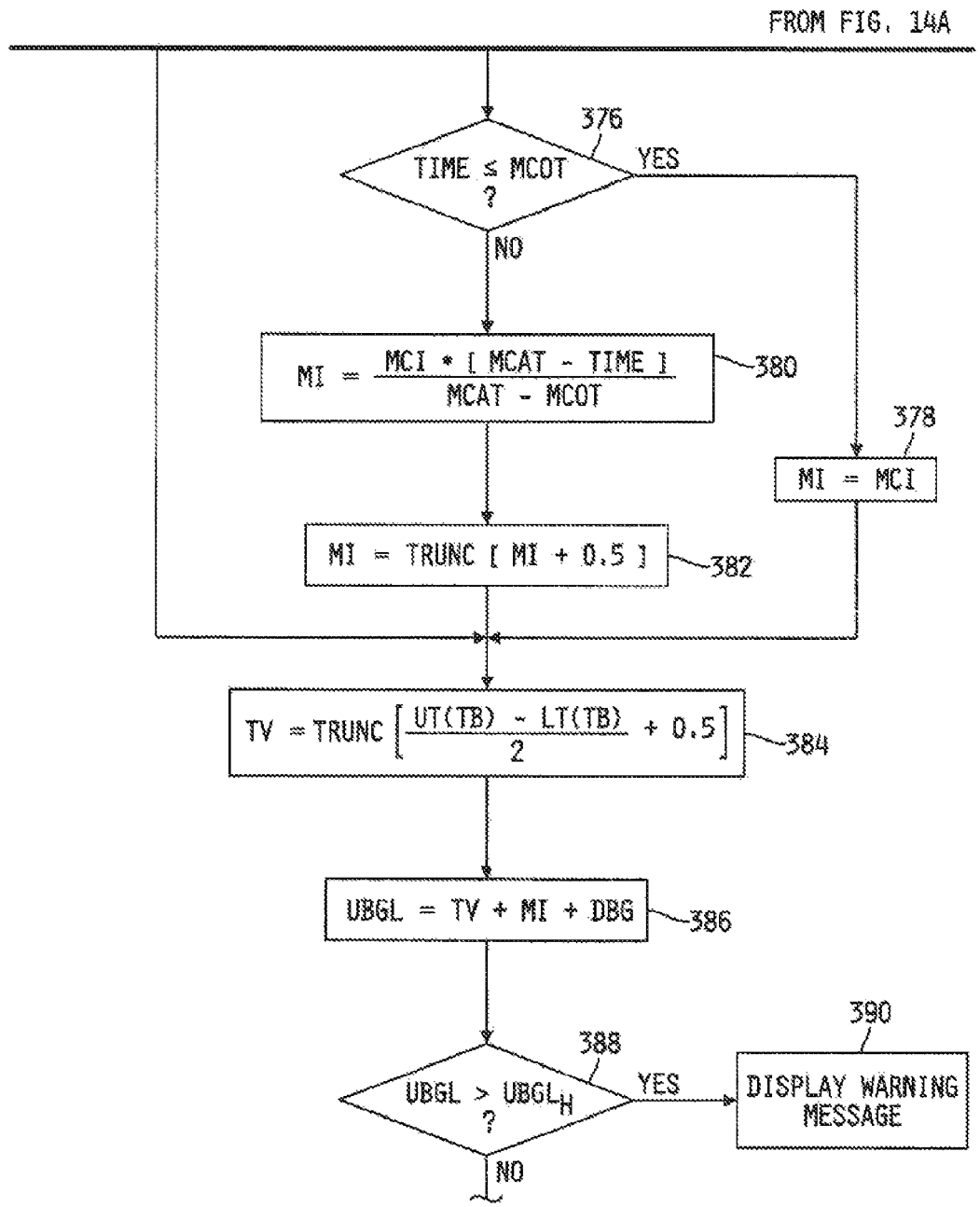

Referring now to FIGS. 14A and 14B, a flowchart is shown of one illustrative embodiment of a process for carrying out step 342 of FIG. 12. Illustratively, the process 342 illustrated in FIGS. 14A and 14B is stored in the memory 66 in the form of instructions that are executable by the UI processor 50 to compute the upper glucose limit value, UBGL. Illustratively, the upper blood glucose limit, UBGL, is a sum of all active delta BG values stored in the correction records database 71, the active meal increase value stored in the meal correction database 69 and the target blood glucose value of the current time block. The delta BG values stored in the correction records database 71 illustratively correspond to differences in the measured BG values and the upper BG values for each active record. The delta BG values and the active meal increase value have shapes or decay curves that are determined by comparing the date and time difference of the current BG/Diary record to the corresponding start times of the correction records and the meal correction record. If any date and time difference is less than a respective offset time, the entire delta BG or meal increase value is used. If, however, any date and time difference exceeds a respective offset time, a scaled delta BG value and meal increase value is computed using a decay equation.

The process illustrated in FIGS. 14A and 14B begins at step 352 where the UI processor 50 is operable to set the upper blood glucose value, UBGL, the target value for the current time window, TV, the meal increase value, MI, and a delta blood glucose value, DBG, equal to zero. Thereafter at step 354, the UI processor 50 is operable to set a counter, K, equal to 1. Thereafter at step 356, the UI processor 50 is operable to determine whether the Kth correction record, CR(K), in the correction records database 71 is active as described above. If so, the illustrated process advances to step 358 where the UI processor 50 is operable to set a time value, TIME, equal to the time stamp of the current BG value less the start time of the Kth correction record, CST(K). Thereafter at step 360, the UI processor 50 is operable to determine whether the computed time value, TIME, is less than or equal to an offset time of the Kth correction record, COT(K), where COT for any K corresponds to an offset between the start time of the correction record and a corrected start time that may result from synchronization of the current time of the remote electronic device 12 with a reference time source, e.g., the current time of the pump 14. In any case, if the UI processor 50 determines at step 360 that the computed time value, TIME, is less than or equal to COT(K), the illustrated process advances to step 362 where the UI processor 50 is operable to compute the delta blood glucose value, DBG, as a sum of the current value of DBG and the delta BG value of the Kth correction record, CDBG(K). If, at step 360, the UI processor 50 instead determines that the computed time value, TIME, is not less than or equal to COT(K), the illustrated process advances to step 364 where the UI processor 50 is illustratively operable to compute the delta blood glucose value, DBG, as a sum of the current value of DBG and the quantity {CDBG(K)*[CAT(K)−TIME]}/[CAT(K)−COT(K)], where CAT(K) is the active time of the Kth correction record, i.e., the time duration that the Kth correction record is active. From either of steps 362 and 364, and also from the "NO" branch of step 356, the illustrated process advances to step 366 where the UI processor 50 is operable to determine whether the counter K has reached the last active record in the correction records database 71. If not, the process advances to step 368 where the UI processor increments the counter value K, and then proceeds back to the beginning of step 356.

Following the "YES" branch of step 366, the delta BG value, DBG, represents the sum of the DBG values of each of the active records in the correction records database 71. Step 366 advances to step 370 where the UI processor 50 is operable to compute a rounded delta BG value, e.g., by using a conventional truncate function TRUNC[DBG+0.5]. Thereafter at step 372, the UI processor 50 is operable to check the status of the meal correction record to determine whether it is active. If so, the illustrated process advances to step 374 where the UI processor 50 is operable to set the time value, TIME, equal to the time stamp of the current BG value less the start time of the meal correction record, MCST. Thereafter at step 376, the UI processor 50 is operable to determine whether the computed time value, TIME, is less than or equal to an offset time of the meal correction record, MCOT, where MCOT corresponds to an offset between the start time of the meal correction record and a corrected start time that may result from synchronization of the current time of the remote electronic device 12 with a reference time source, e.g., the current time of the pump 14. In any case, if the UI processor 50 determines at step 376 that the computed time value, TIME, is less than or equal to MCOT, the illustrated process advances to step 378 where the UI processor 50 is operable to set the meal increase value, MI, equal to the meal correction increase, MCI, of the meal correction record. If, at step 376, the UI processor 50 instead determines that the computed time value, TIME, is not less than or equal to MCOT, the illustrated process advances to step 380 where the UI processor 50 is operable to compute the meal increase value, MI, according to the equation {MCI*[MCAT−TIME]}/[MCAT−MCOT], where MCAT is the active time of the meal correction record, i.e., the time duration that the meal correction record is active. Thereafter at step 382, the UI processor 50 is illustratively operable to compute a rounded MI value using the truncate function described above. From either of steps 378 and 382, and also from the "NO" branch of step 372, the illustrated process advances to step 384 where the UI processor 50 is illustratively operable to compute a target blood glucose value according to the equation [UT(TB)−LT(TB)]/2, where UT(TB) is the upper blood glucose target value for the current time block and LT(TB) is the lower blood glucose target value for the current time block, and to then compute a rounded target blood glucose value using the truncate function described above to produce a resulting target blood glucose value, TV. Thereafter at step 386, the UI processor 50 is operable to compute the upper blood glucose limit, UBGL, as a sum of DBG, MI and TV. Thereafter at step 38, the processor 50 is operable to determine whether the upper blood glucose value, UBGL, which was computed at step 386 is greater than a predefined high upper blood glucose limit, $UBGL_H$. If so, the illustrated process is aborted and the UI processor 50 is operable at step 390 to control the display unit 18 to display a suitable warning message. If, at step 388, the UI processor 50 determines that UBGL is not greater than $UBGL_H$, the illustrated process is returned to step 342 of the process of FIG. 12.

Figure 15:
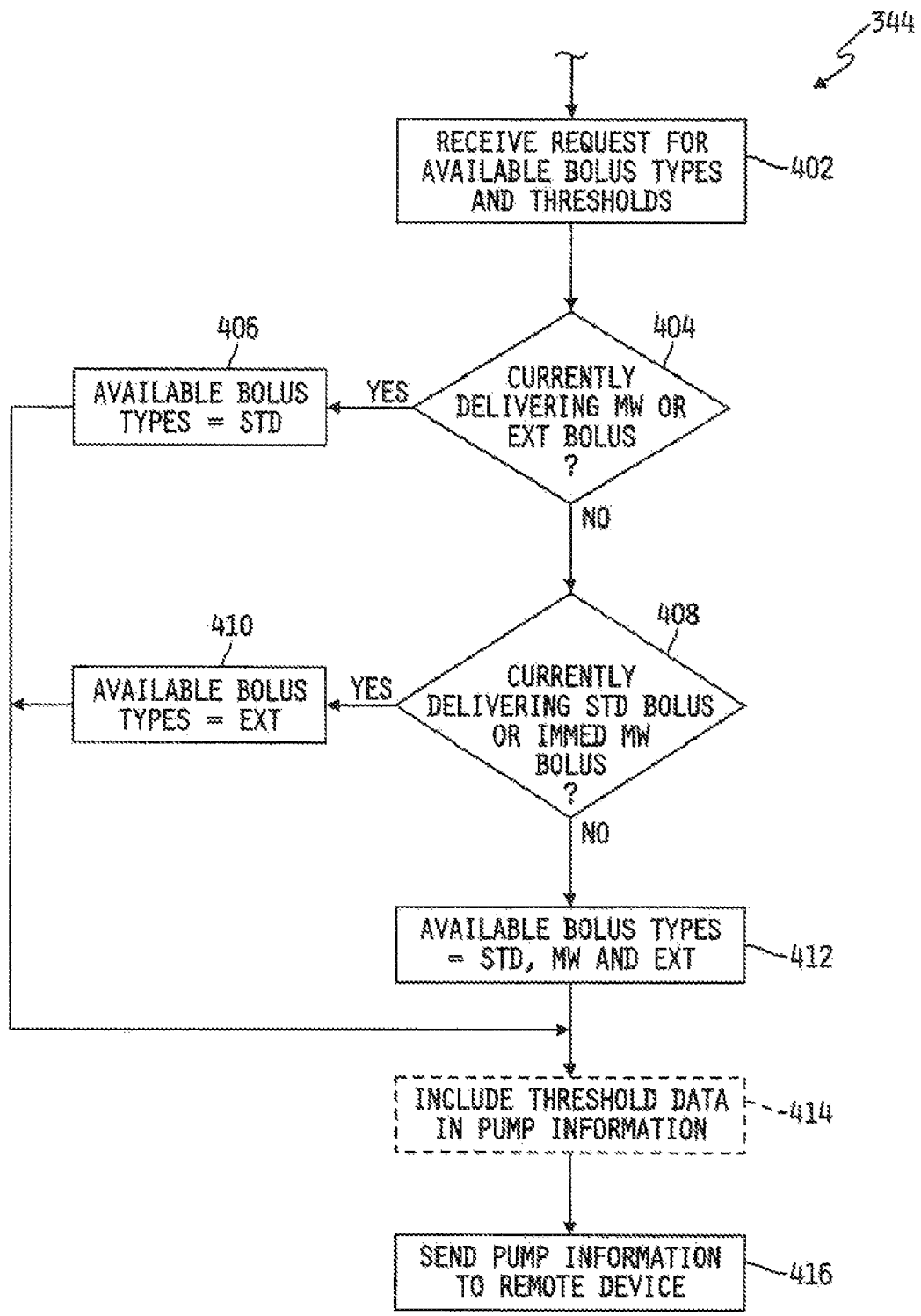
FIG. 15 shows a flowchart of one illustrative embodiment of a process carried out by an infusion pump to determine and wirelessly transfer current pump operating information to a remote electronic device.

Referring again to FIG. 12, the illustrated process advances from step 342 to step 344 where the UI processor 50 is operable to obtain currently available bolus types, bolus thresholds and the like from the liquid infusion pump 14. In one illustrative embodiment, the remote electronic device 12 is operable at step 344 to wirelessly send a pump information request to the liquid infusion pump, and the pump 14, upon receiving this request, is operable to determine currently available bolus types, bolus thresholds and the like, and to then transmit this pump information to the remote electronic device 12. Referring now to FIG. 15, a flowchart is shown of one illustrative process that is carried out by the pump 14 to determine and transfer current pump operating information to the remote electronic device 12. Illustratively, the process is stored in the memory unit 25 of the pump 14 in the form of instructions that are executable by the processor 28 of the pump 14 to determine and transfer the current operating conditions of the pump 14. The available bolus types can vary for each execution of the process illustrated in FIG. 15, and the bolus types that are available during any execution of the illustrated process depends upon the current status of the pump 14 when the illustrated process is executed.

The illustrated process begins at step 402 where the processor 28 is operable to receive the request for available bolus type and threshold information from the remote electronic device 12. Thereafter at step 404, the processor 28 is operable to determine whether pump 14 is currently delivering an Extended or Multi-wave bolus. In this embodiment, the liquid infusion pump 14 is not capable of concurrently delivering multiple extended or multi-wave boluses, or of concurrently delivering an extended bolus and a multi-wave bolus, and the illustrated process accordingly advances to step 406 where the processor 28 is operable to mark as available bolus types only the standard bolus, STD.

If, at step 404, the processor 28 determines that the pump 14 is not currently delivering an Extended or a Multi-wave bolus, the illustrated process advances to step 408 where the processor 28 is operable to determine whether the pump 14 is currently delivering a standard bolus or an immediate portion of a Multi-wave bolus. In this embodiment, the insulin infusion pump 14 is not capable of concurrently delivering a Standard or Multi-wave bolus while currently delivering a Standard bolus, or of concurrently delivering a Standard bolus while delivering the immediate portion of a Multi-wave bolus, and the illustrated process accordingly advances to step 410 where the UI processor 50 is operable to mark as available types of boluses only the extended bolus, EXT. If, at step 408, the processor 28 determines that the pump 14 is not currently delivering a standard bolus or an immediate portion of a Multi-wave bolus, the processor 28 is operable at step 412 to mark as available each of the Standard, Extended and Multi-wave boluses. From any of steps 406, 410 and 412, the illustrated process advances to step 414 where the processor 28 is operable to include bolus threshold information in the pump information to be sent to the remote electronic device. Step 414 is illustratively shown in dashed-line representation to indicate that step 412 may or may not be executed each time that the process illustrated in FIG. 15 is executed. At times at which step 414 is executed, he available bolus threshold information may illustratively includes a maximum bolus value or bolus limit value that corresponds to a maximum bolus amount that can be delivered by the pump 14. Illustratively, the available bolus threshold information may further include a minimum bolus amount that corresponds to a minimum bolus amount that can be delivered by the pump 14 for a Multi-wave bolus, e.g., 2/10 U. Illustratively, the available bolus threshold information may further include a maximum bolus duration and duration step, and may further include durations of the last EXT and MW boluses delivered as well as the last MW fast amount delivered by the pump 14. In any case, the illustrated process advances to step 416 where the processor 28 of the pump is operable to send, via the wireless communication circuit 30, the current pump information to the remote electronic device.

Referring again to FIG. 12, completion of the step 344 of the illustrated process returns to step 322 of the process 300 illustrated in FIG. 10A. Referring again to FIG. 10A, step 322 of the process 300 advances to step 324 where the UI processor 50 is operable to determine whether the pump history and/or bolus threshold and/or pump status information was updated at step 322. If not, the process 300 advances to step 326 where the processor 50 is operable to control the display device 18 to display a warning message on the bolus advice screen that one or more bolus advice values and/or an active insulin may not be based on current drug pump operating history. From step 326, and from the "YES" branch of step 324, the process 300 advances to step 328 where the processor 50 is operable to compute the active insulin value, AI.

The active insulin value, AI, is illustratively calculated from the active data records in the correction records database 71 and the current date and time of the remote electronic device 12. Generally, the active insulin calculation process entails adding together the correction boluses of the active records using the differences between the current date/time of the remote electronic device 12 and the correction offset times and the correction end times of each of the active records. If any date and time difference is less than the correction offset time, the entire correction bolus is used. However, if a date and time difference exceeds the correction offset time, a scaled correction bolus is calculated using decay equation.

Figure 16:
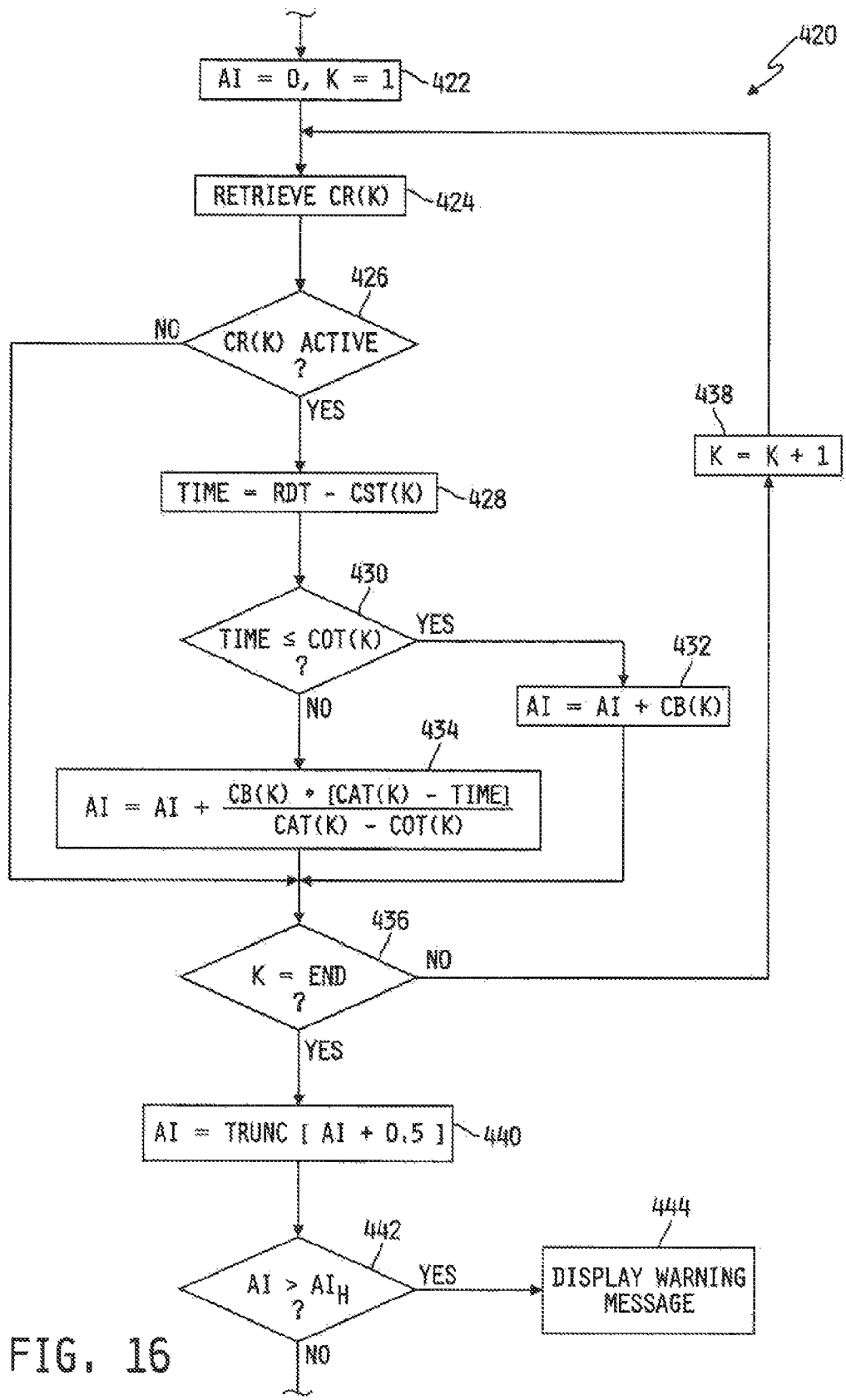
FIG. 16 shows a flowchart of one illustrative embodiment of a process carried out by the remote electronic device for determining an active insulin value corresponding to an amount of insulin currently active in a body of a user.

Referring now to FIG. 16, a flowchart is shown of one illustrative embodiment of a process 420 for computing active insulin, AI. Illustratively, the process 420 is stored in the memory unit 66 in the form of instructions that are executable by the UI processor 50 to compute the active insulin value, AI. The illustrated process begins at step 422 where the UI processor 50 is operable to set the initial value of active insulin, AI, equal to zero and to set a counter value, K, equal to 1. Thereafter at step 424, the UI processor 50 is operable to retrieve the Kth record from the correction records database 71. Thereafter at step 426, the UI processor 50 is operable to determine whether the Kth correction record is an active record. If so, the illustrated process advances to step 428 where the UI processor 50 is operable to compute a time value, TIME, as the current remote electronic device time, RDT, less the correction start time of the Kth correction record, CST(K). Thereafter at step 430, the UI processor 50 is operable to determine whether the computed time value, TIME, is less than or equal to the correction offset time of the Kth correction record, COT(K). If so, the UI processor 50 is operable at step 432 to compute the active insulin value, AI, as a sum of the current active insulin value, AI, and the correction bolus value of the Kth correction record, CB(K). If, at step 430, the UI processor 50 instead determines that the computed time value, TIME, is not less than or equal to the offset time, COT(K), the UI processor is operable at step 434 to compute the active insulin value, AI, as a sum of the current active insulin value, AI, and the quantity $\{CB(K)*[CAT(K)-TIME]\}/[CAT(K)-COT(K)]$, where CAT(K) is the active time of the Kth correction record.

The steps 432 and 434, and the "NO" branch of step 426, all advance to step 436 where the UI processor 50 is operable to determine whether the current count value, K, corresponds to the last active record in the correction records database 71. If not, the illustrated process advances to step 438 where the UI processor 50 is operable to increment the counter value, K, by one, and the process thereafter loops back to step 424. Following the "YES" branch of step 436, the UI processor 50 is operable at step 440 to compute a rounded active insulin value using the truncation function referred to hereinabove, and thereafter at step 442 the UI processor 50 is operable to determine whether the computed active insulin value, AI, is greater than a predefined high active insulin value, $AI_H$. If so, the illustrated process advances to step 444 where the AI calculation process is aborted and the UI processor 50 is operable to control the display device 18 to display a suitable warning message. If, at step 442, the UI processor 50 determines that AI is not greater than $AI_H$, the illustrated process is returned to step 328 of the process 300 of FIG. 10A with a computed value of AI.

Figure 17:
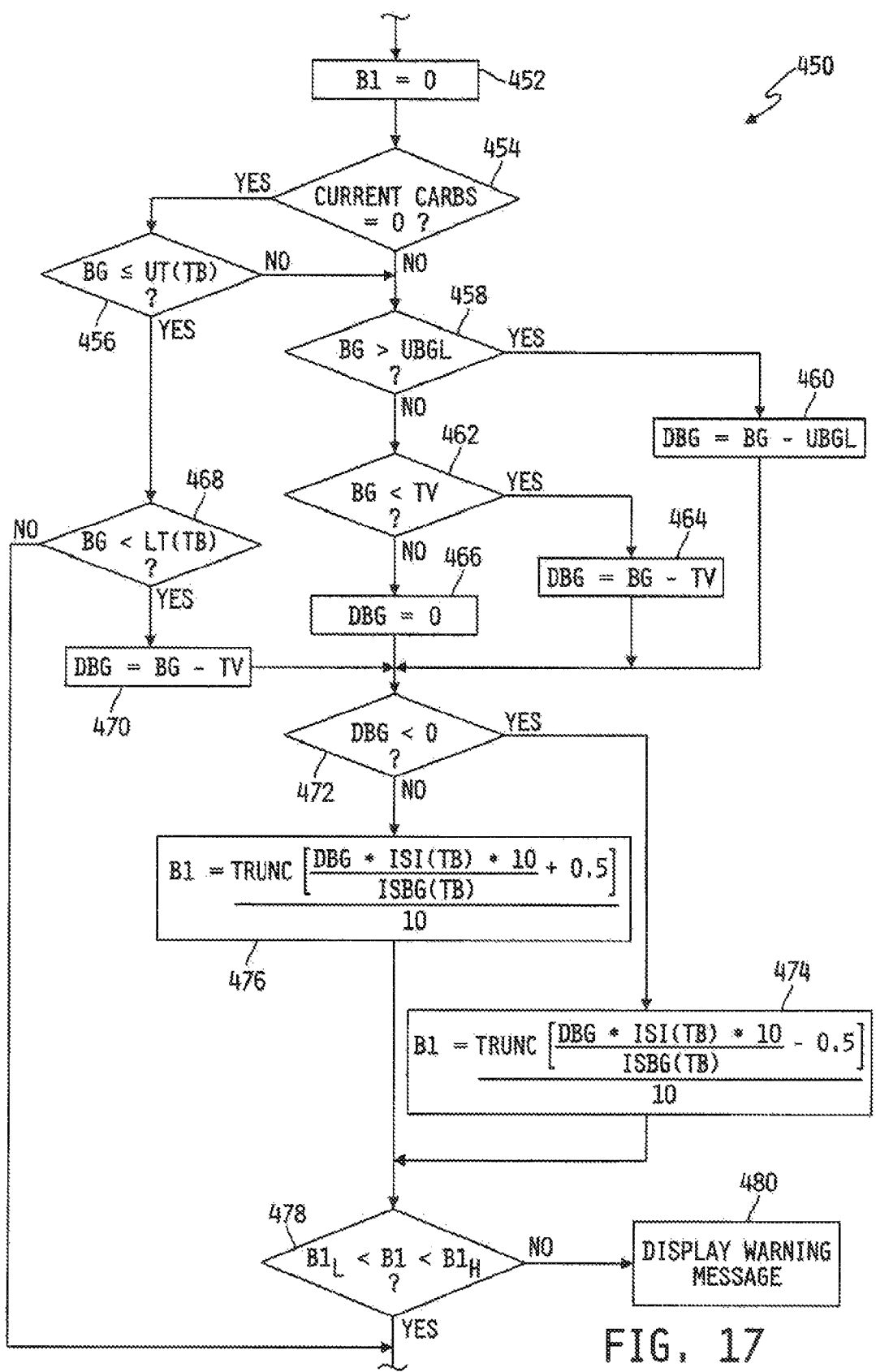
FIG. 17 shows a flowchart of one illustrative embodiment of a process carried out by the remote electronic device for determining a recommended bolus amount based on blood glucose measurements and on infusion pump operating information.

Step 328 of the process 300 advances to step 330 where the UI processor 50 is operable to compute first, second and third bolus value, B1, B2 and B3. Each of the bolus values are computed using different information, and during any bolus advice session one or more of the computed bolus values may be positive, negative or zero. Referring now to FIG. 17, a flowchart is shown of one illustrative embodiment of a process 450 for computing a first one of the bolus values, B1, which is illustratively based on a recent blood glucose value and also on pump operating history data. The process 450 is illustratively stored in the memory unit 66 in the form of instructions that are executable by the UI processor 50 to determined the bolus amount B1. The illustrated process begins at step 452 where the UI processor is operable to initially set B1 equal to zero. Thereafter at step 454, the UI processor 50 is operable to determine whether the measured BG value is accompanied by any consumed carbohydrate value. If so, the current carbs do not equal zero and the process 450 advances to step 458 where the UI processor 50 is operable to determine whether the measured BG value, BG, is greater than the current upper blood glucose limit, UBGL. If so, the illustrated process advances to step 460 where the UI processor 50 is operable to compute a delta blood glucose value, DBG, as the measured BG value, BG, less the upper blood glucose limit, UBGL. If, at step 458, the UI processor 50 instead determines that BG is not greater than UBGL, the UI processor 50 is thereafter operable at step 462 to determine whether the measured BG value, BG, is less than the current target blood glucose value, TV. If so, the UI processor 50 is thereafter operable at step 464 to compute the delta blood glucose value, DBG, as the measured BG value, BG, less the target blood glucose value, TV. Otherwise, if the UI processor 50 determines at step 462 that BG is not less than TV, the illustrated process advances to step 466 where the UI processor 50 is operable to set DBG=0.

If, at step 454, the UI processor 50 determines that the measured BG value is not accompanied by a carbohydrate value, the illustrated process advances to step 456 where the UI processor 50 is operable to determine whether the measured blood glucose value, BG, is less than or equal to the upper blood glucose threshold for the current time block, UT(TB). If so, the illustrated process advances to step 468 where the UI processor 50 is operable to determine whether the measured blood glucose value, BG, is less than or equal to the lower blood glucose threshold for the current time block, LT(TB). If not, the UI processor 50 exits the illustrated process with B1=0 since the measured blood glucose value, BG, is within the target range for the current time block. If, at step 468, the UI processor 50 instead determines that BG is less than LT(TB), the illustrated process advances to step 470 where the UI processor 50 is operable to compute the delta blood glucose value, DBG, as the measured BG value, BG, less the target blood glucose value, TV.

Following any of steps 460, 464, 466 and 470, the illustrated process advances to step 472 where the UI processor 50 is operable to determine whether the computed delta blood glucose value, DBG, is less than zero. If so, the UI processor 50 is illustratively operable at step 474 to compute B1 according to the equation (DBG*ISI(TB)*10)/ISBG(TB), to computed a rounded down value of this using the truncate function referred to hereinabove, and to then divide the result by 10. If, at step 472, the UI processor 50 instead determines that DBG is not less than zero, the illustrated process advances to step 476 where the UI processor 50 is illustratively operable at step 476 to compute B1 according to the equation (DBG*ISI (TB)*10)/ISBG(TB), to compute a rounded value of this using the truncate function, and to then divide the result by 10. In each case, ISI(TB) corresponds to an insulin sensitivity insulin value for the current time block and ISBG corresponds to an insulin sensitivity blood glucose value for the current time block. In any case, both of the steps 474 and 476 advance to step 478 where the UI processor 50 is operable to determine whether the computed bolus value, B1, is between predefined low and high bolus values, $B_L$ and $B_H$ respectively. If not, the illustrated process is aborted and the UI processor 50 is operable at step 480 to control the display device 18 to display a suitable warning message. If, at step 478, the UI processor 50 determines that B1 is not between $B_L$ and $B_H$, the illustrated process is returned to step 330 of the process 300 of FIG. 10A with a computed value of B1.

Figure 18:
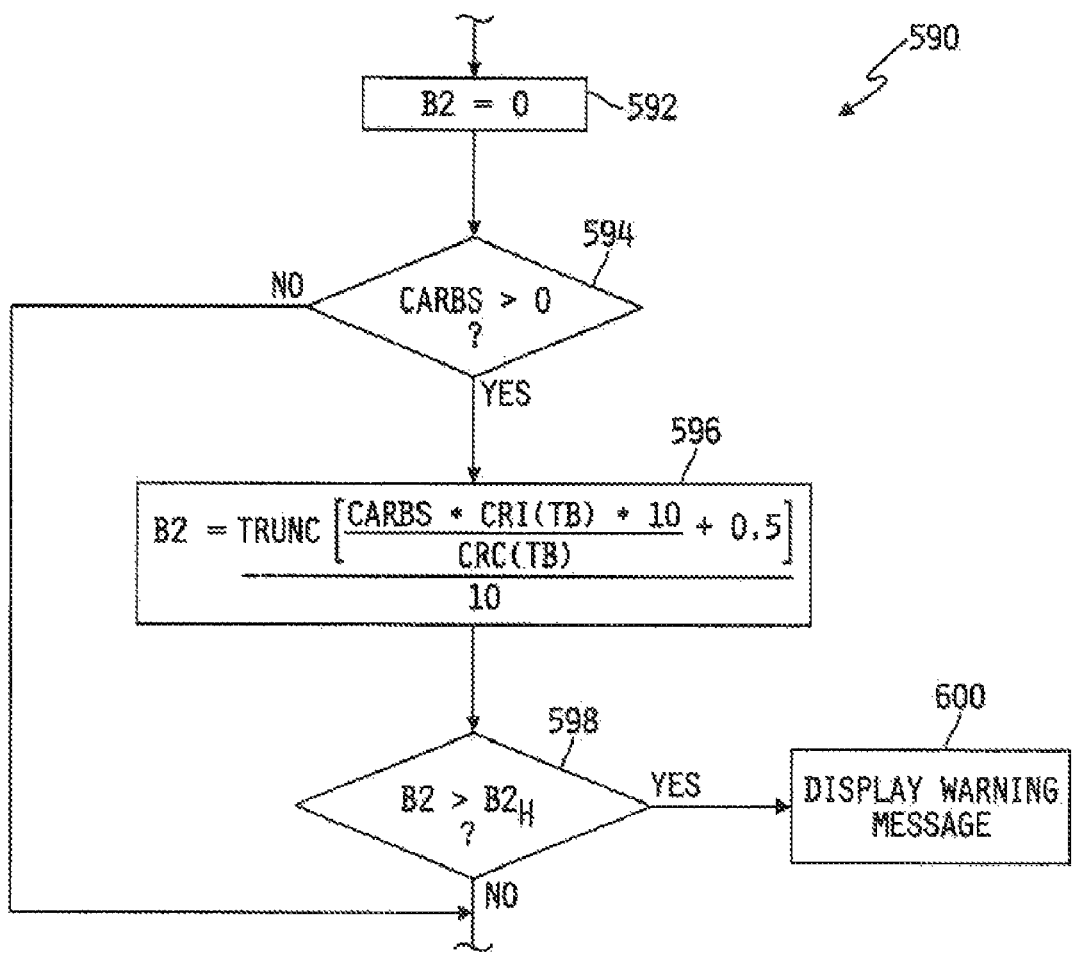
FIG. 18 shows a flowchart of one illustrative embodiment of a process carried out by the remote electronic device for determining a recommended bolus amount based on carbohydrate intake by a user.

Also at step 330, the UI processor 50 is operable to compute a second bolus value, B2, that is illustratively based on GARB values entered by the user that correspond to carbohydrates that the user has taken or is planning to take. Referring to FIG. 18, a flowchart is shown of one illustrative embodiment of a process 590 for computing B2. Illustratively, the process 590 shown in FIG. 18 is stored in the memory device 66 of the remote electronic device 12 in the form of instructions that are executable by the UI processor 50 to determine B2. The illustrated process begins at step 592 where the UI processor 50 is operable to set an initial value of B2=0. Thereafter at step 594, the UI processor 50 is operable to determine whether the CARBS value provided by the user at step 436 of the process 400 is greater than zero. If so, the illustrated process advances to step 596 where the UI processor 50 is operable to compute B2 according to the equation [CARBS*CRI(TB)*10]/CRC(TB), to computed a rounded value of this using the truncate function, and to divide this result by 10, where CRI(TB) is a carbohydrate ratio of insulin for the current time block and CRC(TB) is a carbohydrate ratio of carbohydrates for the current time block. The resulting value, B2, is the bolus value based on the carbohydrate value of a meal or snack, and the illustrated process advances from step 596 to step 598 where the UI processor 50 is operable to determine whether the computed bolus value, B2, is greater than a predefined high bolus value, $B2_H$. If so, the illustrated process advances to step 600 where the B2 calculation process is aborted and the UI processor 50 is operable to control the display device 18 to display a suitable warning message. If, at step 598, the UI processor 50 determines that B2 is not greater than $B2_H$, the illustrated process is returned to step 330 of the process 300 of FIG. 10A with a computed value of B2.

Figure 19:
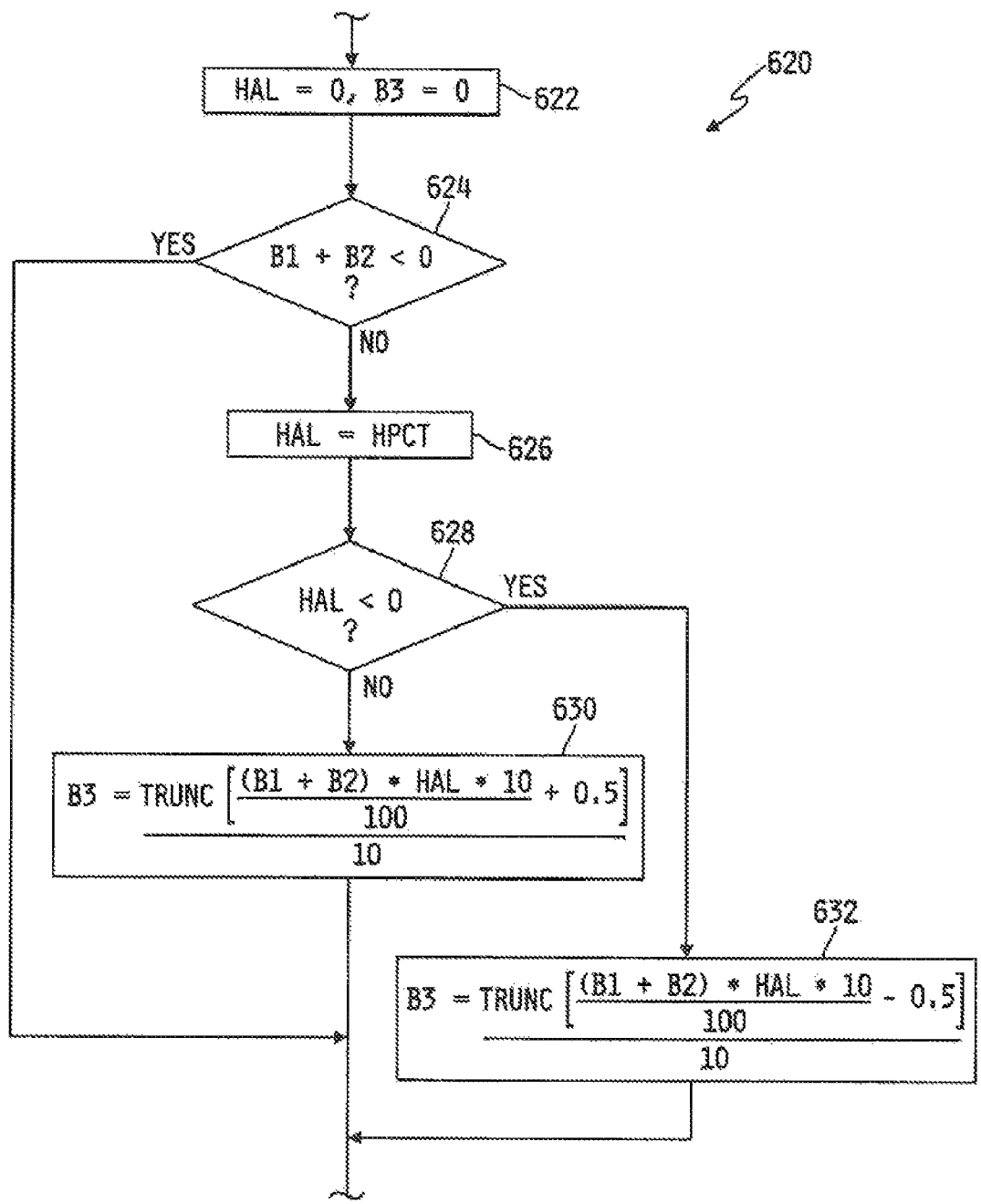
FIG. 19 shows a flowchart of one illustrative embodiment of a process carried out by the remote electronic device for determining a recommended bolus amount based on user supplied health information.

Further at step 330, the UI processor 50 is operable to compute a third bolus value, B3, which is illustratively based on health information entered by the user that corresponds to a current health state of the user. Illustratively, the health choices may include, for example, but should not be limited to, no entry, one or more exercise options, an illness option and a sickness option, although more, fewer and/or different options may alternatively be available. In this embodiment, the user may define percentage values associated with each of the health event options during the device set up process. Referring now to FIG. 19, a flowchart is shown of one illustrative embodiment of a process 620 for computing B3. Illustratively, the process 620 is stored in the memory device 66 of the remote electronic device 12 in the form of instructions that are executable by the UI processor 50 to compute B3. The illustrated process begins at step 622 where the UI processor 50 is operable to set an initial value of a health adjustment level, HAL, equal to zero and to also set an initial value of B3=0. Thereafter at step 624, the UI processor 50 is operable to determine whether the bolus quantity B1+B2 is less than zero. If not, the illustrated process advances to step 626 where the UI processor 50 is operable to set the health adjustment level, HAL, equal to a health percentage value, HPCT, that is illustratively a programmable value that may be positive, e.g., for exercise-related health adjustment activities, or negative, e.g., for illness or stress. In any case, the illustrated process advances from step 626 to step 628 where the UI processor 50 is operable to determine whether HAL is less than zero. If so, the UI processor is operable at step 632 to compute B3 according to the equation [(B1+B2)*HAL*10]/100, to compute a rounded down value of this using the truncate function, and to divide this result by 10. If at step 628, the UI processor 50 instead determines that HAL is not less than zero, the process advances to step 630 where the UI processor is operable to compute B3 according to the equation [(B1+B2) *HAL*10]/100, to compute a rounded value of this using the truncate function, and to divide this result by 10. In either case, the resulting value, B2, is the bolus value based on the carbohydrate value of a meal or snack, and the illustrated process advances from either of steps 630 and 632, and also from the "YES" branch of step 624, back to step 330 of the process 300 illustrated in FIG. 10A with computed value of B3.

Figure 20:
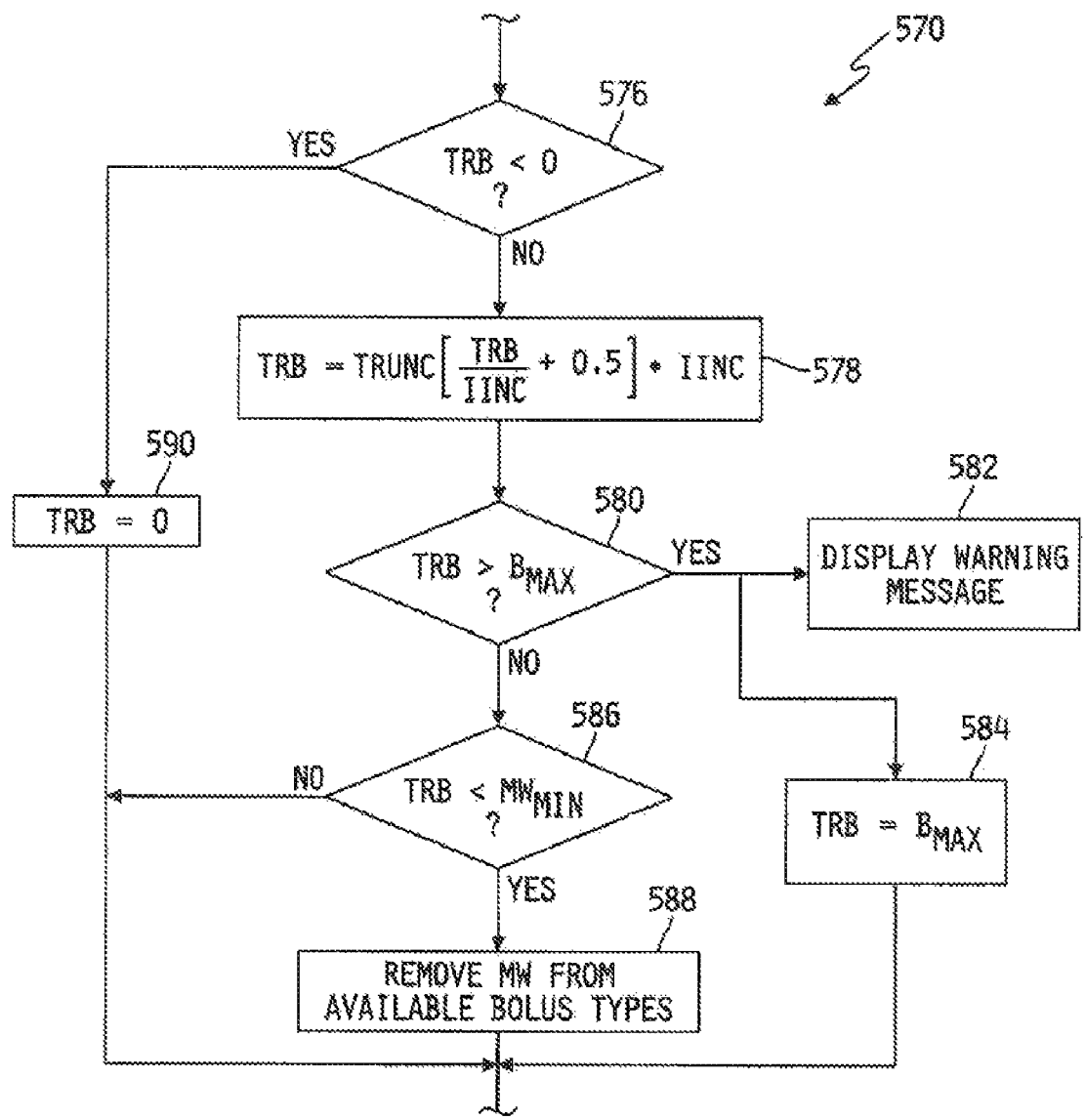
FIG. 20 shows a flowchart of one illustrative embodiment of a process carried out by the remote electronic device for determining a total recommended bolus amount based on the recommended bolus amounts determined by the processes of FIGS. 14, 16 and 17.

The process 300 illustrated in FIG. 10A advances from step 330 to step 332 where the UI processor is operable to compute a total recommended bolus value, TRB, based on B1-B3. Referring now to FIG. 20, a flowchart is shown of one illustrative embodiment of a process 570 for carrying out step 332 of the process 300 illustrated in FIG. 10A. Illustratively, the process 570 shown in FIG. 20 is stored in the memory device 66 of the remote electronic device 12 in the form of instructions that are executable by the UI processor 50 to determine TRB. The process 570 begins at step 576 where the UI processor 50 is operable to determine whether the computed total bolus value, TRB, is less than zero. If not, the illustrated process advances to step 578 where the UI processor 50 is operable to compute TRB as a product of a rounded value of TRB/IINC using the truncation function, and IINC, where IINC is an insulin increment value.

The illustrated process advances from step 578 to step 580 where the UI processor 50 is operable to determine whether TRB computed at step 578 is greater than a maximum bolus value, e.g., received from the pump 14 during the process illustrated in FIG. 15. If so, the UI processor 50 is operable at step 582 to control the display unit 18 to display a suitable warning message. The "YES" branch of step 580 also advances to step 584 where the UI processor 50 is operable to set the total recommended bolus, TRB, equal to the maximum bolus value, $B_{MAX}$. If, at step 580, the UI processor 50 is instead operable to determine that TRB is not greater than the maximum bolus value, $B_{MAX}$, the process 570 advances to step 586 where the UI processor 50 is operable to determine whether TRB is less than a minimum Multi-wave bolus duration, $MW_{MIN}$. If so, the illustrated process advances to step 588 where the UI processor 50 is operable to remove MW from the available bolus types determined by the process of FIG. 12.

If, at step 576, the UI processor 50 determines that TRB is less than zero, the illustrated process advances to step 590 where the UI processor 50 is operable to set TRB=0. From any of steps 584, 588 and 590, the process 570 returns to step 332 of the process 300 illustrated in FIG. 10A. Referring again to FIG. 10A, the process 300 advances from step 332 to step 334 where the UI processor 50 is operable to control the display device 18 to display a bolus advice screen that shows the active insulin value, AI, any recent blood glucose value, BG, a BG color indicator as described with respect to step 312, B1–B3, TRB and a bolus type, e.g., standard (STD), multi-wave (MW), extended (EXT), each of which may be used to automatically program the pump 14 from the remote electronic device 12, and two manual types. In one embodiment, if a blood glucose measurement, BG, has been conducted within a predefined time period prior to executing step 334, the UI processor 50 is operable at step 334 to display the bolus advice screen showing the measured blood glucose value, BG. Otherwise, the UI processor 50 may be illustratively operable at step 334 to display "bG Test" on the screen where a BG value would be shown if a current BG value was available. In any case, the process 300 advances from step 334 to a sub-process B.

Referring now to FIG. 13, a graphic example is shown of one illustrative embodiment of a bolus advice display screen 301 produced by the process 300 of FIG. 10A at step 334. In the illustrated example, a Bolus Advice label 303 appears at the top of the screen 301 to indicate that the user is executing the bolus advice feature. A blood drop symbol appears next to the displayed blood glucose value 305, e.g., 120 mg/dl, and a color bar 309, providing a visual indication of the blood glucose value 305 relative to an acceptable blood glucose range and/or a number of blood glucose limits, is positioned next to the blood glucose value 305. The active insulin value 307, e.g., −2 U, is positioned under the blood glucose value 305, and a bolus value 311, corresponding to the bolus value B1, is displayed adjacent to the active insulin value 307. As described above, if the bolus advice screen 301 was generated when a recently measured blood glucose value, BG, was not available, the value 120 mg/dL would illustratively be replace by the phrase bG Test.

An apple symbol is used to identify a carbohydrates field 313, and a heart symbol is used to identify a health field 315.

A bolus type indicator 319 appears below the health field 315 and the total recommended bolus value 317, e.g., 3 U, is displayed adjacent to the bolus type indicator 319. A bolus type 321, e.g., Standard, is displayed below the total recommended bolus 317. At the bottom of the screen between Cancel and Confirm inputs, a BlueTooth® symbol 323 is provided to indicate the connection status of the wireless communication link with the insulin infusion pump 14, e.g., solid when a wireless connection exists and otherwise flashing.

Referring now to FIGS. 10B and 10C, the sub-process B identified after step 334 of FIG. 10A, is shown, wherein the sub-process B forms part of the bolus advice process 300. It will be observed that the sub-process B includes a number of processes that may each be accessed independently any number of times. For example, the sub-process B includes a process 500 for measuring a blood glucose value and computing a bolus amount, B1 that corresponds to the BG measurement. In the illustrated embodiment, the process 500 begins at step 502 where the UI processor 50 is operable to determine whether a strip insert, e.g., insertion of a blood glucose strip into the carrier port 20 of the remote electronic device 12, has been detected or if the user has selected the bG Test field if this field is displayed in place of a blood glucose value as described above. If not, the process 500 loops back to the beginning of step 502. If, at step 502, the UI processor 50 determines that a strip insert or user selection of the bG Test field has been detected, the process 500 advances to step 504 where the UI processor 50 is operable to conduct a blood glucose test, e.g., by prompting and guiding a user through such a BG test as described above, which returns a measured blood glucose value, BG. Thereafter at step 506, the UI processor 50 is operable to execute the hypoglycemic test process 314 illustrated in FIG. 11 and described above. If the hypoglycemic test process 314 returns a value RETURN, this indicates that the blood glucose value is too low to recommend a bolus value and the process 500 advances to step 514 where the UI processor 50 is operable to exit the bolus advice feature and display the main menu 302. If the hypoglycemic test process 314 instead returns the value ADVANCE, the process 500 advances to step 508 where the UI processor 50 is operable to compute all of the bolus values, B1–B3, e.g., as illustrated and described herein. In the illustrated embodiment, measured and/or user entered value may have an effect on one or more of the bolus values, B1–B3, and the UI processor 50 is accordingly operable in sub-process. B to re-compute each bolus value, B1–B3, after each BG measurement, Carbohydrate entry or health entry. In any case, following step 508 the UI processor 50 is operable at step 510 to compute a total recommended bolus value, TRB, e.g., as illustrated and described herein. Thereafter at step 512, the UI processor 50 is operable to update the bolus advice screen with BG, a BG color indicator as described above, B1–B3 and TRB. From step 512, the process 500 loops back to the beginning of the sub-process B.

The sub-process B of FIG. 10B further includes a process 520 for entering a carbohydrate value of a meal or snack that has just been, or is planned to be taken, and determining a bolus value based on the entered carbohydrate value. The process 520 begins at step 522 where the UI processor 50 is operable to determine whether a user has selected the CARB field of the displayed bolus advice screen. If not, the process 520 loops back to the beginning of step 522. If user selection of the CARES field is detected at step 522, the process 520 advances to step 524 where the processor 50 is operable to determine whether a carbohydrate value relating to a meal or snack that was just, or is planned to be, taken, has been entered by the user. If not, the process 520 loops back to the beginning of step 524. In one embodiment, the user at step 524 may manually enter a carbohydrate value into the remote electronic device 12, e.g., via the user buttons 16, that corresponds to a carbohydrate content of the meal or snack that was just taken or is planned to be taken. In an alternative embodiment, selection by the user of the carbohydrate value field displayed by the UI processor 50 on the display device 18 at step 522 may take the user to a menu-driven food database via which the user may select the various food items that comprise the meal or snack. In this embodiment, the menu-driven food database is operable to compute a total carbohydrate value based on the individual carbohydrate values of the food items selected by the user from the food database, and the UI processor 50 is operable at step 524 to automatically enter the total carbohydrate value determined by the menu-driven food database process into the carbohydrate value field displayed on the display device 18 at step 524. In any case, if the user has entered a carbohydrate value that is detected by the UI processor 50 at step 524, the process 520 advances to step 526 where the UI processor 50 is operable to re-compute each of the bolus values B1–B3, e.g. as illustrated and described herein. Thereafter at step 528, the UI processor 50 is operable to compute the total recommended bolus, TRB, e.g., as illustrated and described herein. Thereafter at step 530, the UI processor 50 is operable to control the display device 18 to update the bolus advice display screen to include the carbohydrate value provided by the user at step 524 to display the computed bolus values, B1–B3, determined at step 526 and to display the updated total recommended bolus value, TRB. The process 520 loops from step 530 back to the beginning of the sub-process B.

The sub-process B of FIG. 10B further includes a process 540 for entering health information, and determining a bolus value based on the entered health information. The process 540 begins at step 542 where the UI processor 50 is operable to determine whether a user has selected the Health field of the displayed bolus advice screen. If not, the process 540 loops back to the beginning of step 542. If user selection of the Health field is detected at step 542, the process 540 advances to step 544 where the processor 50 is operable to determine whether a Health value has been entered by the user. If not, the process 540 loops back to the beginning of step 544. In one embodiment, when the user manually selects at step 542 the health event field displayed on the display device 18 by the UI processor 50, the UI processor 50 is operable to control the display device 18 to display a plurality of health event choices. The health event choices may include, for example, but should not be limited to, no entry, one or more exercise options, an illness option and a sickness option, although more, fewer and/or different options may alternatively be available. In this embodiment, the user may define percentage values associated with each of the health event options during the device set up process such that when the user manually selects one of the health event options at step 544, the UI processor 50 is operable thereafter at step 546 to re-compute the bolus values B1-B3, e.g., as illustrated and described herein. Thereafter at step 548, the UI processor 50 is operable to again compute the total recommended bolus, TRB, e.g., as illustrated and described herein. The process 540 advances from step 548 to step 550 where the UI processor 50 is operable to control the display device 18 to update the bolus advice display to include the health event, the bolus values, B1–B3, and the total recommended bolus value, TRB. The process 540 loops from step 550 back to the beginning of the sub-process B.

The sub-process B of FIG. 10B further includes a process 560 that allows the user to manually modify the total recommended bolus value, TRB. The process 560 begins at step 562 where the UI processor 50 is operable to determine whether a user has selected the TRB field of the displayed bolus advice screen. If not, the process 560 loops back to the beginning of step 562. If user selection of the TRB field is detected at step 562, the process 560 advances to step 564 where the processor 50 is operable to determine whether the user has modified the TRB value. If not, the process 560 loops back to the beginning of step 564. If the processor 50 determines that the user has, at step 564, modified the TRB value, the process 560 advances to step 566 where the UI processor 50 is operable to control the display device 18 to update the bolus advice display to include the modified total recommended bolus value, TRB. The process 560 loops from step 566 back to the beginning of the sub-process B.

Referring now to FIG. 10C, the sub-process B further includes a process 640 for selecting a bolus type. The process 640 begins at step 642 where the UI processor 50 is operable to determine whether a user has selected the bolus type field of the displayed bolus advice screen. If not, the process 640 loops back to the beginning of step 642. If user selection of the bolus type field is detected at step 642, the process 640 advances to step 644 where the processor 50 is illustratively operable to display available bolus types on the bolus advice screen. In one illustrative embodiment, the available bolus types may include, but should not be limited to, a standard bolus, (STD), a multi-wave (MW) bolus, an extended (EXT) bolus, a manually programmable bolus and a manually administered bolus via an insulin pen or syringe or the like. In cases were a wireless connection between the remote electronic device 12 and 14 is or can be established, the available bolus types may illustratively include all bolus types that the pump 14 is currently capable of delivering. In other cases where a wireless connection could not be established when first entering the bolus advice process, and cannot currently be established, the available bolus types may illustratively include only manually programmable and/or manual delivery via insulin pen/syringe. Those skilled in the art will recognize more, fewer and/or different bolus types that may be made available to the user at step 644, and any such alternative or additional bolus types are contemplated by this disclosure.

Following step 644, the process 640 advances to step 646 where the UI processor 50 is operable to determine whether the user has selected a bolus type. If not, the process 640 loops back to step 644. If the processor 50 determines that the user has, at step 646, selected a bolus type, the process 640 advances to step 646 where the UI processor 50 is operable to control the display device 18 to update the bolus advice display to include the selected bolus type. The process 640 loops from step 648 back to the beginning of the sub-process B.

The sub-process B of FIG. 10C further includes a process 650 that allows the user to cancel and exit the bolus advice process. The process 650 begins at step 652 where the UI processor 50 is operable to determine whether a user has selected the Cancel function displayed on the bolus advice screen. If not, the process 650 loops back to the beginning of step 652. If user selection of the Cancel function is detected at step 652, the process 650 advances to step 654 where the processor 50 is illustratively operable to exit the bolus advice process and display the main menu 302.

The sub-process B of FIG. 10C further includes a process 670 that allows the user to confirm the diary entry including the total recommended bolus, TRB, for delivery. The process 670 begins at step 672 where the UI processor 50 is operable to determine whether a user has selected the Confirm function displayed on the bolus advice screen. If not, the process 670 loops back to the beginning of step 672. If user selection of the Confirm function is detected at step 672, the process 670 advances to step 674 where the UI processor 50 is illustratively operable to determine whether the current value of TRB is less than or equal to zero, i.e., whether the user has confirmed a null or negative bolus. If so, the process 670 advances to step 676 where the UI processor 50 is illustratively operable to store the bolus advice record, and to exit the bolus advice process and display the main menu 302.

If, at step 674, the UI processor 50 determines that TRB is not less than or equal to zero, the process 670 advances to step 678 where the UI processor 50 is operable to determine whether the user confirmation detected at step 672 is of a manual, e.g., manual pump or pen/syringe, or commanded, e.g., STD, MW or EXT, bolus. If the user confirmation is of a commanded bolus, the process 670 advances to step 680 where the UI processor 50 is operable to determine whether the remote electronic device 12 and the pump 14 are still wirelessly connected via a wireless communication link 40 (see FIG. 1). If not, the process 670 advances to step 682 where the UI processor 50 sets as the currently available bolus types only the manual bolus types, i.e., manual pump and pen/syringe, and the process 670 thereafter loops back to the beginning of the sub-process B. Thus, if the UI processor 50 determines after user confirmation of a commanded bolus, e.g., STD, MW or EXT, that a wireless connection does not or no longer exists between the remote electronic device 12 and the infusion pump 14, the process 670 returns to the bolus advice process of sub-process B where the UI processor 50 makes available as user selectable bolus types, e.g., at step 644 of the process 640, only manually deliverable bolus types, e.g., via manual programming of an infusion pump or via manual delivery via a drug pen or syringe.

If, at step 680, the UI processor 50 determines that the remote electronic device 12 and the pump 14 are still wirelessly connected, the process 670 advances to step 684 the UI processor 50 determines whether the user selected bolus type, i.e., the bolus type selected by the user at step 646, is a Standard bolus, STD. If so, the process 670 advances to a process C. If not, the process 670 advances to step 686 where the UI processor 50 is operable to determine whether the user selected bolus type, i.e., the bolus type selected by the user at step 646, is a multi-wave bolus, MW. If so, the process 670 advances to a process D. If not, the process 670 advances to a process E.

If, at step 678, the UI Processor 50 determines that the user confirmation detected at step 672 is of a manual bolus, the process 670 advances to step 688 where the UI processor 50 is operable to determine whether the confirmed bolus type is a manual pump (MP), corresponding to manually programming an infusion pump to deliver the bolus, or a pen/syringe (PS), corresponding to manual delivery of the bolus via a conventional drug-pen or syringe lithe confirmed bolus is a manual pump (MP), the process 670 advances to a process F, and if the confirmed bolus is a pen/syringe (PS), the process 670 advances to a process G.

Figure 21:
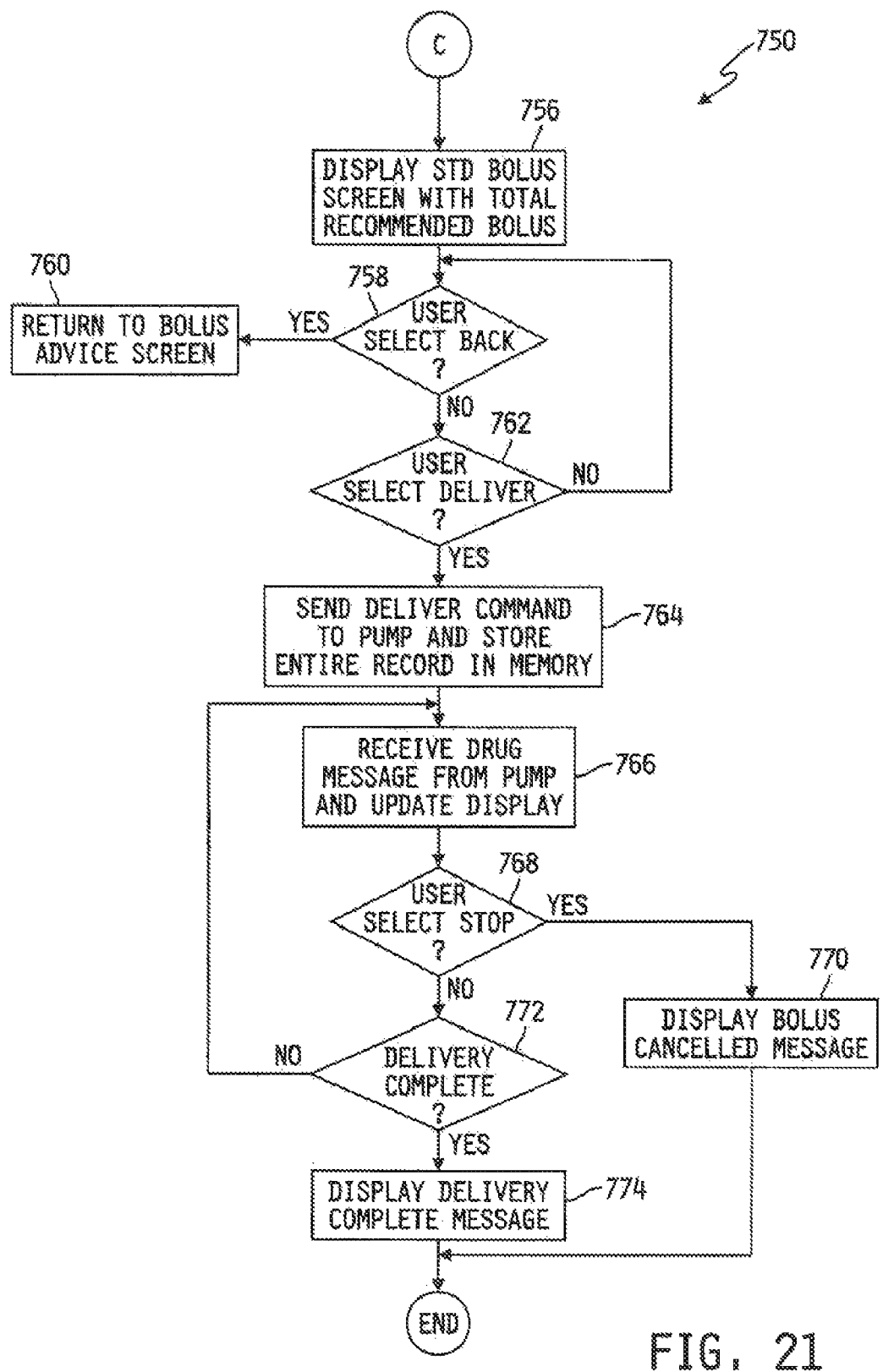
FIG. 21 shows a flowchart of one illustrative sub-process carried out by the remote electronic device in the bolus advice process of FIGS. 10A-10C.

Referring now to FIG. 21, a flowchart is shown of one illustrative embodiment 750 of the process C referred to in the process 670 of FIG. 10C. The process 750 is executed when the user has confirmed a Standard bolus of an amount TRB. The process 750 begins at step 756 where the UI processor 50 is operable to display a standard bolus confirmation screen with the total recommended bolus amount. Thereafter at step 758, the UI processor 50 is operable to determine whether the user has selected a back, i.e., go back, function that is available on the confirmation screen. If so, the process 750 advances to step 760 where the UI processor 50 returns to the bolus advice screen. If not, the process 750 advances to step 762 where the UI processor 50 is operable to determine whether the user has selected a deliver function that is available on the confirmation screen. If not, the process 750 loops back to step 760. If, at step 762, the UI processor 50 determines that the user has selected deliver on the confirmation screen, the UI processor 50 sends a deliver command to the pump 14 to which the pump is responsive to begin delivering the standard bolus in the amount of the total programmed bolus.

The process 750 advances from the "YES" branch of step 762 to step 764 where the UI processor 50 is operable to send a deliver command to the pump 14 and to store the entire record in memory. Thereafter at step 766, the processor 50 is operable to receive a wireless message from the pump 14 corresponding to an amount of the total programmed bolus that is currently being delivered. The UI processor 50 is, in turn, operable to control the display device 18 to update the total recommended bolus value, TRB, to reflect delivery by the pump 14 of the bolus amount so far delivered. For example, if at step 766 the UI processor 50 receives a message from the pump 14 that the pump 14 has delivered $\frac{1}{10}$ U of insulin, the UI processor 50 is operable to control the display device 18 to update the displayed TRB value by subtracting $\frac{1}{10}$ U from the displayed value of TRB. Thereafter at step 768, the UI processor 50 is operable to determine whether a user has manually stopped the insulin delivery process by manually selecting a suitable one or more of the user buttons 16 of the remote electronic device 12. If the UI processor 50 determines that the user has manually stopped the delivery of insulin by the pump 14, the process 750 advances to step 770 where UI processor 50 controls the display device 18 to display a bolus canceled message. Otherwise, the process 750 advances to step 772 where the UI processor 50 is operable to determine, based on messages wirelessly provided by the pump 14, whether delivery of the standard bolus is complete. If not, the process 750 loops back up to step 766. Thus, steps 766-772 illustratively result in a count down on the display device 18 of bolus delivery from the total recommended bolus value, TRB. When delivery of the standard bolus is complete, step 772 advances to step 774 where the UI processor 50 is operable to control the display device 18 to display a delivery complete message. From step 774, and also from step 770, the process 750 advances to step 776 where the UI processor 50 stores the bolus delivery record in memory.

Figure 22A:
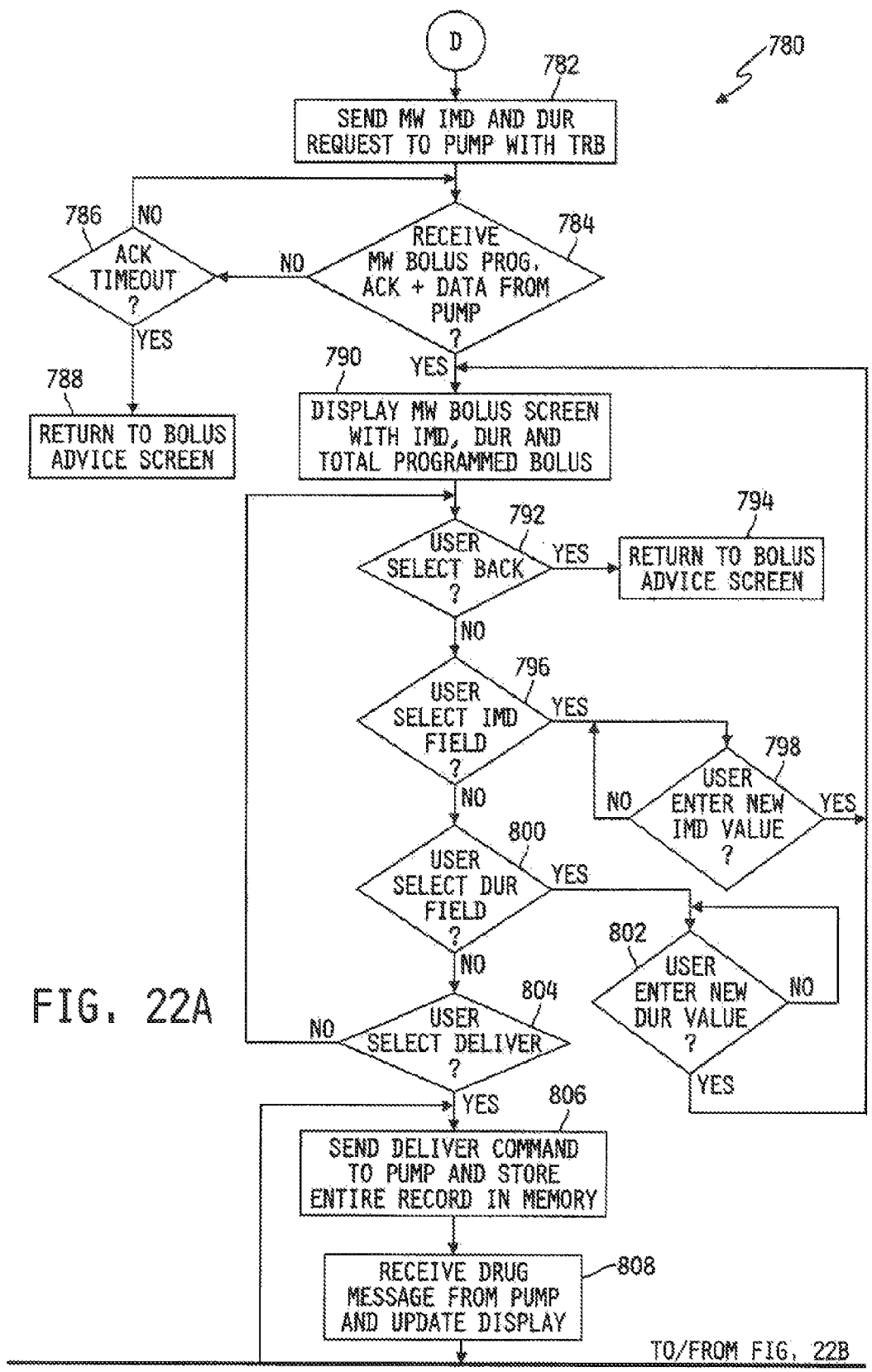
FIGS. 22A and 22B show a flowchart of another illustrative sub-process carried out by the remote electronic device in the bolus advice process of FIGS. 10A-10C.
Figure 22B:
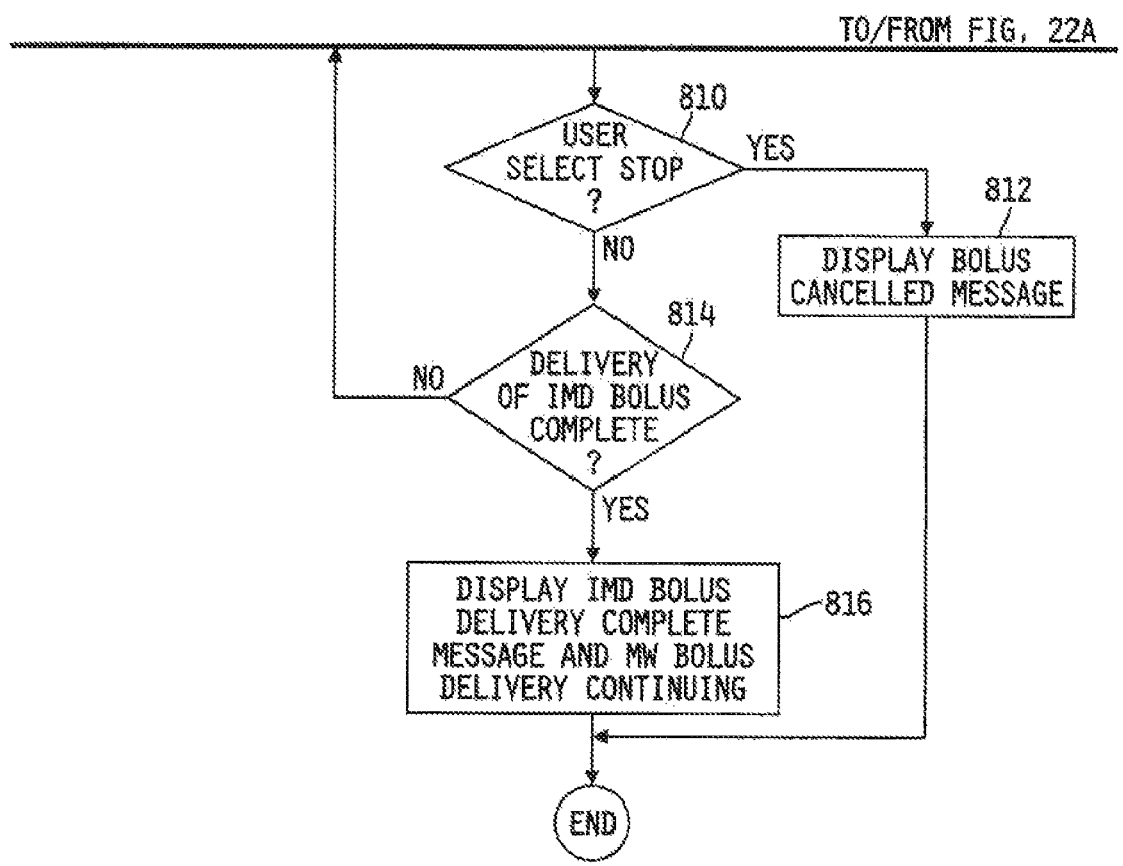

Referring now to FIGS. 22A and 22B, a flowchart is shown of one illustrative embodiment 780 of the process D referred to in the process 670 of FIG. 10C. The process 780 is executed when the user has confirmed a multi-wave bolus of an amount TRB. The process 780 begins at step 782 where the UI processor 50 is operable to send a MW immediate portion (IMD) and duration (DUR) request to the pump 14 along with the total recommended bolus value, TRB. Thereafter at step 784, the UI processor 50 is operable to determine whether a multi-wave bolus program command acknowledgement and accompanying multi-wave bolus data have been received from the pump 14. Illustratively, the pump 14 is responsive to the MW bolus program command to automatically program a multi-wave bolus in the amount of TRB using previous or default values of the immediate portion, IMD, and of the duration, DUR, of the extended portion of the multi-wave bolus, and to send an acknowledgement back to the remote electronic device 12 that a multi-wave bolus in the amount of TRB has been programmed having an immediate amount of IMD and a duration of DUR, and to await further instructions.

If the UI processor 50 determines at step 784 that such an acknowledgement has not been received, the process 780 advances to step 786 where the UI processor 50 is operable to determine whether an acknowledgement timer has timed out since sending the command at step 782. If not, the process 780 loops back to step 784. If the acknowledgement timer has timed out, the process 780 advances to step 788 where the UI processor returns to the previous bolus advice screen.

If, at step 784, the UI processor 50 determines that the multi-wave bolus program acknowledgement and accompanying programmed bolus data was received, the process 780 advances to step 790 where the UI processor 50 is operable to display a multi-wave bolus confirmation screen with the immediate portion, IMD, the bolus duration, DUR, and the total programmed bolus amount. Thereafter at step 792, the UI processor 50 is operable to determine whether the user has selected a back, i.e., go back, function that is available on the confirmation screen. If so, the process 780 advances to step 794 where the UI processor 50 is operable to return to the previous bolus advice screen. If not, the process 780 advances to step 796 where the UI processor 50 is operable to determine whether the user has selected the IMD field of the multi-wave bolus screen for editing. If so, the process 780 advances to step 798 where the UI processor 50 is operable to determine whether the user has entered a new IMED value in the IMD field of the multi-wave bolus screen. If not, the process 780 loops back to the beginning of step 798. If so, the process 780 loops back to step 790. If, at step 796, the UI processor 50 determines that the user has not selected the IMD field for editing, the process 780 advances to step 800 where the UI processor 50 is operable to determine whether the user has selected the DUR field of the multi-wave bolus screen for editing. If so, the process 780 advances to step 802 where the UI processor 50 is operable to determine whether the user has entered a new DUR value in the DUR field of the multi-wave bolus screen. If not, the process 780 loops back to the beginning of step 802. If so, the process 780 loops back to step 790. If, at step 800, the UI processor 50 determines that the user has not selected the IMD field for editing, the process 780 advances to step 804 where the UI processor 50 is operable to determine whether the user has selected the deliver function of the multi-wave bolus screen. If, at step 806, the UI processor 50 has determined that the user has selected deliver on the multi-wave bolus confirmation screen, the UI processor 50 sends a deliver command to the pump 14 to which the pump is responsive to begin delivering the multi-wave bolus in the amount of the total programmed bolus having an immediate portion, IMD, and a duration, DUR.

The process 780 advances from the "YES" branch of step 804 to step 806 where the UI processor 50 is operable to send a deliver command to the pump 14 and to store the entire bolus advice record in memory. Thereafter at step 808, the UI processor 50 is operable to receive a wireless message from the pump 14 corresponding to an amount of the immediate portion, IMD, of the multi-wave bolus that is currently being delivered. The UI processor 50 is, in turn, operable to control the display device 18 to update the immediate bolus value, IMD, to reflect delivery by the pump 14 of the immediate bolus amount so far delivered. For example, if at step 808 the UI processor 50 receives a message from the pump 14 that the pump 14 has delivered ¹⁄₁₀ U of insulin, the UI processor 50 is operable to control the display device 18 to update the displayed IMD value by subtracting ¹⁄₁₀ U from the displayed value of IMD. Thereafter at step 610, the UI processor 50 is operable to determine whether a user has manually stopped the insulin delivery process by manually selecting a suitable one or more of the user buttons 16 of the remote electronic device 12. If the UI processor 50 determines that the user has manually stopped the delivery of insulin by the pump 14, the process 780 advances to step 812 where UI processor 50 controls the display device 18 to display a bolus canceled message. Otherwise, the process 780 advances to step 814 where the UI processor 50 is operable to determine, based on messages wirelessly provided by the pump 14, whether delivery of the immediate portion of the multi-wave bolus is complete. If not, the process 780 loops back up to step 808. Thus, steps 808-814 illustratively result in a count down on the display device 18 of delivery of the immediate portion of the multi-wave bolus. When delivery of the immediate portion of the multi-wave bolus is complete, step 814 advances to step 816 where the UI processor 50 is operable to control the display device 18 to display an immediate bolus delivery complete message that is followed by or that includes a message that the multi-wave bolus delivery is continuing.

Figure 23:
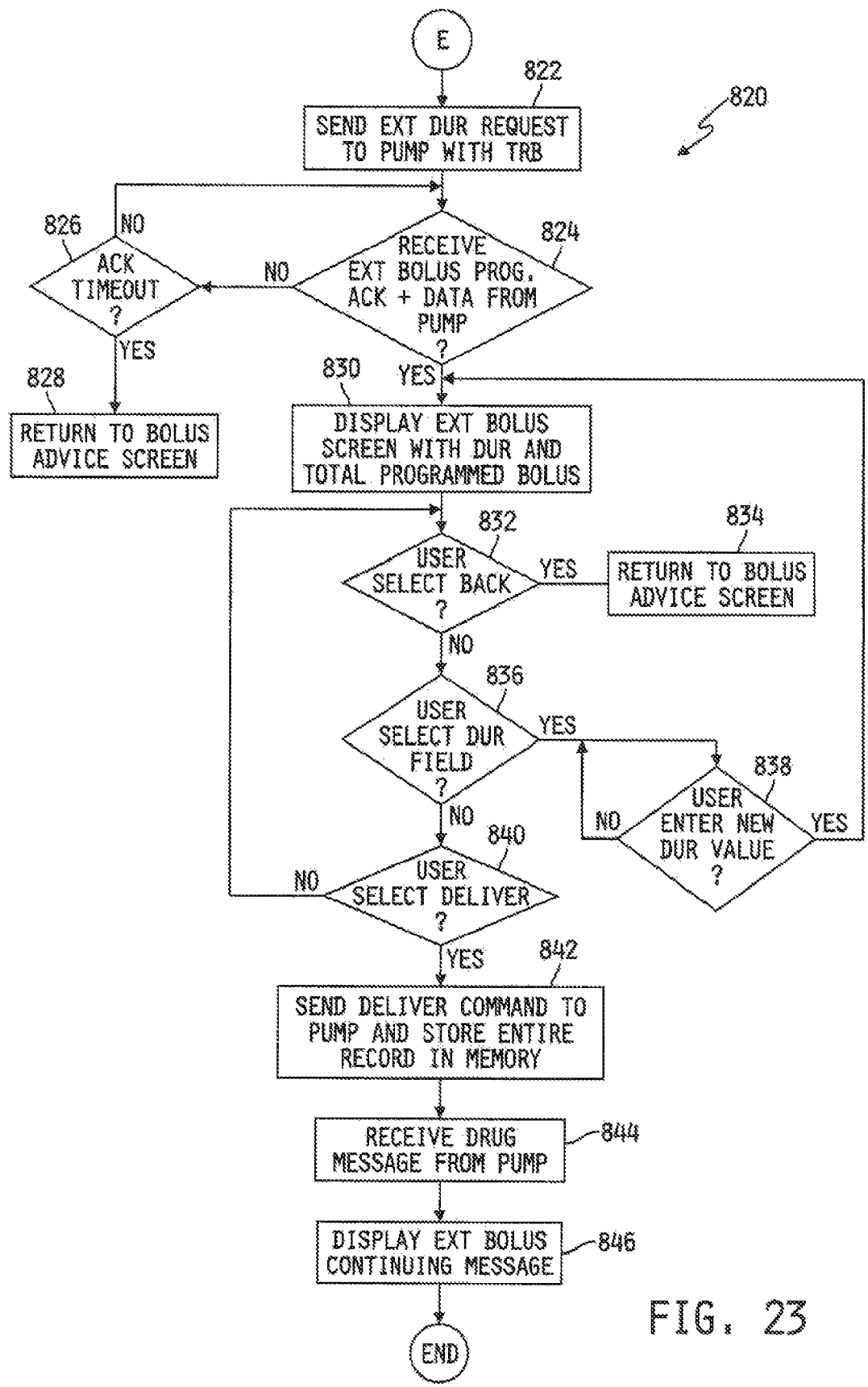
FIG. 23 shows a flowchart of yet another illustrative sub-process carried out by the remote electronic device in the bolus advice process of FIGS. 10A-10C.

Referring now to FIG. 23, a flowchart is shown of one illustrative embodiment 820 of the process E referred to in the process 670 of FIG. 10C. The process 820 is executed when the user has confirmed an extended bolus of an amount TRB. The process 820 begins at step 822 where the UI processor 50 is operable to send an extended bolus duration (DUR) request to the pump 14 along with the total recommended bolus value, TRB. Thereafter at step 824, the UI processor 50 is operable to determine whether an extended bolus program command acknowledgement and accompanying extended bolus data have been received from the pump 14. Illustratively, the pump 14 is responsive to the extended bolus program command to automatically program an extended bolus in the amount of TRB using a previous or default value of the duration, DUR, of the extended bolus, and to send an acknowledgement back to the remote electronic device 12 that an extended bolus in the amount of TRB has been programmed, and to await further instructions. If the UI processor 50 determines at step 824 that such an acknowledgement has not been received, the process 820 advances to step 826 where the UI processor 50 is operable to determine whether an acknowledgement timer has timed out since sending the command at step 822. If not, the process 820 loops back to step 824. If the acknowledgement timer has timed out, the process 820 advances to step 828 where the UI processor returns to the previous bolus advice screen.

If, at step 824, the UI processor 50 determines that the extended bolus program acknowledgement and accompanying programmed bolus data was received, the process 820 advances to step 830 where the UI processor 50 is operable to display an extended bolus confirmation screen with the bolus duration, DUR, and the total programmed bolus amount. Thereafter at step 832, the UI processor 50 is operable to determine whether the user has selected a back, i.e., go back, function that is available on the confirmation screen. If so, the process 820 advances to step 834 where the UI processor 50 is operable to return to the previous bolus advice screen. If not, the process 820 advances to step 836 where the UI processor 50 is operable to determine whether the user has selected the DUR field of the multi-wave bolus screen for editing. If so, the process 820 advances to step 838 where the UI processor 50 is operable to determine whether the user has entered a new DUR value in the DUR field of the extended bolus screen. If not, the process 820 loops back to the beginning of step 838. If so, the process 820 loops back to step 830. If, at step 836, the UI processor 50 determines that the user has not selected the DUR field for editing, the process 820 advances to step 840 where the UI processor 50 is operable to determine whether the user has selected the deliver function of the multi-wave bolus screen. If, at step 840, the UI processor 50 has determined that the user has selected deliver on the extended bolus confirmation screen, the UI processor 50 sends a deliver command to the pump 14 to which the pump is responsive to begin delivering the extended bolus in the amount of the total programmed bolus having a duration, DUR.

The process 820 advances from the "YES" branch of step 840 to step 842 where the UI processor 50 is operable to send a deliver command to the pump 14 and to store the entire bolus advice record in memory. Thereafter at step 844, the UI processor 50 is operable to receive a wireless message from the pump 14 that the pump is currently delivering the extended bolus. Thereafter at step 846, the UI processor 50 is operable to control the display unit 18 to display a message indicating that delivery of the extended bolus is continuing.

Figure 24:
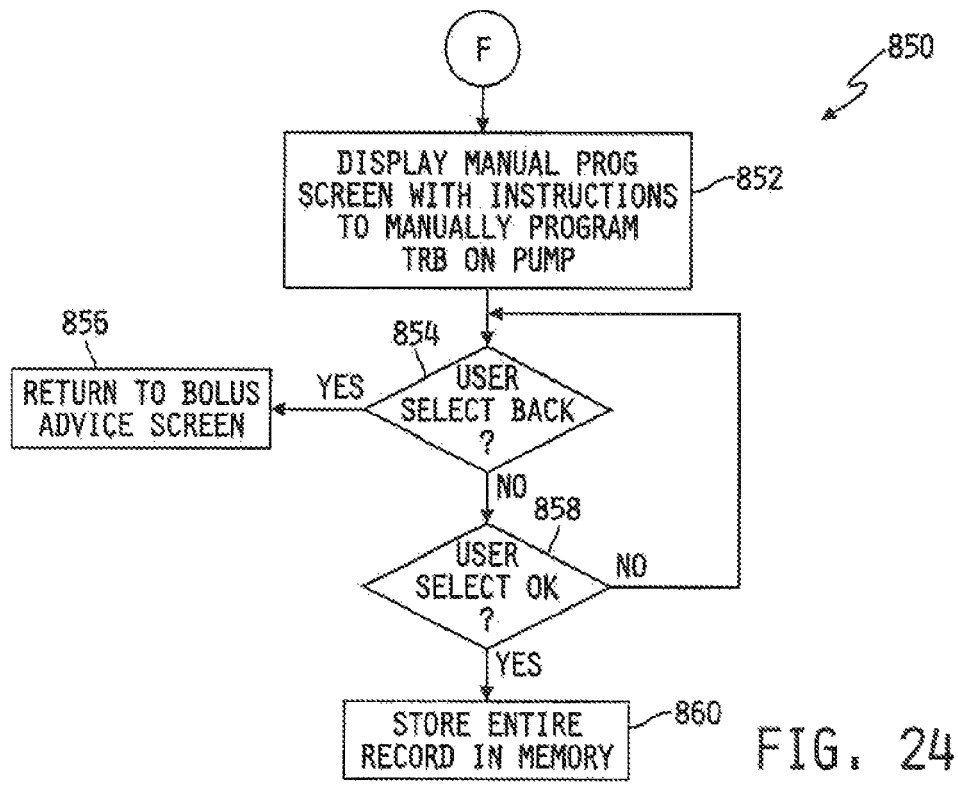
FIG. 24 shows a flowchart of still another illustrative sub-process carried out by the remote electronic device in the bolus advice process of FIGS. 10A-10C.

Referring now to FIG. 24, a flowchart is shown of one illustrative embodiment 850 of the process F referred to in the process 670 of FIG. 10C. The process 850 is executed when the user has confirmed that the bolus amount TRB will be manually programmed on the pump 14. The process 850 begins at step 852 where the UI processor 50 is operable to display a manual program screen with instructions to manually program the bolus amount TRB on the pump 14. Thereafter at step 854, the UI processor 50 is operable to determine whether the user has selected a back, i.e., go back, function that is available on the confirmation screen. If so, the process 850 advances to step 856 where the UI processor 50 is operable to return to the previous bolus advice screen. If not, the process 850 advances to step 858 where the UI processor 50 is operable to determine whether the user has selected OK on the manual program bolus screen. If not, the process 850 loops back to step 854. If, at step 858, the UI processor 50 has determined that the user has selected OK on the bolus confirmation screen, the UI processor 50 stores the entire record in memory at step 860.

Figure 25:
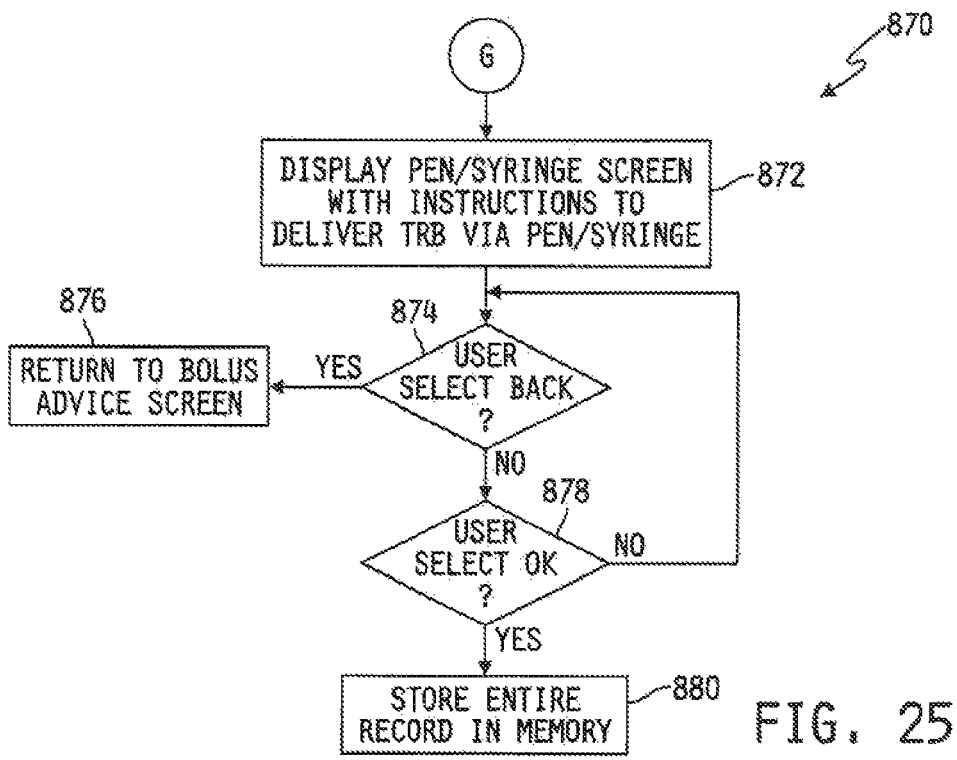
FIG. 25 shows a flowchart of a further illustrative sub-process carried out by the remote electronic device in the bolus advice process of FIGS. 10A-10C.

Referring now to FIG. 25, a flowchart is shown of one illustrative embodiment 870 of the process G referred to in the process 670 of FIG. 10C. The process 870 is executed when the user has confirmed that the bolus amount TRB will be manually delivered via a drug pen or syringe or the like. The process 870 begins at step 872 where the UI processor 50 is operable to display a pen/syringe screen with instructions to manually deliver the bolus amount TRB via a drug pen or syringe. Thereafter at step 874, the UI processor 50 is operable to determine whether the user has selected a back, i.e., go back, function that is available on the confirmation screen. If so, the process 870 advances to step 876 where the UI processor 50 is operable to return to the previous bolus advice screen. If not, the process 870 advances to step 878 where the UI processor 50 is operable to determine whether the user has selected OK on the manual program bolus screen. If not, the process 870 loops back to step 874. If, at step 878, the UI processor 50 has determined that the user has selected OK on the bolus confirmation screen, the UI processor 50 stores the entire record in memory, at step 880.

While the invention has been illustrated and described in detail in the foregoing drawings and description, the same is to be considered as illustrative and not restrictive in character, it being understood that only illustrative embodiments thereof have been shown and described and that all changes and modifications that come within the spirit of the invention are desired to be protected.

What is claimed is:

1. A method reconciling bolus records between an electronic device including a blood glucose meter and a liquid infusion pump for more accurate records to improve therapy advice, comprising:

transferring commanded pump event records not previously transmitted to an electronic device including a blood glucose meter, each commanded pump event record having delivered bolus information;

associating the delivered bolus information with electronic device diary records having programmed bolus information that is not confirmed;

if the delivered bolus information is associated with the programmed bolus information, updating the programmed bolus information with delivered bolus information and confirming the delivered bolus information is associated with the programmed bolus information to prevent other associations;

if the delivered bolus information is not associated with the programmed bolus information, creating a new electronic device diary record having programmed bolus information including the delivered bolus information and confirming the delivered bolus information is associated with the programmed bolus information to prevent other associations; and improving accuracy of programmed bolus information by modifying the programmed bolus information with delivered bolus information for more accurate records to improve therapy advice.

2. The method as in claim 1, further comprising transferring non-commanded pump event records, created by manually initiated directly delivered boluses from a pump, insulin pen, or syringe, not previously transmitted to the electronic device, each non-commanded pump event record having a delivered bolus type, delivered bolus amount, and a delivered time stamp;

updating the electronic device diary records with non-commanded pump event records; and improving accuracy of electronic device diary records with non-commanded pump event records for improved therapy advice.

3. The method as in claim 1, wherein associating the commanded pump event record bolus information with electronic device non-confirmed diary records programmed bolus information is performed within a predetermined variation between a delivered bolus time stamp and a programmed bolus time stamp.

4. The method as in claim 1, wherein the predetermined variation of the delivered bolus time stamp and programmed bolus time stamp is less than six minutes.

5. The method as in claim 1, wherein delivered bolus information comprises a delivered bolus type, delivered bolus amount, and delivered bolus time stamp.

6. The method as in claim 1, wherein programmed bolus information comprises a programmed bolus type, programmed bolus amount, and programmed bolus time stamp.

7. A method reconciling bolus records between an electronic device including a blood glucose meter and a liquid infusion pump for more accurate records to improve therapy advice, comprising:

means for transferring commanded pump event records not previously transmitted to an electronic device including a blood glucose meter, each commanded pump event record having delivered bolus information;

means for associating the delivered bolus information with electronic device diary records having programmed bolus information that is not confirmed;

if the delivered bolus information is associated with the programmed bolus information, means for updating the programmed bolus information with delivered bolus information and confirming the delivered bolus information is associated with the programmed bolus information to prevent other associations;

if the delivered bolus information is not associated with the programmed bolus information, means for creating a new non-confirmed diary record have programmed bolus information including the delivered bolus information and confirming the delivered bolus information is associated with the programmed bolus information to prevent other associations; and improving accuracy of programmed bolus information by modifying the programmed bolus information with delivered bolus information for more accurate records to improve therapy advice.

8. The method as in claim 7, further comprising means for transferring non-commanded pump event records, created by manually initiated directly delivered boluses from a pump, insulin pen, or syringe, not previously transmitted to the electronic device, each non-commanded pump event record having a delivered bolus type, delivered bolus amount, and a delivered time stamp;

means for updating the electronic device diary records with non-commanded pump event; and improving accuracy of electronic device diary records with non-commanded pump event records for improved therapy advice.

* * * * *